(12) United States Patent
Kaplan et al.

(10) Patent No.: US 10,874,742 B2
(45) Date of Patent: Dec. 29, 2020

(54) SHAPE MEMORY SILK MATERIALS

(71) Applicant: Tufts University, Medford, MA (US)

(72) Inventors: David L. Kaplan, Concord, MA (US); Fiorenzo G. Omenetto, Lexington, MA (US); Joseph E. Brown, Somerville, MA (US); Rodrigo R. Jose, Medford, MA (US)

(73) Assignee: Tufts University, Medford, MA (US)

( * ) Notice: Subject to any disclaimer, the term of this patent is extended or adjusted under 35 U.S.C. 154(b) by 335 days.

(21) Appl. No.: 15/555,225

(22) PCT Filed: Mar. 11, 2016

(86) PCT No.: PCT/US2016/021939
§ 371 (c)(1),
(2) Date: Sep. 1, 2017

(87) PCT Pub. No.: WO2016/145281
PCT Pub. Date: Sep. 15, 2016

(65) Prior Publication Data
US 2018/0050109 A1 Feb. 22, 2018

Related U.S. Application Data

(60) Provisional application No. 62/132,429, filed on Mar. 12, 2015.

(51) Int. Cl.
| | | |
|---|---|---|
| *A61L 31/04* | (2006.01) | |
| *C07K 14/435* | (2006.01) | |
| *C08J 9/28* | (2006.01) | |
| *A61K 47/42* | (2017.01) | |
| *D01F 4/02* | (2006.01) | |
| *A61L 31/14* | (2006.01) | |
| *C08J 9/00* | (2006.01) | |
| *A61K 47/26* | (2006.01) | |
| *A61B 17/00* | (2006.01) | |
| *C08H 1/00* | (2006.01) | |

(52) U.S. Cl.
CPC ............ *A61K 47/42* (2013.01); *A61K 47/26* (2013.01); *A61L 31/146* (2013.01); *C07K 14/43518* (2013.01); *C07K 14/43586* (2013.01); *C08J 9/0085* (2013.01); *D01F 4/02* (2013.01); *A61B 2017/00867* (2013.01); *A61L 2400/16* (2013.01); *C08H 1/00* (2013.01); *C08J 2389/00* (2013.01)

(58) Field of Classification Search
CPC ............ A61B 2017/00871; A61K 9/00; A61K 9/0087; A61K 9/19; A61K 47/42; A61L 31/14; A61L 31/146; A61L 2400/16; A61M 2205/0266; C07K 14/43518; C07K 14/43586; C08H 1/00; C08J 3/18; C08J 9/00; C08J 9/0085; C08J 2205/00; C08J 2389/00; C08J 2489/00; D01F 4/02
See application file for complete search history.

(56) References Cited

U.S. PATENT DOCUMENTS

| 5,245,012 A | 9/1993 | Lombari et al. | |
|---|---|---|---|
| 8,247,384 B2 | 8/2012 | Green et al. | |
| 9,328,135 B2* | 5/2016 | Kobayashi | ................. C08J 9/28 |
| 2002/0081408 A1* | 6/2002 | Spaller | ................. B65D 1/0223 |
| | | | 428/35.7 |
| 2004/0067503 A1 | 4/2004 | Tan et al. | |
| 2009/0232963 A1* | 9/2009 | Kaplan | .................... C08H 1/00 |
| | | | 427/2.24 |
| 2010/0168011 A1* | 7/2010 | Jennings, Jr. | ......... A61K 9/0043 |
| | | | 514/1.1 |
| 2010/0279112 A1* | 11/2010 | Kaplan | ................. A61L 27/227 |
| | | | 428/357 |

FOREIGN PATENT DOCUMENTS

| WO | WO-1997/008315 A1 | 3/1997 | | |
|---|---|---|---|---|
| WO | WO-2004/080346 A2 | 9/2004 | | |
| WO | WO-2005/12606 A2 | 2/2005 | | |
| WO | WO-2005/123114 A2 | 12/2005 | | |
| WO | WO-2007/016524 A2 | 2/2007 | | |
| WO | WO-2008/118133 A2 | 10/2008 | | |
| WO | WO-2008/150861 A1 | 12/2008 | | |
| WO | WO-2010/042798 A2 | 4/2010 | | |
| WO | WO-2010/057142 A2 | 5/2010 | | |
| WO | WO-2013070907 A1 * | 5/2013 | ............ | A61L 27/227 |
| WO | WO-2014011644 A1 * | 1/2014 | ............. | A61L 27/54 |
| WO | WO-2016/145281 A1 | 9/2016 | | |

OTHER PUBLICATIONS

Nam et al. Morphology of Regenerated Silk Fibroin: Effects of Freezing Temperature, Alcohol Addition, and Molecular Weight. Journal of Applied Polymer Science. 2001, vol. 81, pp. 3008-3021. (Year: 2001).*
Altman, G. H. et al., Silk-based biomaterials, Biomaterials, 24: 401-416 (2003).
Bellas, E. et al, Sustained volume retention in vivo with adipocyte and lipoaspirate seeded silk scaffolds, Biomaterials, 34(12): 2960-8 (2013).
Bellas, E.et al, Injectable Silk Foams for Soft Tissue Regeneration, Advanced Healthcare Materials, 4(3): 452-459 (2015).
Bencherif, S.A. et al, Injectable preformed scaffolds with shape-memory properties, Proc. Natl. Acad. Sci. USA, 109(48):19590-5 (2012).
Bini, E. et al, Mapping Domain Structures in Silks from Insects and Spiders Related to Protein Assembly, J. Mol. Biol. 335(1): 27-40 (2004).
Correia, C.O. and Mano, J.F., Chitosan scaffolds with a shape memory effect induced by hydration, J. Mater Chem. B, 2(21):3315-23 (2014).

(Continued)

*Primary Examiner* — Jeffrey E. Russel
(74) *Attorney, Agent, or Firm* — Quarles & Brady LLP

(57) ABSTRACT

The present application relates to silk fibroin-based materials, methods for making and using the same. Provided materials exhibit shape memory characteristics while showing comparable or better volumetric swelling, biocompatibility and/or degradability when compared to current memory polymers derived from either natural or synthetic materials.

20 Claims, 24 Drawing Sheets

(56) References Cited

OTHER PUBLICATIONS

Discher, D. E. et al, Growth factors, matrices, and forces combine and control stem cells, Science 324(5935): 1673-1677 (2009).
Gil, E. S. et al, Mechanically robust, rapidly actuating, and biologically functionalized macroporous poly(N-isopropylacrylamide)/silk hybrid hydrogels, Langmuir, 26 (19): 15614-24 (2010).
Gil, E. S., and Hudson, S. M., Effect of Silk Fibroin Interpenetrating Networks on Swelling/Deswelling Kinetics and Rheological Properties of Poly(N-isopropylacrylamide) Hydrogels, Biomacromolecules, 8:258-264 (2007).
Guziewicz, N. et al, Lyophilized silk fibroin hydrogels for the sustained local delivery of therapeutic monoclonal antibodies, *Biomaterials*, 32(10): 2642-2650 (2011).
Hager, M. D. et al, Shape memory polymers: Past, present and future developments, *Progress in Polymer Science*, (49-50):3-33 (2015).
Hu, X et al, Determining beta-sheet crystallinity in fibrous proteins by thermal analysis and infrared spectroscopy, Macromolecules, 39(18): 6161-6170 (2006).
International Search Report for PCT/US2016/021939, 4 pages, dated Sep. 1, 2016.
Jose, R..R.. et al, Polyol-Silk Bioink Formulations as Two-Part Room-Temperature Curable Materials for 3D Printing, ACS Biomaterials Science & Engineering 1(9): 780-788 (2015).
Kikuchi, Y. et al, Structure of the *Bombyx mori* fibroin light-chain-encoding gene: upstream sequence elements common to the light and heavy chain, Gene, 110:151-158 (1992).
Lawrence, B. D. and Omenetto, F., Processing methods to control silk fibroin film biomaterial features, J. Materials Science 43(21): 6967-6985 (2008).
Lu, Q. et al, Water-insoluble silk films with silk I structure, Acta Biomaterialia, 6(4): 1380-1387 (2010).
Lu, S. et al., Insoluble and flexible silk films containing glycerol, Biomacromolecules, 11(1): 143-50 (2010).
Lucas, F. et al., The Silk Fibroins, Adv. Protein Chem, 13: 107-242 (1958).
Lutolf, M. P. and Hubbell, J. A., Synthetic biomaterials as instructive extracellular microenvironments for morphogenesis in tissue engineering, Nature Biotechnology 23(1): 47-55 (2005).
Mandal, B. B et al, Laminar Silk Scaffolds for Aligned Tissue Fabrication, Macromolecular Bioscience, 13(1): 48-58 (2013).
Meinel, L. et al, The inflammatory responses to silk films in vitro and in vivo, Biomaterials, 26(2):147-155 (2005).
Murphy, A. R. et al, Modification of silk fibroin using diazonium coupling chemistry and the effects on hMSC proliferation and differentiation. Biomaterials 29:2829-2838 (2008).
O'Brien, F. J et al, Influence of freezing rate on pore structure in freeze-dried collagen-GAG scaffolds, Biomaterials, 25(6): 1077-1086 (2004).
Omenetto, F. G. and Kaplan, D. L., New Opportunities for an Ancient Material, Science 329: 528-531 (2010).
Patel, S. M. et al, Determination of End Point of Primary Drying in Freeze-Drying Process Control, AAPS PharmSciTech, 11(1): 73-84 (2010).
Pei, Y. et al, Mild process to design silk scaffolds with reduced β-sheet structure and various topographies at nanometer scale, Acta Biomaterialia, 13:168-176 (2015).
Pielak, G. J. et al, Azo protein analogues: synthesis and characterization of arsanilazo and sulfanilazo derivatives of tyrosine and histidine, Biochemistry, 23 :589-596 (1984).
Ramos, O. L., Effect of whey protein purity and glycerol content upon physical properties of edible films manufactured therefrom, Food Hydrocolloids, 30 (1): 110-122 (2013).
Rnjak-Kovacina, J. et al, Lyophilized silk sponges: a versatile biomaterial platform for soft tissue engineering, ACS Biomaterials Science & Engineering, 1(4): 260-270 (2015).
Rockwood, D. N. et al, Materials fabrication from *Bombyx mori* silk fibroin, Nature Protocols, 6(10):1612-31 (2011).
Safranski, D.L., Mechanical requirements of shape-memory polymers in biomedical devices, Polym. Rev. 53(1):76-91 (2013).
Sashina, E. S. et al., Structure and Solubility of Natural Silk Fibroin, Russ. J. Appl. Chem, 79(6): 869-876 (2006).
Takei, F. et al, Further Evidence for Importance of the Subunit Combination of Silk Fibroin in Its Efficient Secretion from the Posterior Silk Gland Cells, J. Cell Biol., 105:175-180 (1987).
Tanaka, K. et al, Determination of the site of disulfide linkage between heavy and light chains of silk fibroin produced by *Bombyx mori*, Biochim. Biophys. Acta., 1432:92-103 (1999).
Tanaka, K., et al, Immunological Identification of the Major Disulfide-Linked Light Component of Silk Fibroin, J. Biochem. 114(1):1-4 (1993).
Thurber, A E. et al., In vivo bioresponses to silk proteins, Biomaterials, 71:145-157 (2015).
Wang, Y. et al, In vivo degradation of three-dimensional silk fibroin scaffolds, Biomaterials, 29:3415-3428 (2008).
Wong, Y, Biomedical applications of shape-memory polymers: how practically useful are they?, Sci. China Chem, 57(4):476-89 (2014).
Written Opinion for PCT/US2016/021939, 5 pages, dated Sep. 1, 2016.

\* cited by examiner

SHAPE MEMORY SILK MATERIALS

CROSS-REFERENCE TO RELATED APPLICATIONS

This patent application is a National Stage Entry of International Patent Application No. PCT/US2016/021939, filed on Mar. 11, 2016, which claims the benefit of priority of U.S. Provisional Application Ser. No. 62/132,429 filed on Mar. 12, 2015, entitled "Shape Memory Silk Materials", the entire contents of each of which are hereby incorporated by reference herein.

GOVERNMENT SUPPORT

This invention was made with government support under grant EB002520 awarded by the National Institutes of Health and grant W81XWH-14-2-0004 awarded by the United States Army. The government has certain rights in the invention.

BACKGROUND

Stimuli-responsive polymers are a subclass of "smart" materials that can recover from a deformed shape back to an original, pre-defined shape in the presence of an external stimuli. Materials exhibiting this behavior are often known as shape memory polymers (SMPs).

SUMMARY OF THE INVENTION

Among other things, the present disclosure provides silk fibroin-based materials having shape memory properties. The present disclosure also provides methods of making and using such silk fibroin-based materials.

Implementations of the present disclosure are useful for a wide range of applications, including but not limited to: biomaterials, biomedical devices, biosensing, controlled release applications, drug delivery, electronics, materials for tunable degradation, optics, photonics, prosthetics, regenerative medicine, robotics, tissue engineering applications, tissue regeneration, tissue scaffolding, and/or wound clotting.

Provided silk fibroin-based materials, in some embodiments, specifically offer possibilities for a multitude of unique uses as fillers, packing materials, sensors, and for a range of different devices. Provided silk fibroin-based materials, for example, are useful as implantable biomedical devices. In some embodiments, provided silk fibroin-based materials are compressible, and may be introduced into an insertion device for in vivo implantation thereof. Once implanted, such materials may be expanded, for example by means of a trigger and/or external stimulus. In some embodiments, such materials, upon expansion, substantially recover their original shape. Biomedical devices comprised of such materials, for example, can thus be implanted via a minimally invasive technique. Such minimally invasive implantation techniques are often desirable over complex, highly invasive surgeries and/or medical procedures.

In some embodiments, provided silk fibroin-based materials are susceptible to compression (e.g., materials are characterized in that they can adopt at least two different states—a pre-compression state and a compressed state— and in some embodiments at least three different states—a pre-compression state, a compressed state, and an expanded state which may, in some embodiments, be substantially identical to the pre-compression state). In some embodiments, compression reduces a material's volume relative to its initial, pre-compression volume. Alternatively or additionally, in some embodiments, compression results in shape deformation. Thus, in some embodiments, compressed silk fibroin-based materials as described herein have a smaller volume and/or deformed shape relative to an otherwise identical material that has not undergone compression.

In some embodiments, silk fibroin-based materials as described herein are characterized in that, when in their compressed state, they retain their reduced volume and/or deformed shape until exposed to a trigger and/or external stimulus.

In some embodiments, when exposed to a trigger and/or external stimulus, compressed silk fibroin-based materials will recover to a larger volume, in some embodiments, to a volume that is substantially identical to their pre-compression volume. In some embodiments, following exposure to a trigger and/or external stimulus, compressed silk fibroin-based materials recover to an un-deformed shape, in some embodiments to a shape that is substantially identical to their pre-compression shape.

In some embodiments, when exposed to a trigger and/or external stimulus, compressed silk fibroin-based materials are characterized by volumetric expansion from their compressed state. In some embodiments, when exposed to a trigger and/or external stimulus, compressed silk fibroin-based materials swell.

In some embodiments, a trigger and/or external stimulus comprises or consists of, for example: heat, electrical or magnetic fields, pH, light, pressure, water, ions, enzymes, or sugar, and combinations thereof. In some embodiments, a trigger and/or external stimulus comprises or consists of, for example, exposure of the silk fibroin-based material to an aqueous medium, such as water, phosphate buffered saline ("PBS"), or a cell culture media, such as Dulbecco's Modified Eagle's Medium ("DMEM"), fetal bovine serum, bodily fluids; or combinations thereof.

In some embodiments, silk fibroin-based materials are formed silk fibroins produced from silks of various insects, including silkworms.

In some embodiments, provided silk fibroin-based materials are characterized in that they include silk fibroin within a particular molecular weight range so that, as described herein, the materials display one or more desirable characteristics. In some embodiments, provided technologies for selecting, designing, and/or producing silk fibroin-based materials as described herein include selection, design and/or production of such silk fibroin within a particular molecular weight range, so that materials having one or more desired (e.g., pre-determined desired) characteristics are provided.

For example, in some embodiments, silk fibroin-based materials are or comprise silk fibroin and/or silk fibroin fragments. In some embodiments, silk fibroin and/or silk fibroin fragments of various molecular weights may be used. In some embodiments, silk fibroin and/or silk fibroin fragments of various molecular weights are or comprise silk fibroin polypeptides. In some embodiments, an average molecular weight of silk fibroin polypeptides is for example, between about 3 kDa and about 400 kDa.

In some embodiments, preparations of silk fibroin polypeptides within a particular molecular weight range may be prepared by heat treatment (e.g., by boiling). In some embodiments, such heat treatment is applied for a specified period of time, for example within a range of about five minutes to about 120 minutes or longer. Relationship between boiling time and silk fibroin molecular weight has been established for aqueous solutions of silk fibroin; those of ordinary skill in the art are therefore well able to prepare silk fibroin polypeptides within a molecular weight range of interest in order to prepare silk fibroin-based materials as described herein.

In some embodiments, silk fibroin is processed from aqueous silk solutions.

In some embodiments, silk fibroin-based materials processed from aqueous silk solutions have exhibited favorable characteristics, including, for example: desirable mechanical, electrical, and optical properties, environmental stability, biocompatibility, and tunable degradation.

In some embodiments, silk fibroin-based materials are processed from silk solutions (e.g., aqueous solutions) that have a silk solution concentration between about 1% silk to about 50% silk.

In some embodiments, silk fibroin-based materials are processed from silk solutions (e.g., aqueous solutions) to form varied material formats, such as fibers, foams, particles, films, and/or hydrogels.

In some embodiments, silk fibroin-based materials are comprised of modified silk.

In some embodiments, modified silk differs from unmodified silk due addition of one or more pendant moieties (e.g., to an R group of an amino acid), inclusion of one or more non-natural amino acids, association with (e.g., covalent linkage to) one or more moieties such as a peptide, lipid, carbohydrate, nucleic acid, small molecule, metal, etc.

In some embodiments, modified silk differs from unmodified silk because an additive, agent, and/or functional moiety reacts with silk in a silk solution during manufacturing of silk fibroin-based materials. In some embodiments, modified silk differs from unmodified silk because an additive, agent, and/or functional moiety is mixed with a silk solution during manufacturing of silk fibroin-based materials. In some embodiments, modified silk differs from unmodified silk because an additive, agent, and/or functional moiety is mixed with, added to, applied to a silk fibroin-based material. In some embodiments, modified silk differs from unmodified silk because an additive, agent, and/or functional moiety reacts with silk in a silk fibroin-based material.

In some embodiments, silk fibroin-based materials comprised of such modified silk are characterized by certain silk fibroin-based materials' unique swelling properties, e.g., as described herein. In some embodiments, modified silk shows improved hydrophilicity relative to unmodified silk. In some embodiments, modified silk shows an improved capacity to absorb water relative to unmodified silk.

In some particular embodiments, for example, a modified silk differs from a natural silk due to modification by 4-sulfonic acid. In some particular embodiments, a modified silk is modified with poly-lysine (e.g., is a fusion peptide comprising a poly-lysine portion and a silk fibroin portion). In some particular embodiments, a modified silk is pegylated. Other exemplary plasticizers are described throughout the present application.

In some embodiments, modified silk shows an improved hydrophobicity relative to unmodified silk. In some embodiments, modified silk shows may be able to increase absorption of non-polar fluids (e.g. oils or fats) in silk materials.

In some particular embodiments, a modified silk is modified with 4-(heptyloxy)aniline. In some particular embodiments, a modified silk is modified with 4'-aminoacetophenone. Other exemplary plasticizers are described throughout the present application.

In some embodiments, a modified silk fibroin-based comprises one or more modified amino acid residues. In some embodiments, a modified amino acid residue is a modified tyrosine residue. In some embodiments, a modified tyrosine residue is covalently modified (e.g., by addition of one or more pendant groups).

In some embodiments, between about 5% and about 75% of the silk fibroin in a silk-fibroin-based material as described herein is or comprises modified silk.

In some embodiments, silk fibroin-based materials include a plasticizer.

In some embodiments, silk fibroin-based materials including a plasticizer enhance certain properties of such materials relative to otherwise identical materials lacking the plasticizer. In some embodiments, plasticizers increase crystallinity of silk fibroin-based materials.

In some embodiments, plasticizers may be or may comprise, for example, glycerol, 1,2 Propanediol, 1,3 Propanediol, 1,4 Butanediol, 1,2,4 Butanetriol, Threitol, Erythritol, 1,2 Pentanediol, 1,5 Pentanediol, Adonitol, 1,2,6 Hexanetriol, sugars such as glucose, sorbitol, or mannitol, or combinations thereof. Other exemplary plasticizers are described through the present application.

In some embodiments, plasticizers are non-toxic. In some embodiments, non-toxic plasticizers preserve biocompatibility of silk fibroin-based materials.

In some embodiments, a ratio of plasticizer to silk is between about 1% to about 75% w/ plasticizer to w/ silk. In some embodiments, a weight ratio of plasticizer to silk is between about 0.05 and about 0.8.

In some embodiments, silk fibroin-based materials are insoluble in water. In some embodiments, silk fibroin-based materials having at least 20% plasticizer are insoluble in water. In some embodiments, silk fibroin-based materials are treated to induce insolubility. In some embodiments, provided silk fibroin-based materials are immersed in methanol. In some embodiments, such methanol treated silk fibroin-based materials are insoluble in water In some embodiments, when incorporated into silk fibroin-based materials, plasticizers of different molecular composition produce silk fibroin-based materials with varying pore characteristics and/or varying properties. In some embodiments, properties include, for example, mechanical, optical, and/or electrical properties.

In some embodiments, silk fibroin-based materials are characterized by unique features that provide advantages over existing shape memory polymers. In some embodiments, silk fibroin-based materials including both a plasticizer and silk that is or comprises modified silk exhibit unique swelling properties as described herein.

In some embodiments, when exposed to a trigger and/or external stimulus, compressed silk fibroin-based materials exhibit volumetric swelling of at least two fold from that of the materials' compressed state. In some embodiments, when exposed to a trigger and/or external stimulus, compressed silk fibroin-based materials that include a plasticizer exhibit volumetric swelling up to about 50 times from that of the materials' compressed state.

In some embodiments, when exposed to a trigger and/or external stimulus (e.g. an aqueous medium), compressed silk fibroin-based materials exhibit swelling by mass of at least about 400% from that of the materials' compressed state. In some embodiments, when exposed to a trigger and/or external stimulus (e.g. an aqueous medium), compressed silk fibroin-based materials that include a plasticizer exhibit swelling by mass of up to about 900% from that of the materials' compressed state.

In some embodiments, silk fibroin-based materials have a structure that includes open cells that are or are described as pores.

In some embodiments, silk fibroin-based materials are characterized by a substantial lack of ice crystals.

In some embodiments, pores in silk fibroin-based materials are characterized by a substantially uniform rounded shape. In some embodiments, pores in silk fibroin-based materials are evenly spaced throughout a volume. In some embodiments, pores in silk fibroin-based materials are interconnected pores that traverse bulk material; in some embodiments such interconnected pores traverse throughout the bulk material.

In some embodiments, pores in silk fibroin-based materials have an average diameter between about 5 µm and about 500 µm.

In some embodiments, as described herein, silk fibroin-based materials are characterized in that they substantially recover after compression. In some embodiments, average pore size in provided silk fibroin-based materials is not compromised by compression or expansion, in that average pore size is substantially identical after recovery from compression and/or expansion relative to the pore size of its pre-compressed state. In some embodiments, pore morphology in provided silk fibroin-based materials is not compromised by compression or expansion, in that one or more features that characterize the materials' pore morphology is substantially identical after recovery from compression and/or expansion relative to its pre-compressed state.

In some embodiments, provided silk fibroin-based materials are characterized by an elastic modulus value in a range between about 1 kPa and about 2500 kPa.

In some embodiments, provided silk fibroin-based materials are characterized by a compressive modulus value in a range between about 500 Pa and about 3000 kPa.

In some embodiments, provided silk fibroin-based materials are characterized by a storage modulus value in a range between about 1 kPa and about 3000 kPa.

In some embodiments, as described herein provided silk fibroin-based materials are characterized in that, when exposed to a compressive strain they substantially recover their volume and/or shape.

In some embodiments, when exposed to a compressive strain of up to 90%, silk fibroin-based materials are compressed to about 10% or less of their original volume. In some such embodiments, provided compressed silk fibroin-based materials are further characterized in that, when exposed to a trigger and/or external stimulus, they substantially recover their volume and/or shape. In some embodiments, recovered materials substantially lack any indication of a plastic deformation.

In some embodiments, when provided silk fibroin-based materials are exposed to a compressive stress of up to about 100 kPa, such materials are further characterized in that exposed to a trigger and/or external stimulus, they substantially recover their volume and/or shape. In some embodiments, recovered materials substantially lack any indication of a plastic deformation.

In some embodiments, silk fibroin-based materials are biocompatible.

In some embodiments, silk fibroin-based materials include additives, agents, and/or functional moieties. In some embodiments, additives, agents, and/or functional moieties include, for example therapeutic agents, cells, organisms, antibodies, nucleic acids, growth factor, hormones, polypeptides, and/or optically or electrically active agents. In some embodiments, additives, agents, and/or functional moieties include, for example: antibiotics, small molecules, enzymes, enzyme inhibitors, anti-inflammatories, and/or drugs.

In some embodiments, silk fibroin-based materials are pre-loaded with additives, agents, and/or functional moieties during material fabrication. In some embodiments, silk fibroin-based materials uptake additives, agents, and/or functional moieties when the material is in a pre-compressed state. In some embodiments, silk fibroin-based materials uptake additives, agents, and/or functional moieties when the material is in an expanded state. In some embodiments, silk fibroin-based materials uptake additives, agents, and/or functional moieties when the material is recovered from compression and/or expansion.

In some embodiments, silk fibroin-based materials are biodegradable.

In some embodiments, silk fibroin-based materials are characterized in that such materials decompose, degrade, delaminate, or dissolve. In some embodiments, silk fibroin-based materials are characterized in that such materials decompose, degrade, delaminate, or dissolve to release an additive, agent, and/or functional moiety.

In some embodiments, silk fibroin-based materials are introduced in vivo.

In some embodiments, when in a compressed state, silk fibroin-based materials as described herein are implanted in vivo. In some embodiments, such silk fibroin-based materials are introduced into an implantation device (e.g. a needle or cannula) when such materials are in a compressed state. In some embodiments, when exposed to a trigger and/or external stimulus, implanted silk fibroin-based materials are further characterized in that they swell to fill a space in the body. In some embodiments, silk-fibroin based materials with shape memory characteristics allow them to be compressed to fit through an insertion device and subsequently expanded by means of a trigger, such as a physiological trigger back into the original shape; while supporting tissue regeneration requirements.

In some embodiments, provided silk fibroin-based materials permit cellular infiltration. In some embodiments, silk fibroin-based materials are characterized in that they are infiltrated when present in vivo.

In some embodiments, silk fibroin-based materials decompose, degrade, delaminate, or dissolve when present in vivo. In some embodiments, silk fibroin-based materials decompose, degrade, delaminate, or dissolve without significant immunological response when present in vivo. In some embodiments, silk fibroin-based materials exhibit predictable degradation kinetics. In some embodiments, silk fibroin-based materials are resorbed in vivo and replaced with natural tissues.

In some embodiments, the present disclosure provides methods of making silk fibroin-based materials as provided herein.

In some embodiments, methods of providing, preparing, and/or manufacturing silk fibroin-based materials of the present disclosure include providing a silk solution. In some embodiments, methods of providing, preparing, and/or manufacturing silk fibroin-based materials of the present disclosure comprises boiling silk in $Na_2CO_3$ for between about 5 minutes and about 90 minutes. In some embodiments, silk fibers were solubilized in lithium bromide (LiBr) and then dialyzed against water to yield a polymer molecular weight of between about 3.5 kDa and about 400 kDa.

In some embodiments, methods of providing, preparing, and/or manufacturing silk fibroin-based materials of the present disclosure include providing a silk solution with a silk concentration between about 0.1% and 50%.

In some embodiments, methods of providing, preparing, and/or manufacturing silk fibroin-based materials of the present disclosure include providing a silk fibroin solution comprised of modified silk. In some embodiments, methods of providing, preparing, and/or manufacturing silk fibroin-based materials of the present disclosure include modifying a silk fibroin solution or modifying a silk fibroin-based material.

In some embodiments, methods of modifying a silk fibroin solution or modifying a silk fibroin-based material include adding, mixing, and/or applying an additive, agent, and/or functional moiety to a silk solution or a silk fibroin-based material. In some embodiments, methods of modifying a silk fibroin solution or modifying a silk fibroin-based material include reacting an additive, agent, and/or functional moiety with a silk solution or a silk fibroin-based material.

In some particular embodiments, methods of providing, preparing, and/or manufacturing silk fibroin-based materials of the present disclosure include providing a silk fibroin solution (e.g. an aqueous silk fibroin solution) or a silk fibroin-based material and modifying amino acid residues by a sulfonic acid modification. In some particular embodiments, methods of providing, preparing, and/or manufacturing silk fibroin-based materials of the present disclosure includes providing an silk fibroin solution or a silk fibroin-based material and modifying by a poly-lysine modification. In some particular embodiments, methods of providing, preparing, and/or manufacturing silk fibroin-based materials of the present disclosure includes providing a silk fibroin solution or a silk fibroin-based material and modifying tyrosine residues via a diazonium coupling reaction. In some particular embodiments, methods of providing, preparing, and/or manufacturing silk fibroin-based materials of the present disclosure includes providing a silk fibroin solution or a silk fibroin-based material and modifying with 4-(heptyloxy)aniline. In some particular embodiments, methods of providing, preparing, and/or manufacturing silk fibroin-based materials of the present disclosure includes providing a silk fibroin solution or a silk fibroin-based material and modifying with 4'-aminoacetophenone.

In some embodiments, methods of providing, preparing, and/or manufacturing silk fibroin-based materials of the present disclosure include preparing and/or providing a silk fibroin solution comprising between about 1% and about 75% modified silk (e.g. in some embodiments, tyrosine residues that are covalently modified by an addition of one or more pendant groups). In some embodiments, preparing and/or providing such a solution comprises mixing a silk solution comprised of modified silk with an unmodified silk solution.

In some embodiments, methods of providing, preparing, and/or manufacturing silk fibroin-based materials of the present disclosure include mixing a silk solution with a plasticizer. In some embodiments, mixing a silk solution and a plasticizer yields a silk solution having a weight ratio of plasticizer to silk between about 5% and about 80%.

In some embodiments, methods of providing, preparing, and/or manufacturing silk fibroin-based materials of the present disclosure include lyophilizing a silk fibroin solution as described herein.

In some embodiments, methods of providing, preparing, and/or manufacturing silk fibroin-based materials of the present disclosure include providing a container for maintaining a silk fibroin solution during lyophilization. In some embodiments, such a container possesses an optimized geometry such that a volume of silk solution uniformly freezes during lyophilization. In some embodiments, such a container is characterized in that it is thermally conductive. In some embodiments, a thermally conductive container is characterized by a thermal conductivity that is equivalent to or greater than: 167 W/m-K (metric) or 1160 BTU-in/hr-ft$^2$-° F. (English). In some embodiments, for example, a container is made of: alumina, aluminum, beryllia, brass, copper, gold, iron, silver, tungsten, and/or zinc.

In some embodiments, methods of providing, preparing, and/or manufacturing silk fibroin-based materials of the present disclosure includes freezing or lyophilizing an aqueous silk solution at a target temperature. In some embodiments, a target temperature is at least below the glass transition temperature of silk. In some embodiments, a target temperature is between about −20° C. and about −50° C.

In some embodiments, freezing or lyophilizing an aqueous silk solution includes controlled lyophilizing over a period and/or slow freezing.

In some embodiments, controlled lyophilizing over a period and/or slow freezing a silk solution includes cooling a silk fibroin solution at a rate (° C./min). In some embodiments, controlled lyophilizing over a period and/or slow freezing a silk fibroin solution occurs at a slower rate of cooling relative to a rapid freezing, which is defined as directly placing a sample container in a freezer that is already at a target temperature. In some embodiments, provided methods comprise controlled lyophilizing over a period and/or slow freezing at a rate so that silk solutions reach temperature with a period between about 5 hours and about 25 hours.

In some embodiments, methods of providing, preparing, and/or manufacturing silk fibroin-based materials of the present disclosure includes controlled lyophilizing over a period and/or slow freezing a silk fibroin solution at a rate between about −10° C./min to about −0.001° C./min. In some embodiments, methods of providing, preparing, and/or manufacturing silk fibroin-based materials of the present disclosure includes controlled lyophilizing over a period and/or slow freezing a silk fibroin solution at a rate between about −0.1° C./min to about −0.01° C./min.

In some embodiments, each different rate produces a silk fibroin-based material having a slightly different structure with respect to pore size, pore shape, protein secondary structure and/or combinations thereof. Without wishing to be bound to a theory, controlled lyophilizing over a period and/or slow freezing affects porosity and swelling kinetics of silk fibroin-based material.

In some embodiments, methods of providing, preparing, and/or manufacturing silk fibroin-based materials of the present disclosure includes controlled lyophilizing over a period and/or slow freezing a silk fibroin solution at a fixed rate, a variable rate or a temperature profile including combinations thereof.

In some embodiments, methods of providing, preparing, and/or manufacturing silk fibroin-based materials of the present disclosure includes treating silk fibroin-based materials with methanol. In some embodiments, a treating step comprises immersing provided silk fibroin-based materials in methanol. In some embodiments, treating silk fibroin-based materials with methanol results in a water insoluble silk fibroin-based material.

In some embodiments, methods of the present disclosure comprise compressing provided silk fibroin-based materials to a compressed state and/or a deformed shape. In some embodiments, methods of the present disclosure comprise swelling provided silk fibroin-based materials to an expanded state.

In some embodiments, methods of the present disclosure comprise triggering recovery of a silk fibroin-based material from a compressed state, so that a silk fibroin-based material substantially returns to its original shape. In some embodiments, methods of the present disclosure include triggering recovery, so that a material substantially returns to its original volume.

In some embodiments, methods of the present disclosure include triggering recovery, so that a material substantially returns to its original volume. In some embodiments, methods of the present disclosure include triggering recovery of a compressed silk fibroin-based material so that it rapidly swells and expands between about two fold to about 50 fold of the compressed volume. In some embodiments, methods of the present disclosure include triggering recovery of a compressed silk fibroin-based material so that it rapidly swells and expands by mass to at least about 400% from that of the compressed state. In some embodiments, when exposed to a trigger and/or external stimulus, including exposure to aqueous media, silk fibroin-based materials exhibit swelling up to about 900% from that of the compressed state.

BRIEF DESCRIPTION OF THE DRAWING

The foregoing and other objects, aspects, features, and advantages of the present disclosure will become more apparent and better understood by referring to the following description taken in conjunction with the accompanying figures in which:

FIG. 3 at panel (A) shows an abbreviated list of polyol additives, separated by number of carbons per molecules, for silk foams. FIG. 3 at panel (B) shows an addition of each polyol affects the outcome of pore geometry after a lyophilization process. This may have to do with the hygroscopic nature of these polyols and their ability to sequester water molecules during freezing, resulting in larger ice crystals and thus larger pores. FIG. 3 at panel (C) shows an addition of such polyol additives. The addition shows the effect resulting in an altering of average pore size. FIG. 3 at panel (D) shows an addition of such polyol additives, each polyol affects the overall stiffness of the foam, creating foams that are softer than silk only controls.

FIG. 4 at panel (A) shows a storage modulus of slow frozen foams made from 20 MB silk. Slow frozen foams were frozen at a rate of −0.05° C. until the temperature reached −50° C. FIG. 4 at panel (B) shows a storage modulus of quick frozen foams made from 20 MB silk. Quick frozen foams were set on a shelf pre-set to −50° C. Quick frozen foams were significantly stiffer than slow frozen foams, and there was no significant difference between the storage modulus of foams containing different amounts of glycerol.

FIG. 6 at panel (A) shows a typical bilayer that results from freezing foams in polystyrene molds. This bilayer results in two regions: rounded, homogenous pores on top and random, brittle pores on the bottom which must be cut and discarded. FIG. 6 at panel (B) shows foams cast in aluminum molds, which do not produce a bilayer, but instead a consistent rounded pore morphology throughout the foam. Images are oriented with the bottom of the foam facing towards the bottom of the image. The presence of a bilayer creates unpredictable pore morphology in the top layer of foams, causing inconsistent mechanical properties and pore morphology.

FIG. 8 at panel (A) shows volumetric swelling data for silk/glycerol foams. Volumetric expansion was determined by comparing the volume of foams at 90% compression to the volume after recovery in PBS. Silk only (0% glycerol) showed only a 2× increase in volume immediately after compression, while 30% glycerol foams showed approximately a 6× increase in volume. FIG. 8 at panel (B) shows compressive modulus of silk foams. Silk/glycerol foams show a range of different mechanical moduli between 35-810 kPa depending on the glycerol content in the foams, however, other silk/glycerol formulations with no methanol treatment produced foams with elastic moduli as low as 7.5 kPa.

FIG. 9 at panel (A) shows silk only foams. FIG. 9 at panel (B) shows silk-glycerol foams. Both silk only and silk-glycerol foams show minimal inflammation response. Cell infiltration however is far greater in glycerol foams compared to silk only. This resulted in faster degradation of the silk-glycerol foams.

FIG. 15 at panel (A) shows stress-strain curves for 10 mE silk sponges; silk only with methanol wash post-treatment, silk with 40% w/w glycerol with no post-treatment, and silk with 40% w/w glycerol with methanol wash post-treatment. FIG. 15 at panel (B) shows evaluation of hysteresis by calculating the ratio of the area under the curve for the load cycle vs. the unload cycle. Smaller values indicate less hysteresis during compression cycles. FIG. 15 at panel (C) shows compressive modulus of silk sponges with varying extraction times and glycerol concentrations. The left panel sponges were post-treated with a methanol wash, the right panel sponges were not post-treated. FIG. 15 at panel (D) shows recovery of sponges after 80% compressive strain. The left panel sponges were post-treated with a methanol wash, the right panel sponges were not post-treated.

FIG. 17 at panel (A) shows compressive modulus of 10 mE silk sponges with varying concentration of modified tyrosine residues and glycerol concentrations. FIG. 17 at panel (B) Peak compressive stress at 80% axial strain.

FIG. 20 at panel (A) shows silk-glycerol sponges analyzed for secondary structure elements before methanol treatment (Pre-MeOH Wash). FIG. 20 at panel (B) shows silk-glycerol sponges analyzed for secondary structure elements after treatment in methanol (Post-MeOH Wash). FIG. 20 at panels (A) and (B) show sponges containing varying amounts of glycerol. FIG. 20 at panels (A) and (B) include blended ratios: (a) Silk only; (b) 1 w/w % glycerol; (c) 5 w/w % glycerol; (d) 10 w/w % glycerol; (e) 15 w/w % glycerol; (f) 20 w/w % glycerol; (g) 30 w/w % glycerol; (h) 40 w/w % glycerol. FIG. 20 at panel (C) shows silk-glycerol sponges analyzed for secondary structure elements, in terms of relative concentration, before methanol treatment (Pre-MeOH Wash). FIG. 20 at panel (D) shows silk-glycerol sponges analyzed for secondary structure elements, in terms of relative concentration, after treatment in methanol (Post-MeOH Wash). FIG. 20 at panels (C) and (D) show sponges containing varying amounts of glycerol. FIG. 20 at panels (C) and (D) further shows silk-glycerol sponges containing silk processed through varying amounts of extraction time (10 mE, 30 mE and 60 mE). FIG. 20 at panels (C) and (D) show relative concentration of: (i) beta sheet; (ii) alpha helix; (iii) random coil; and (iv) beta-turns.

FIG. 21 at panel (A) shows diazonium modified silk sponges analyzed for secondary structure elements. FIG. 21 at panel (A) show sponges containing varying amounts of glycerol and sulfonic acid azosilk. FIG. 21 at panel (A) include blended ratios: (a) silk only; (b) 30 w/w % glycerol; (c) 10% SAA; (d) 10% SAA, 30 w/w % glycerol; (e) 30% SAA; (f) 30% SAA, 30 w/w % glycerol; (g) 60% SAA; (h) 60% SAA, 30 w/w % glycerol. FIG. 21 at panel (B) shows sponges containing varying amounts of glycerol. FIG. 21 at panel (B) further shows silk-glycerol sponges containing varying amounts of glycerol (0% glycerol and 30% glycerol). FIG. 21 at panel (B) shows relative concentration of: (i) beta sheet; (ii) alpha helix; (iii) random coil; and (iv) beta-turns.

FIG. 22 at panel (A) shows macroscopic presentation of unmodified silk only sponge (left) and diazonium modified sponge (right). FIG. 22 at panel (B) shows scanning electron microscopy showing the inner material morphology for sponges containing glycerol and modified tyrosine. Glycerol imparts a rounded pore shape in silk materials, and increasing diazonium modification elicits formation of fibrillar structures. (Scale bars are 100 μm for main image, 200 μm for inset). FIG. 22 at panels (C) and (D) show pore size distribution by mercury intrusion porosimetry. The addition of 30% w/w glycerol narrows and decreases the size distribution for sponges derived from longer extraction times. FIG. 22 at panels (E and F) show pore size distribution for diazonium modified sponges. The swelling resulting from tyrosine modification causes a shift towards larger pore diameters.

FIG. 23 at panel (A) shows histological examination shows that cell infiltration in enhanced in glycerol containing sponges compared to silk only controls, where cell infiltration is limited to the perimeter of the material. Macroscopic evaluation of sponge volume revealed that the addition of glycerol to silk sponges increases the in vivo degradation rate. FIG. 23 at panel (B) shows dotted circles are to allow visual comparison of silk only (white) vs. 30% w/w glycerol (red) groups at 2 and 12 week time points. FIG. 23 at panel (C) shows a comparison of sponge diameter groups of silk only vs. 30% w/w glycerol at 2, 4, 8, and 12 week time points.

DEFINITIONS

Figure 1:
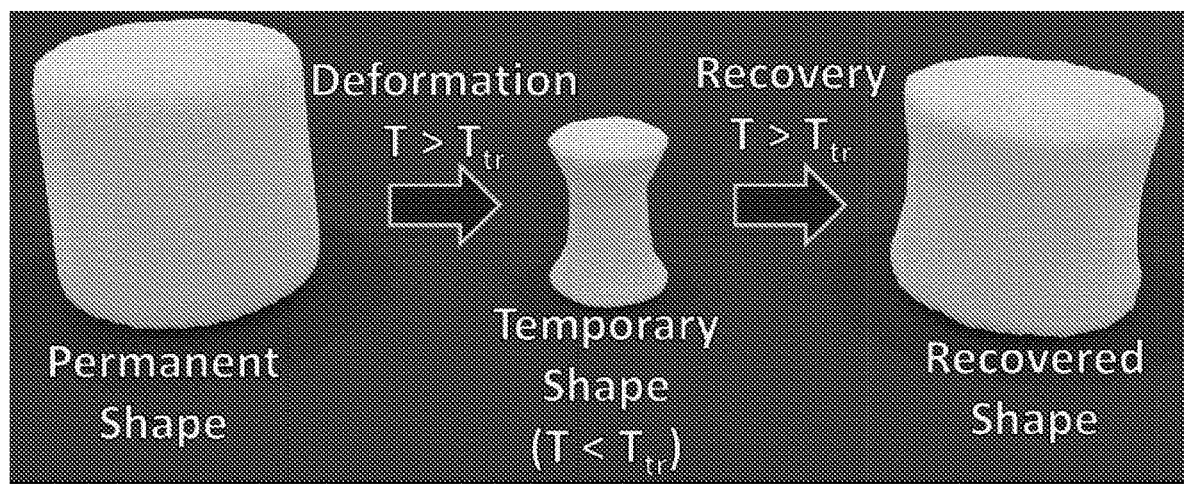
FIG. 1 shows a thermosensitive shape memory polymer (SMP) foam undergoing thermally induced deformation. The material's permanent shape can be deformed by heating above its thermal transition temperature (Ttr) and applying a compressive stress. Upon cooling below the thermal transition temperature, the material can be locked into its temporary shape. Heating again to above the thermal transition temperature can allow the material to recover back to its original shape. Materials have an initial set geometry (the permanent shape) which can be deformed by an external force under certain trigger conditions (e.g. at or beyond a transition temperature, in the presence of a solvent, etc.). After deformation, the material exists in a temporary shape. In this example, the material has been compressed. Triggered recovery is initiated once the initial stimuli (temperature, solvent) have been recapitulated. The material regains its original shape or volume after this stimulus that results in the recovered shape.

In order for the present disclosure to be more readily understood, certain terms are first defined below. Additional definitions for the following terms and other terms are set forth throughout the specification.

In this application, unless otherwise clear from context, the term "a" may be understood to mean "at least one." As used in this application, the term "or" may be understood to mean "and/or." In this application, the terms "comprising" and "including" may be understood to encompass itemized components or steps whether presented by themselves or together with one or more additional components or steps. Unless otherwise stated, the terms "about" and "approximately" may be understood to permit standard variation as would be understood by those of ordinary skill in the art. Where ranges are provided herein, the endpoints are included. As used in this application, the term "comprise" and variations of the term, such as "comprising" and "comprises," are not intended to exclude other additives, components, integers or steps.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration": As used herein, the term "administration" refers to the administration of a composition to a subject. Administration may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

"Affinity": As is known in the art, "affinity" is a measure of the tightness with a particular ligand binds to its partner. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

"Agent": As used herein, the term "agent" may refer to a compound or entity of any chemical class including, for example, polypeptides, nucleic acids, saccharides, lipids, small molecules, metals, or combinations thereof. As will be clear from context, in some embodiments, an agent can be or comprise a cell or organism, or a fraction, extract, or component thereof. In some embodiments, an agent is agent is or comprises a natural product in that it is found in and/or is obtained from nature. In some embodiments, an agent is or comprises one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized in accordance with the present disclosure include small molecules, antibodies, antibody fragments, aptamers, siRNAs, shRNAs, DNA/RNA hybrids, antisense oligonucleotides, ribozymes, peptides, peptide mimetics, small molecules, etc. In some embodiments, an agent is or comprises a polymer. In some embodiments, an agent is not a polymer and/or is substantially free of any polymer. In some embodiments, an agent contains at least one polymeric moiety. In some embodiments, an agent lacks or is substantially free of any polymeric moiety.

"Analog": As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance "Amino acid": As used herein, the term "amino acid," in its broadest sense, refers to any compound and/or substance that can be incorporated into a polypeptide chain, e.g., through formation of one or more peptide bonds. In some embodiments, an amino acid has the general structure H2N—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure herein. For example, in some embodiments, an amino acid may be modified by methylation, amidation, acetylation, and/or substitution as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" is used to refer to a free amino acid; in some embodiments it is used to refer to an amino acid residue of a polypeptide.

"Antibody": As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. Amino acid sequence comparisons among antibody polypeptide chains have defined two light chain (κ and λ) classes, several heavy chain (e.g., μ, γ, α, ε, δ) classes, and certain heavy chain subclasses (α1, α2, γ1, γ2, γ3, and γ4). Antibody classes (IgA [including IgA1, IgA2], IgD, IgE, IgG [including IgG1, IgG2, IgG3, IgG4], IgM) are defined based on the class of the utilized heavy chain sequences. For purposes of the present disclosure, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is monoclonal; in some embodiments, an antibody is monoclonal. In some embodiments, an antibody has constant region sequences that are characteristic of mouse, rabbit, primate, or human antibodies. In some embodiments, an antibody sequence elements are humanized, primatized, chimeric, etc., as is known in the art. Moreover, the term "antibody" as used herein, will be understood to encompass (unless otherwise stated or clear from context) can refer in appropriate embodiments to any of the art-known or developed constructs or formats for capturing antibody structural and functional features in alternative presentation. For example, in some embodiments, the term can refer to bi- or other multi-specific (e.g., zybodies, etc.) antibodies, Small Modular ImmunoPharmaceuticals ("SMIPs™"), single chain antibodies, cameloid antibodies, and/or antibody fragments. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc.].

"Associated" or "Associated with": As used herein, the term "associated" or "associated with" typically refers to two or more entities in physical proximity with one another, either directly or indirectly (e.g., via one or more additional entities that serve as a linking agent), to form a structure that is sufficiently stable so that the entities remain in physical proximity under relevant conditions, e.g., physiological conditions. In some embodiments, associated entities are covalently linked to one another. In some embodiments, associated entities are non-covalently linked. In some embodiments, associated entities are linked to one another by specific non-covalent interactions (i.e., by interactions between interacting ligands that discriminate between their interaction partner and other entities present in the context of use, such as, for example, streptavidin/avidin interactions, antibody/antigen interactions, etc.). Alternatively or additionally, a sufficient number of weaker non-covalent interactions can provide sufficient stability for moieties to remain associated. Exemplary non-covalent interactions include, but are not limited to, affinity interactions, metal coordination, physical adsorption, host-guest interactions, hydrophobic interactions, pi stacking interactions, hydrogen bonding interactions, van der Waals interactions, magnetic interactions, electrostatic interactions, dipole-dipole interactions, etc.

"Binding": It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

"Binding agent": In general, the term "binding agent" is used herein to refer to any entity that binds to a target of interest as described herein. In many embodiments, a binding agent of interest is one that binds specifically with its target in that it discriminates its target from other potential binding partners in a particular interaction contect. In general, a binding agent may be or comprise an entity of any chemical class (e.g., polymer, non-polymer, small molecule, polypeptide, carbohydrate, lipid, nucleic acid, etc). In some embodiments, a binding agent is a single chemical entity. In some embodiments, a binding agent is a complex of two or more discrete chemical entities associated with one another under relevant conditions by non-covalent interactions. For example, those skilled in the art will appreciate that in some embodiments, a binding agent may comprise a "generic" binding moiety (e.g., one of biotin/avidin/streptaviding and/or a class-specific antibody) and a "specific" binding moiety (e.g., an antibody or aptamers with a particular molecular target) that is linked to the partner of the generic biding moiety. In some embodiments, such an approach can permit modular assembly of multiple binding agents through linkage of different specific binding moieties with the same generic binding poiety partner. In some embodiments, binding agents are or comprise polypeptides (including, e.g., antibodies or antibody fragments). In some embodiments, binding agents are or comprise small molecules. In some embodiments, binding agents are or comprise nucleic acids. In some embodiments, binding agents are aptamers. In some embodiments, binding agents are polymers; in some embodiments, binding agents are not polymers. In some embodiments, binding agents are non-polymeric in that they lack polymeric moieties. In some embodiments, binding agents are or comprise carbohydrates. In some embodiments, binding agents are or comprise lectins. In some embodiments, binding agents are or comprise peptidomimetics. In some embodiments, binding agents are or comprise scaffold proteins. In some embodiments, binding agents are or comprise mimeotopes. In some embodiments, binding agents are or comprise stapled peptides. In certain embodiments, binding agents are or comprise nucleic acids, such as DNA or RNA.

"Biocompatible": The term "biocompatible", as used herein, refers to materials that do not cause significant harm to living tissue when placed in contact with such tissue, e.g., in vivo. In certain embodiments, materials are "biocompatible" if they are not toxic to cells. In certain embodiments, materials are "biocompatible" if their addition to cells in vitro results in less than or equal to 20% cell death, and/or their administration in vivo does not induce significant inflammation or other such adverse effects.

"Biodegradable": As used herein, the term "biodegradable" refers to materials that, when introduced into cells, are broken down (e.g., by cellular machinery, such as by enzymatic degradation, by hydrolysis, and/or by combinations thereof) into components that cells can either reuse or dispose of without significant toxic effects on the cells. In certain embodiments, components generated by breakdown of a biodegradable material are biocompatible and therefore do not induce significant inflammation and/or other adverse effects in vivo. In some embodiments, biodegradable polymer materials break down into their component monomers. In some embodiments, breakdown of biodegradable materials (including, for example, biodegradable polymer materials) involves hydrolysis of ester bonds. Alternatively or additionally, in some embodiments, breakdown of biodegradable materials (including, for example, biodegradable polymer materials) involves cleavage of urethane linkages. Exemplary biodegradable polymers include, for example, polymers of hydroxy acids such as lactic acid and glycolic acid, including but not limited to poly(hydroxyl acids), poly(lactic acid)(PLA), poly(glycolic acid)(PGA), poly(lactic-co-glycolic acid)(PLGA), and copolymers with PEG, polyanhydrides, poly(ortho)esters, polyesters, polyurethanes, poly(butyric acid), poly(valeric acid), poly(caprolactone), poly(hydroxyalkanoates, poly(lactide-co-caprolactone), blends and copolymers thereof. Many naturally occurring polymers are also biodegradable, including, for example, proteins such as albumin, collagen, gelatin and prolamines, for example, zein, and polysaccharides such as alginate, cellulose derivatives and polyhydroxyalkanoates, for example, polyhydroxybutyrate blends and copolymers thereof. Those of ordinary skill in the art will appreciate or be able to determine when such polymers are biocompatible and/or biodegradable derivatives thereof (e.g., related to a parent polymer by substantially identical structure that differs only in substitution or addition of particular chemical groups as is known in the art).

"Biologically active": As used herein, the phrase "biologically active" refers to a substance that has activity in a biological system (e.g., in a cell (e.g., isolated, in culture, in a tissue, in an organism), in a cell culture, in a tissue, in an organism, etc.). For instance, a substance that, when administered to an organism, has a biological effect on that organism, is considered to be biologically active. It will be appreciated by those skilled in the art that often only a portion or fragment of a biologically active substance is required (e.g., is necessary and sufficient) for the activity to be present; in such circumstances, that portion or fragment is considered to be a "biologically active" portion or fragment.

"Characteristic portion": As used herein, the term "characteristic portion" is used, in the broadest sense, to refer to a portion of a substance whose presence (or absence) correlates with presence (or absence) of a particular feature, attribute, or activity of the substance. In some embodiments, a characteristic portion of a substance is a portion that is found in the substance and in related substances that share the particular feature, attribute or activity, but not in those that do not share the particular feature, attribute or activity. In certain embodiments, a characteristic portion shares at least one functional characteristic with the intact substance. For example, in some embodiments, a "characteristic portion" of a protein or polypeptide is one that contains a continuous stretch of amino acids, or a collection of continuous stretches of amino acids, that together are characteristic of a protein or polypeptide. In some embodiments, each such continuous stretch generally contains at least 2, 5, 10, 15, 20, 50, or more amino acids. In general, a characteristic portion of a substance (e.g., of a protein, antibody, etc.) is one that, in addition to the sequence and/or structural identity specified above, shares at least one functional characteristic with the relevant intact substance. In some embodiments, a characteristic portion may be biologically active.

"Comparable": The term "comparable", as used herein, refers to two or more agents, entities, situations, sets of conditions, etc. that may not be identical to one another but that are sufficiently similar to permit comparison therebetween so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

"Conjugated": As used herein, the terms "conjugated," "linked," "attached," and "associated with," when used with respect to two or more moieties, means that the moieties are physically associated or connected with one another, either directly or via one or more additional moieties that serves as a linking agent, to form a structure that is sufficiently stable so that the moieties remain physically associated under the conditions in which structure is used, e.g., physiological conditions. Typically the moieties are attached either by one or more covalent bonds or by a mechanism that involves specific binding. Alternately, a sufficient number of weaker interactions can provide sufficient stability for moieties to remain physically associated.

"Corresponding to": As used herein, the term "corresponding to" is often used to designate the position/identity of a residue in a polymer, such as an amino acid residue in a polypeptide or a nucleotide residue in a nucleic acid. Those of ordinary skill will appreciate that, for purposes of simplicity, residues in such a polymer are often designated using a canonical numbering system based on a reference related polymer, so that a residue in a first polymer "corresponding to" a residue at position 190 in the reference polymer, for example, need not actually be the 190th residue in the first polymer but rather corresponds to the residue found at the 190th position in the reference polymer; those of ordinary skill in the art readily appreciate how to identify "corresponding" amino acids, including through use of one or more commercially-available algorithms specifically designed for polymer sequence comparisons.

"Detection entity": The term "detection entity" as used herein refers to any element, molecule, functional group, compound, fragment or moiety that is detectable. In some embodiments, a detection entity is provided or utilized alone. In some embodiments, a detection entity is provided and/or utilized in association with (e.g., joined to) another agent. Examples of detection entities include, but are not limited to: various ligands, radionuclides (e.g., $^{3}$H, $^{14}$C, $^{18}$F, $^{19}$F, $^{32}$P, $^{35}$S, $^{135}$I, $^{125}$I, $^{123}$I, $^{64}$Cu, $^{187}$Re, $^{111}$In, $^{90}$Y, $^{99m}$Tc, $^{17}$Lu, $^{89}$Zr etc.) fluorescent dyes (for specific exemplary fluorescent dyes, see below), chemiluminescent agents (such as, for example, acridinum esters, stabilized dioxetanes, and the like), bioluminescent agents, spectrally resolvable inorganic fluorescent semiconductors nanocrystals (i.e., quantum dots), metal nanoparticles (e.g., gold, silver, copper, platinum, etc.) nanoclusters, paramagnetic metal ions, enzymes (for specific examples of enzymes, see below), colorimetric labels (such as, for example, dyes, colloidal gold, and the like), biotin, dioxigenin, haptens, and proteins for which antisera or monoclonal antibodies are available.

"Determine": Many methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

"Dosage form": As used herein, the term "dosage form" refers to a physically discrete unit of a therapeutic agent for administration to a subject. Each unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen).

"Encapsulated": The term "encapsulated" is used herein to refer to substances that are completely surrounded by another material.

"Functional": As used herein, a "functional" biological molecule is a biological molecule in a form in which it exhibits a property and/or activity by which it is characterized. A biological molecule may have two functions (i.e., bi-functional) or many functions (i.e., multifunctional).

"Graft rejection": The term "graft rejection" as used herein, refers to rejection of tissue transplanted from a donor individual to a recipient individual. In some embodiments, graft rejection refers to an allograft rejection, wherein the donor individual and recipient individual are of the same species. Typically, allograft rejection occurs when the donor tissue carries an alloantigen against which the recipient immune system mounts a rejection response.

"High Molecular Weight Polymer": As used herein, the term "high molecular weight polymer" refers to polymers and/or polymer solutions comprised of polymers (e.g., protein polymers, such as silk) having molecular weights of at least about 200 kDa, and wherein no more than 30% of the silk fibroin has a molecular weight of less than 100 kDa. In some embodiments, high molecular weight polymers and/or polymer solutions have an average molecular weight of at least about 100 kDa or more, including, e.g., at least about 150 kDa, at least about 200 kDa, at least about 250 kDa, at least about 300 kDa, at least about 350 kDa or more. In some embodiments, high molecular weight polymers have a molecular weight distribution, no more than 50%, for example, including, no more than 40%, no more than 30%, no more than 20%, no more than 10%, of the silk fibroin can have a molecular weight of less than 150 kDa, or less than 125 kDa, or less than 100 kDa.

"Hydrolytically degradable": As used herein, the term "hydrolytically degradable" is used to refer to materials that degrade by hydrolytic cleavage. In some embodiments, hydrolytically degradable materials degrade in water. In some embodiments, hydrolytically degradable materials degrade in water in the absence of any other agents or materials. In some embodiments, hydrolytically degradable materials degrade completely by hydrolytic cleavage, e.g., in water. By contrast, the term "non-hydrolytically degradable" typically refers to materials that do not fully degrade by hydrolytic cleavage and/or in the presence of water (e.g., in the sole presence of water).

"Hydrophilic": As used herein, the term "hydrophilic" and/or "polar" refers to a tendency to mix with, or dissolve easily in, water.

"Hydrophobic": As used herein, the term "hydrophobic" and/or "non-polar", refers to a tendency to repel, not combine with, or an inability to dissolve easily in, water.

"Identity": As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0). In some exemplary embodiments, nucleic acid sequence comparisons made with the ALIGN program use a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

"Low Molecular Weight Polymer": As used herein, the term "low molecular weight polymer" refers to polymers and/or polymer solutions, such as silk, comprised of polymers (e.g., protein polymers) having molecular weights within the range of about 20 kDa-about 400 kDa. In some embodiments, low molecular weight polymers (e.g., protein polymers) have molecular weights within a range between a lower bound (e.g., about 20 kDa, about 30 kDa, about 40 kDa, about 50 kDa, about 60 kDa, or more) and an upper bound (e.g., about 400 kDa, about 375 kDa, about 350 kDa, about 325 kDa, about 300 kDa, or less). In some embodiments, low molecular weight polymers (e.g., protein polymers such as silk) are substantially free of, polymers having a molecular weight above about 400 kD. In some embodiments, the highest molecular weight polymers in provided materials are less than about 300-about 400 kD (e.g., less than about 400 kD, less than about 375 kD, less than about 350 kD, less than about 325 kD, less than about 300 kD, etc). In some embodiments, a low molecular weight polymer and/or polymer solution can comprise a population of polymer fragments having a range of molecular weights, characterized in that: no more than 15% of the total moles of polymer fragments in the population has a molecular weight exceeding 200 kDa, and at least 50% of the total moles of the silk fibroin fragments in the population has a molecular weight within a specified range, wherein the specified range is between about 3.5 kDa and about 120 kDa or between about 5 kDa and about 125 kDa.

"Marker": A marker, as used herein, refers to an entity or moiety whose presence or level is a characteristic of a particular state or event. In some embodiments, presence or level of a particular marker may be characteristic of presence or stage of a disease, disorder, or condition. To give but one example, in some embodiments, the term refers to a gene expression product that is characteristic of a particular tumor, tumor subclass, stage of tumor, etc. Alternatively or additionally, in some embodiments, a presence or level of a particular marker correlates with activity (or activity level) of a particular signaling pathway, for example that may be characteristic of a particular class of tumors. The statistical significance of the presence or absence of a marker may vary depending upon the particular marker. In some embodiments, detection of a marker is highly specific in that it reflects a high probability that the tumor is of a particular subclass. Such specificity may come at the cost of sensitivity (i.e., a negative result may occur even if the tumor is a tumor that would be expected to express the marker). Conversely, markers with a high degree of sensitivity may be less specific that those with lower sensitivity. According to the present disclosure a useful marker need not distinguish tumors of a particular subclass with 100% accuracy.

"Modulator": The term "modulator" is used to refer to an entity whose presence or level in a system in which an activity of interest is observed correlates with a change in level and/or nature of that activity as compared with that observed under otherwise comparable conditions when the modulator is absent. In some embodiments, a modulator is an activator, in that activity is increased in its presence as compared with that observed under otherwise comparable conditions when the modulator is absent. In some embodiments, a modulator is an antagonist or inhibitor, in that activity is reduced in its presence as compared with otherwise comparable conditions when the modulator is absent. In some embodiments, a modulator interacts directly with a target entity whose activity is of interest. In some embodiments, a modulator interacts indirectly (i.e., directly with an intermediate agent that interacts with the target entity) with a target entity whose activity is of interest. In some embodiments, a modulator affects level of a target entity of interest; alternatively or additionally, in some embodiments, a modulator affects activity of a target entity of interest without affecting level of the target entity. In some embodiments, a modulator affects both level and activity of a target entity of interest, so that an observed difference in activity is not entirely explained by or commensurate with an observed difference in level.

"Nanoparticle": As used herein, the term "nanoparticle" refers to a particle having a diameter of less than 1000 nanometers (nm). In some embodiments, a nanoparticle has a diameter of less than 300 nm, as defined by the National Science Foundation. In some embodiments, a nanoparticle has a diameter of less than 100 nm as defined by the National Institutes of Health. In some embodiments, nanoparticles are micelles in that they comprise an enclosed compartment, separated from the bulk solution by a micellar membrane, typically comprised of amphiphilic entities which surround and enclose a space or compartment (e.g., to define a lumen).

In some embodiments, a micellar membrane is comprised of at least one polymer, such as for example a biocompatible and/or biodegradable polymer.

"Nanoparticle composition": As used herein, the term "nanoparticle composition" refers to a composition that contains at least one nanoparticle and at least one additional agent or ingredient. In some embodiments, a nanoparticle composition contains a substantially uniform collection of nanoparticles as described herein.

"Nucleic acid": As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present disclosure. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, 4, 5, 6, 7, 8, 9, 10, or more residues. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present disclosure is specifically directed to "unmodified nucleic acids," meaning nucleic acids (e.g., polynucleotides and residues, including nucleotides and/or nucleosides) that have not been chemically modified in order to facilitate or achieve delivery.

"Pharmaceutical composition": As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

"Physiological conditions": The phrase "physiological conditions", as used herein, relates to the range of chemical (e.g., pH, ionic strength) and biochemical (e.g., enzyme concentrations) conditions likely to be encountered in the intracellular and extracellular fluids of tissues. For most tissues, the physiological pH ranges from about 6.8 to about 8.0 and a temperature range of about 20-40 degrees Celsius, about 25-40° C., about 30-40° C., about 35-40° C., about 37° C., atmospheric pressure of about 1. In some embodiments, physiological conditions utilize or include an aqueous environment (e.g., water, saline, Ringers solution, or other buffered solution); in some such embodiments, the aqueous environment is or comprises a phosphate buffered solution (e.g., phosphate-buffered saline).

"Polypeptide": The term "polypeptide", as used herein, generally has its art-recognized meaning of a polymer of at least three amino acids, linked to one another by peptide bonds. In some embodiments, the term is used to refer to specific functional classes of polypeptides. For each such class, the present specification provides several examples of amino acid sequences of known exemplary polypeptides within the class; in some embodiments, such known polypeptides are reference polypeptides for the class. In such embodiments, the term "polypeptide" refers to any member of the class that shows significant sequence homology or identity with a relevant reference polypeptide. In many embodiments, such member also shares significant activity with the reference polypeptide. Alternatively or additionally, in many embodiments, such member also shares a particular characteristic sequence element with the reference polypeptide (and/or with other polypeptides within the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (i.e., a conserved region that may in some embodiments may be or comprise a characteristic sequence element) that shows very high sequence identity, often greater than 90% or even 95%, 96%, 97%, 98%, or 99%. Such a conserved region usually encompasses at least 3-4 and often up to 20 or more amino acids;

in some embodiments, a conserved region encompasses at least one stretch of at least 2, 3, 4, 5, 6, 7, 8, 9, 10, 11, 12, 13, 14, 15 or more contiguous amino acids. In some embodiments, a useful polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide. In some embodiments, a polypeptide may comprise natural amino acids, non-natural amino acids, or both. In some embodiments, a polypeptide may comprise only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups, e.g., modifying or attached to one or more amino acid side chains, and/or at the polypeptide's N-terminus, the polypeptide's C-terminus, or both. In some embodiments, a polypeptide may be cyclic. In some embodiments, a polypeptide is not cyclic. In some embodiments, a polypeptide is linear.

"Polysaccharide": The term "polysaccharide" refers to a polymer of sugars. Typically, a polysaccharide comprises at least three sugars. In some embodiments, a polypeptide comprises natural sugars (e.g., glucose, fructose, galactose, mannose, arabinose, ribose, and xylose); alternatively or additionally, in some embodiments, a polypeptide comprises one or more non-natural amino acids (e.g. modified sugars such as 2'-fluororibose, 2'-deoxyribose, and hexose).

"Porosity": The term "porosity" as used herein, refers to a measure of void spaces in a material and is a fraction of volume of voids over the total volume, as a percentage between 0 and 100%. A determination of a porosity is known to a skilled artisan using standardized techniques, for example mercury porosimetry and gas adsorption (e.g., nitrogen adsorption).

"Protein": As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids.

In some embodiments, proteins are antibodies, antibody fragments, biologically active portions thereof, and/or characteristic portions thereof.

"Reference": The term "reference" is often used herein to describe a standard or control agent, individual, population, sample, sequence or value against which an agent, individual, population, sample, sequence or value of interest is compared. In some embodiments, a reference agent, individual, population, sample, sequence or value is tested and/or determined substantially simultaneously with the testing or determination of the agent, individual, population, sample, sequence or value of interest. In some embodiments, a reference agent, individual, population, sample, sequence or value is a historical reference, optionally embodied in a tangible medium. Typically, as would be understood by those skilled in the art, a reference agent, individual, population, sample, sequence or value is determined or characterized under conditions comparable to those utilized to determine or characterize the agent, individual, population, sample, sequence or value of interest.

"Small molecule": As used herein, the term "small molecule" is used to refer to molecules, whether naturally-occurring or artificially created (e.g., via chemical synthesis), having a relatively low molecular weight and being an organic and/or inorganic compound. Typically, a "small molecule" is monomeric and have a molecular weight of less than about 1500 g/mol. In general, a "small molecule" is a molecule that is less than about 5 kilodaltons (kD) in size. In some embodiments, a small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, a small molecule is not a polymer. In some embodiments, a small molecule does not include a polymeric moiety. In some embodiments, a small molecule is not a protein or polypeptide (e.g., is not an oligopeptide or peptide). In some embodiments, a small molecule is not a polynucleotide (e.g., is not an oligonucleotide). In some embodiments, a small molecule is not a polysaccharide. In some embodiments, a small molecule does not comprise a polysaccharide (e.g., is not a glycoprotein, proteoglycan, glycolipid, etc.). In some embodiments, a small molecule is not a lipid. In some embodiments, a small molecule is a modulating agent. In some embodiments, a small molecule is biologically active. In some embodiments, a small molecule is detectable (e.g., comprises at least one detectable moiety). In some embodiments, a small molecule is a therapeutic. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§ 330.5, 331 through 361, and 440 through 460; drugs for veterinary use listed by the FDA under 21 C.F.R. §§ 500 through 589, incorporated herein by reference, are all considered acceptable for use in accordance with the present application.

"Solution": As used herein, the term "solution" broadly refers to a homogeneous mixture composed of one phase. Typically, a solution comprises a solute or solutes dissolved in a solvent or solvents. It is characterized in that the properties of the mixture (such as concentration, temperature, and density) can be uniformly distributed through the volume. In the context of the present application, therefore, a "silk fibroin solution" refers to silk fibroin protein in a soluble form, dissolved in a solvent, such as water. In some embodiments, silk fibroin solutions may be prepared from a solid-state silk fibroin material (i.e., silk matrices), such as silk films and other scaffolds. Typically, a solid-state silk fibroin material is reconstituted with an aqueous solution, such as water and a buffer, into a silk fibroin solution. It should be noted that liquid mixtures that are not homogeneous, e.g., colloids, suspensions, emulsions, are not considered solutions.

"Stable": The term "stable," when applied to compositions herein, means that the compositions maintain one or more aspects of their physical structure and/or activity over a period of time under a designated set of conditions. In some embodiments, the period of time is at least about one hour; in some embodiments, the period of time is about 5 hours, about 10 hours, about one (1) day, about one (1) week, about two (2) weeks, about one (1) month, about two (2) months, about three (3) months, about four (4) months, about five (5) months, about six (6) months, about eight (8) months, about ten (10) months, about twelve (12) months, about twenty-four (24) months, about thirty-six (36) months, or longer. In some embodiments, the period of time is within the range of about one (1) day to about twenty-four (24) months, about two (2) weeks to about twelve (12) months, about two (2) months to about five (5) months, etc. In some embodiments, the designated conditions are ambient conditions (e.g., at room temperature and ambient pressure). In some embodiments, the designated conditions are physiologic conditions (e.g., in vivo or at about 37° C. for example in serum or in phosphate buffered saline). In some embodiments, the designated conditions are under cold storage (e.g., at or below about 4° C., −20° C., or −70° C.). In some embodiments, the designated conditions are in the dark.

"Substantially": As used herein, the term "substantially", and grammatic equivalents, refer to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result.

"Sustained release": The term "sustained release" is used herein in accordance with its art-understood meaning of release that occurs over an extended period of time. The extended period of time can be at least about 3 days, about 5 days, about 7 days, about 10 days, about 15 days, about 30 days, about 1 month, about 2 months, about 3 months, about 6 months, or even about 1 year. In some embodiments, sustained release is substantially burst-free. In some embodiments, sustained release involves steady release over the extended period of time, so that the rate of release does not vary over the extended period of time more than about 5%, about 10%, about 15%, about 20%, about 30%, about 40% or about 50%. In some embodiments, sustained release involves release with first-order kinetics. In some embodiments, sustained release involves an initial burst, followed by a period of steady release. In some embodiments, sustained release does not involve an initial burst. In some embodiments, sustained release is substantially burst-free release.

"Therapeutic agent": As used herein, the phrase "therapeutic agent" refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

"Therapeutically effective amount": As used herein, the term "therapeutically effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. It is specifically understood that particular subjects may, in fact, be "refractory" to a "therapeutically effective amount." To give but one example, a refractory subject may have a low bioavailability such that clinical efficacy is not obtainable. In some embodiments, reference to a therapeutically effective amount may be a reference to an amount as measured in one or more specific tissues (e.g., a tissue affected by the disease, disorder or condition) or fluids (e.g., blood, saliva, serum, sweart, tears, urine, etc). Those of ordinary skill in the art will appreciate that, in some embodiments, a therapeutically effective amount may be formulated and/or administered in a single dose. In some embodiments, a therapeutically effective amount may be formulated and/or administered in a plurality of doses, for example, as part of a dosing regimen.

"Treating": As used herein, the term "treating" refers to partially or completely alleviating, ameliorating, relieving, inhibiting, preventing (for at least a period of time), delaying onset of, reducing severity of, reducing frequency of and/or reducing incidence of one or more symptoms or features of a particular disease, disorder, and/or condition. In some embodiments, treatment may be administered to a subject who does not exhibit symptoms, signs, or characteristics of a disease and/or exhibits only early symptoms, signs, and/or characteristics of the disease, for example for the purpose of decreasing the risk of developing pathology associated with the disease. In some embodiments, treatment may be administered after development of one or more symptoms, signs, and/or characteristics of the disease.

"Variant": As used herein, the term "variant" refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs double, E vs Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a variant polypeptide may differ from a reference polypeptide as a result of one or more differences in amino acid sequence and/or one or more differences in chemical moieties (e.g., carbohydrates, lipids, etc.) covalently attached to the polypeptide backbone. In some embodiments, a variant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

DETAILED DESCRIPTION OF CERTAIN EMBODIMENTS

Among other things, the present disclosure provides silk fibroin-based materials and methods of preparing and using such silk fibroin-based materials. Various embodiments according to the present disclosure are described in detail herein. In particular, the present disclosure describes silk fibroin-based materials and their use in various applications, including, for example: biomaterials, biomedical devices, biosensing, controlled release applications, drug delivery, electronics, materials for tunable degradation, optics, photonics, regenerative medicine, sensors, tissue engineering applications, tissue regeneration, tissue scaffolding, and/or wound clotting.

Provided silk fibroin-based materials are characterized by unique features that provide advantages over existing shape memory materials. In some embodiments, silk fibroin-based materials of the present disclosure exhibit susceptibility to compression so that such materials are characterized in that they can adopt at least two different states, a pre-compression state and a compressed state. In some embodiments, silk fibroin-based materials of the present disclosure exhibit susceptibility to swelling so that such materials are characterized in that they can further adopt an expanded state.

In some embodiments, a compressive strain reduces a silk fibroin-based materials' volume relative to its pre-compression state volume. In some embodiments, a compressive strain deforms a silk fibroin-based materials' shape relative to its pre-compression state shape. Alternatively or additionally, in some embodiments, swelling increases a silk fibroin-based materials' volume relative to its pre-compression state volume so that its volume is substantially equivalent to or greater than its pre-compression state volume.

In some embodiments, silk fibroin-based materials are characterized in that when in a compressed state, they retain their reduced volume and/or deformed shape until exposed to a trigger and/or external stimulus. In some embodiments, when exposed to a trigger and/or external stimulus such silk fibroin-based materials will recover to a larger volume. In some embodiments, such silk fibroin-based materials substantially recover their pre-compressed volume. In some embodiments, such silk fibroin-based materials substantially recover their pre-compressed shape.

In some embodiments, when exposed to a trigger and/or external stimulus, provide silk fibroin-based materials are characterized by volumetric expansion. In some embodiments, when compressed by a compressive strain of at least about 90%, so that they are compressed to about 10% or less of their original volume, such materials are characterized in that when exposed to a trigger and/or external stimulus they substantially recover their volume and/or their shape. In some embodiments, such recovered materials substantially lack an indication of a plastic deformation. In some embodiments, when compressed by a compressive stress of up to 100 kPa, such materials are characterized in that when exposed to a trigger and/or external stimulus they recover their volume and/or their shape. In some embodiments, such recovered materials substantially lack an indication of a plastic deformation.

Shape memory polymers generally describe a class of materials that can recover from a deformed shape back to an original pre-defined shape in the presence of a stimulus. Several synthetic shape memory polymers exist, such as polyurethane, silicone, poly(lactide), poly(caprolactone) and poly(glycolide). See for example Wong Y, Kong J, Widjaja L K, Venkatraman S S. Biomedical applications of shape-memory polymers: how practically useful are they? Sci China Chem 2014; 57(4):476-89; see also Safranski D L, Smith K E, Gall K. Mechanical requirements of shape-memory polymers in biomedical devices, Polym Rev 2013; 53(1):76-91. For biomedical devices, implantable shape memory materials must be sufficiently tough and fatigue resistant for load bearing applications, exhibit a recovery force strong enough to expand in a confined space, possess controlled degradability and resorption, and be biocompatible with the surrounding tissue. See for example Hager, M. D., Bode, S., Weber, C., & Schubert, U. S., Shape memory polymers: Past, present and future developments, 49-50 *Progress in Polymer Science,* 3-33 (2015).

Synthetic materials generally have sufficient modulus and toughness when dry, but often experience loss of mechanical integrity when wet or exposed to the biological environment for long periods of time. They also need to be programmed to degrade by the addition of water soluble linkers, and biocompatibility depends on many factors such as the degradation products, location of implantation, level of fatigue and duration in the body. These materials may not always cause a biological immune response, but they may not integrate well with tissue either.

Alternatively, certain biologically derived materials can be processed to behave like SMPs. Natural materials often enjoy the benefits of being biocompatible and degradable by chemical and enzymatic processes in the body. Correia and Mano made shape memory genipin-crosslinked chitosan scaffolds that expand in the presence of water. See Correia C O, Mano J F. Chitosan scaffolds with a shape memory effect induced by hydration. J Mater Chem B 2014; 2 (21):3315-23. Crosslinking with genipin allowed the chitosan network to undergo greater swelling in water compared to non-crosslinked chitosan (up to 400% by weight). Additionally, crosslinked chitosan showed 98% recovery after 60% strain deformation, but recovery was slow and took up to 15 minutes. Bencherif et al. created methacrylated alginate scaffolds via a cryogelation process which produced shape memory gels. See Bencherif S A, Sands R W, Bhatta D, Arany P, Verbeke C S, Edwards D A, et al. Injectable preformed scaffolds with shape-memory properties, Proc Natl Acad Sci USA 2012, 109 (48):19590-5. Alginate gels could recover 92% of its original volume after 90% deformation, and could be injected through a needle for minimally invasive implantation. Furthermore, gels could be impregnated with cells and used as a cell-delivery device for therapeutic applications. Gels were implanted in vivo and recovered after 2 days. The gels appeared biocompatible in mice, and only minimal degradation was reported.

By contrast with existing synthetic or natural shape memory polymers, in some embodiments, silk fibroin-based materials containing a plasticizer exhibit rapid recovery. In some embodiments, a rapid recovery occurs within seconds. In some embodiments, a rapid recovery exhibits up to 50 times volume expansion and up to 900% expansion by mass without showing evidence of plastic deformation.

Prior to the present disclosure, freeze-dry methods focused on quickly freezing solutions in a constant temperature environment (e.g. a lab freezer or chest freezer) and allowing samples to sit at the constant temperature for several days. Rapid freezing or fast freezing is accomplished by setting the shelf temperature to the target temperature, which results in the solution freezing to the set temperature in less than an hour.

The fast freezing process causes ice crystals to grow in the solution in random shapes and sizes, creating an unpredictable array of different pore geometries.

By contrast, in some embodiments, methods of the present disclosure utilize controlled lyophilizing over a period and/or slow freezing. In some embodiments, for example samples take 5 hours, 10 hours, or 20 hours to reach a target temperature. In some embodiments, provided methods include controlled lyophilizing over a period and/or slow freezing produce silk fibroin-based materials to form a structure comprising pores. In some embodiments, such pores are characterized as being interconnected through a bulk material, substantially evenly spaced, having substantially rounded morphology, having substantially uniform pore shape, and/or a substantial absence of the ice crystals as described herein.

Prior methods utilize plastic wells for rapid freezing. Plastic does not conduct heat and when used results in a silk solution that is warmer than the set-point of the shelf. Samples that are held at a warmer than desired temperature results in inconsistencies in solution freezing. For example, plastic molds typically cause a bilayer to form where half the foam has rounded pores and half contains a heterogeneous distribution of pore sizes and geometries.

Additionally, unlike previous freeze-drying methods that utilized polystyrene well plates to mold shape memory polymers, provided methods, in some embodiments, utilize highly thermally conductive materials, such as aluminum to form provided silk fibroin-based materials. In some embodiments, provided methods include form silk fibroin-based materials that are characterized as having: round pores, an evenly spaced distribution of pores, an evenly spaced distribution of pore size, and a consistent pore morphology throughout a volume.

Without the use of a plasticizer molecule and a controlled freeze-dry process, prior foams plastically deformed when compressed. In general, plastic deformation is considered to be an unfavorable quality. Plastically deformed materials will exhibit different mechanical properties than the original shape. Such plastically deformed materials for example are unable to fill a void space in the body, do not allow cellular infiltration, and/or do not permit predictable degradation kinetics in vivo.

By contrast, in some embodiments, present methods and silk fibroin-based materials formed therefrom do not show evidence of plastic deformation following compression.

Furthermore and unlike prior shape memory polymers, in some embodiments, silk fibroin-based materials of the present disclosure will expand to fill a void in the body when implanted in vivo and exposed to a trigger and/or external stimulus.

Additionally, present methods and silk fibroin-based materials formed therefrom, in some embodiments, permit cellular infiltration and possess predictable degradation kinetics, which are properties that are clearly not present in prior shape memory polymers.

Silk Fibroin-Based Materials

In some embodiments, silk fibroin-based materials are or comprise silk fibroin and/or silk fibroin fragments.

Silks

In some embodiments, a polymer is silk. Silk is a natural protein fiber produced in a specialized gland of certain organisms. Silk production in organisms is especially common in the Hymenoptera (bees, wasps, and ants), and is sometimes used in nest construction. Other types of arthropod also produce silk, most notably various arachnids such as spiders (e.g., spider silk). Silk fibers generated by insects and spiders represent the strongest natural fibers known and rival even synthetic high performance fibers.

Silk has been a highly desired and widely used textile since its first appearance in ancient China (see Elisseeff, "The Silk Roads: Highways of Culture and Commerce," Berghahn Books/UNESCO, New York (2000); see also Vainker, "Chinese Silk: A Cultural History," Rutgers University Press, Piscataway, N.J. (2004)). Glossy and smooth, silk is favored by not only fashion designers but also tissue engineers because it is mechanically tough but degrades harmlessly inside the body, offering new opportunities as a highly robust and biocompatible material substrate (see Altman et al., Biomaterials, 24: 401 (2003); see also Sashina et al., Russ. J. Appl. Chem., 79: 869 (2006)).

Silk is naturally produced by various species, including, without limitation: *Antheraea mylitta*; *Antheraea pernyi*; *Antheraea yamamai*; *Galleria mellonella*; *Bombyx mori*; *Bombyx mandarina*; *Galleria mellonella*; *Nephila clavipes*; *Nephila senegalensis*; *Gasteracantha mammosa*; *Argiope aurantia*; *Araneus diadematus*; *Latrodectus geometricus*; *Araneus bicentenarius*; *Tetragnatha versicolor*; *Araneus ventricosus*; *Dolomedes tenebrosus*; *Euagrus chisoseus*; *Plectreurys tristis*; *Argiope trifasciata*; and *Nephila madagascariensis*.

In general, silk for use in accordance with the present disclosure may be produced by any such organism, from a recombinant source or may be prepared through an artificial process, for example, involving genetic engineering of cells or organisms to produce a silk protein and/or chemical synthesis. In some embodiments of the present disclosure, silk is produced by the silkworm, *Bombyx mori*.

As is known in the art, silks are modular in design, with large internal repeats flanked by shorter (~100 amino acid) terminal domains (N and C termini). Naturally-occurring silks have high molecular weight (200 to 350 kDa or higher) with transcripts of 10,000 base pairs and higher and >3000 amino acids (reviewed in Omenetto and Kaplan (2010) Science 329: 528-531). The larger modular domains are interrupted with relatively short spacers with hydrophobic charge groups in the case of silkworm silk. N- and C-termini are involved in the assembly and processing of silks, including pH control of assembly. The N- and C-termini are highly conserved, in spite of their relatively small size compared with the internal modules. Table 1, below, provides an exemplary list of silk-producing species and silk proteins:

TABLE 1

An exemplary list of silk-producing species and silk proteins (adopted from Bini et al. (2003), J. Mol. Biol. 335(1): 27-40).

| Accession | Species | Producing gland | Protein |
|---|---|---|---|
| A. Silkworms | | | |
| AAN28165 | *Antheraea mylitta* | Salivary | Fibroin |
| AAC32606 | *Antheraea pernyi* | Salivary | Fibroin |
| AAK83145 | *Antheraea yamamai* | Salivary | Fibroin |
| AAG10393 | *Galleria mellonella* | Salivary | Heavy-chain fibroin (N-terminal) |
| AAG10394 | *Galleria mellonella* | Salivary | Heavy-chain fibroin (C-terminal) |
| P05790 | *Bombyx mori* | Salivary | Fibroin heavy chain precursor, Fib-H, H-fibroin |
| CAA27612 | *Bombyx mandarina* | Salivary | Fibroin |
| Q26427 | *Galleria mellonella* | Salivary | Fibroin light chain precursor, Fib-L, L-fibroin, PG-1 |
| P21828 | *Bombyx mori* | Salivary | Fibroin light chain precursor, Fib-L, L-fibroin |

TABLE 1-continued

An exemplary list of silk-producing species and silk proteins (adopted from Bini et al. (2003), J. Mol. Biol. 335(1): 27-40).

| Accession | Species | Producing gland | Protein |
|---|---|---|---|
| B. Spiders | | | |
| P19837 | *Nephila clavipes* | Major ampullate | Spidroin 1, dragline silk fibroin 1 |
| P46804 | *Nephila clavipes* | Major ampullate | Spidroin 2, dragline silk fibroin 2 |
| AAK30609 | *Nephila senegalensis* | Major ampullate | Spidroin 2 |
| AAK30601 | *Gasteracantha mammosa* | Major ampullate | Spidroin 2 |
| AAK30592 | *Argiope aurantia* | Major ampullate | Spidroin 2 |
| AAC47011 | *Araneus diadematus* | Major ampullate | Fibroin-4, ADF-4 |
| AAK30604 | *Latrodectus geometricus* | Major ampullate | Spidroin 2 |
| AAC04503 | *Araneus bicentenarius* | Major ampullate | Spidroin 2 |
| AAK30615 | *Tetragnatha versicolor* | Major ampullate | Spidroin 1 |
| AAN85280 | *Araneus ventricosus* | Major ampullate | Dragline silk protein-1 |
| AAN85281 | *Araneus ventricosus* | Major ampullate | Dragline silk protein-2 |
| AAC14589 | *Nephila clavipes* | Minor ampullate | MiSp1 silk protein |
| AAK30598 | *Dolomedes tenebrosus* | Ampullate | Fibroin 1 |
| AAK30599 | *Dolomedes tenebrosus* | Ampullate | Fibroin 2 |
| AAK30600 | *Euagrus chisoseus* | Combined | Fibroin 1 |
| AAK30610 | *Plectreurys tristis* | Larger ampule-shaped | Fibroin 1 |
| AAK30611 | *Plectreurys tristis* | Larger ampule-shaped | Fibroin 2 |
| AAK30612 | *Plectreurys tristis* | Larger ampule-shaped | Fibroin 3 |
| AAK30613 | *Plectreurys tristis* | Larger ampule-shaped | Fibroin 4 |
| AAK30593 | *Argiope trifasciata* | Flagelliform | Silk protein |
| AAF36091 | *Nephila madagascariensis* | Flagelliform | Fibroin, silk protein (N-terminal) |
| AAF36092 | *Nephila madagascariensis* | Flagelliform | Silk protein (C-terminal) |
| AAC38846 | *Nephila clavipes* | Flagelliform | Fibroin, silk protein (N-terminal) |
| AAC38847 | *Nephila clavipes* | Flagelliform | Silk protein (C-terminal) |

Silk Fibroin

Fibroin is a type of structural protein produced by certain spider and insect species that produce silk. Cocoon silk produced by the silkworm, *Bombyx mori*, is of particular interest because it offers low-cost, bulk-scale production suitable for a number of commercial applications, such as textile.

Silkworm cocoon silk contains two structural proteins, the fibroin heavy chain (~350 kDa) and the fibroin light chain (~25 kDa), which are associated with a family of non-structural proteins termed sericin, which glue the fibroin brings together in forming the cocoon. The heavy and light chains of fibroin are linked by a disulfide bond at the C-terminus of the two subunits (see Takei, F., Kikuchi, Y., Kikuchi, A., Mizuno, S. and Shimura, K. (1987) 105 J. Cell Biol., 175-180; see also Tanaka, K., Mori, K. and Mizuno, S. 114 J. Biochem. (Tokyo), 1-4 (1993); Tanaka, K., Kajiyama, N., Ishikura, K., Waga, S., Kikuchi, A., Ohtomo, K., Takagi, T. and Mizuno, S., 1432 Biochim. Biophys. Acta., 92-103 (1999); Y Kikuchi, K Mori, S Suzuki, K Yamaguchi and S Mizuno, "Structure of the *Bombyx mori* fibroin light-chain-encoding gene: upstream sequence elements common to the light and heavy chain," 110 Gene, 151-158 (1992)). The sericins are a high molecular weight, soluble glycoprotein constituent of silk which gives the stickiness to the material. These glycoproteins are hydrophilic and can be easily removed from cocoons by boiling in water.

As used herein, the term "silk fibroin" refers to silk fibroin protein, whether produced by silkworm, spider, or other insect, or otherwise generated (Lucas et al., 13 Adv. Protein Chem., 107-242 (1958)). In some embodiments, silk fibroin is obtained from a solution containing a dissolved silkworm silk or spider silk. For example, in some embodiments, silkworm silk fibroins are obtained, from the cocoon of *Bombyx mori*. In some embodiments, spider silk fibroins are obtained, for example, from *Nephila clavipes*. In the alternative, in some embodiments, silk fibroins suitable for use in the invention are obtained from a solution containing a genetically engineered silk harvested from bacteria, yeast, mammalian cells, transgenic animals or transgenic plants. See, e.g., WO 97/08315 and U.S. Pat. No. 5,245,012, each of which is incorporated herein as reference in its entirety.

Thus, in some embodiments, a silk solution is used to fabricate compositions of the present disclosure contain fibroin proteins, essentially free of sericins. In some embodiments, silk solutions used to fabricate various compositions of the present disclosure contain the heavy chain of fibroin, but are essentially free of other proteins. In other embodiments, silk solutions used to fabricate various compositions of the present disclosure contain both the heavy and light chains of fibroin, but are essentially free of other proteins. In certain embodiments, silk solutions used to fabricate various compositions of the present disclosure comprise both a heavy and a light chain of silk fibroin; in some such embodiments, the heavy chain and the light chain of silk fibroin are linked via at least one disulfide bond. In some embodiments where the heavy and light chains of fibroin are present, they are linked via one, two, three or more disulfide bonds. Although different species of silk-producing organisms, and different types of silk, have different amino acid compositions, various fibroin proteins share certain structural features. A general trend in silk fibroin structure is a sequence of amino acids that is characterized by usually alternating glycine and alanine, or alanine alone. Such configuration allows fibroin molecules to self-assemble into a beta-sheet conformation. These "Alanine-rich" hydrophobic blocks are typically separated by segments of amino acids with bulky side-groups (e.g., hydrophilic spacers).

Silk materials explicitly exemplified herein were typically prepared from material spun by silkworm, *Bombyx mori*. Typically, cocoons are boiled in an aqueous solution of 0.02 M $Na_2CO_3$, then rinsed thoroughly with water to extract the glue-like sericin proteins. Extracted silk is then dissolved in a solvent, for example, LiBr (such as 9.3 M) solution at room temperature. A resulting silk fibroin solution can then be further processed for a variety of applications as described elsewhere herein.

In some embodiments, polymers refers to peptide chains or polypeptides having an amino acid sequence corresponding to fragments derived from silk fibroin protein or variants thereof. In the context of silk fibroin-based materials of the present disclosure, silk fibroin fragments generally refer to silk fibroin peptide chains or polypeptides that are smaller than naturally occurring full length silk fibroin counterpart, such that one or more of the silk fibroin fragments within a population or composition. In some embodiments, for example, silk fibroin-based materials comprise silk fibroin polypeptides having an average molecular weight of between about 3.5 kDa and about 400 kDa. In some embodiments, suitable ranges of silk fibroin fragments include, but are not limited to: silk fibroin polypeptides having an average molecular weight of between about 3.5 kDa and about 200 kDa; silk fibroin polypeptides having an average molecular weight of between about 3.5 kDa and about 150 kDa; silk fibroin polypeptides having an average molecular weight of between about 3.5 kDa and about 120 kDa. In some embodiments, silk fibroin polypeptides have an average molecular weight of: about 3.5 kDa, about 4 kDa, about 4.5 kDa, about 5 kDa, about 6 kDa, about 7 kDa, about 8 kDa, about 9 kDa, about 10 kDa, about 15 kDa, about 20 kDa, about 25 kDa, about 30 kDa, about 35 kDa, about 40 kDa, about 45 kDa, about 50 kDa, about 55 kDa, about 60 kDa, about 65 kDa, about 70 kDa, about 75 kDa, about 80 kDa, about 85 kDa, about 90 kDa, about 95 kDa, about 100 kDa, about 105 kDa, about 110 kDa, about 115 kDa, about 120 kDa, about 125 kDa, about 150 kDa, about 200 kDa, about 250 kDa, about 300 kDa, about 350 kDa, or about 400 kDa. In some preferred embodiments, silk fibroin polypeptides have an average molecular weight of about 100 kDa.

In some embodiments, silk fibroin-based materials are or comprise silk fibroin and/or silk fibroin fragments. In some embodiments, silk fibroin and/or silk fibroin fragments of various molecular weights may be used. In some embodiments, silk fibroin and/or silk fibroin fragments of various molecular weights are silk fibroin polypeptides. In some embodiments, silk fibroin polypeptides are "reduced" in size, for instance, smaller than the original or wild type counterpart, may be referred to as "low molecular weight silk fibroin." For more details related to low molecular weight silk fibroins, see: U.S. provisional application concurrently filed herewith, entitled "LOW MOLECULAR WEIGHT SILK FIBROIN AND USES THEREOF," the entire contents of which are incorporated herein by reference. In some embodiments, silk fibroin polypeptides have an average molecular weight of: less than 350 kDa, less than 300 kDa, less than 250 kDa, less than 200 kDa, less than 175 kDa, less than 150 kDa, less than 120 kDa, less than 100 kDa, less than 90 kDa, less than 80 kDa, less than 70 kDa, less than 60 kDa, less than 50 kDa, less than 40 kDa, less than 30 kDa, less than 25 kDa, less than 20 kDa, less than 15 kDa, less than 12 kDa, less than 10 kDa, less than 9 kDa, less than 8 kDa, less than 7 kDa, less than 6 kDa, less than 5 kDa, less than 4 kDa, less than 3.5 kDa, less than 3 kDa, less than 2.5 kDa, less than 2 kDa, less than 1.5 kDa, or less than about 1.0 kDa, etc.

In some embodiments, polymers of silk fibroin fragments can be derived by degumming silk cocoons at or close to (e.g., within 5% around) an atmospheric boiling temperature for at least about: 1 minute of boiling, 2 minutes of boiling, 3 minutes of boiling, 4 minutes of boiling, 5 minutes of boiling, 6 minutes of boiling, 7 minutes of boiling, 8 minutes of boiling, 9 minutes of boiling, 10 minutes of boiling, 11 minutes of boiling, 12 minutes of boiling, 13 minutes of boiling, 14 minutes of boiling, 15 minutes of boiling, 16 minutes of boiling, 17 minutes of boiling, 18 minutes of boiling, 19 minutes of boiling, 20 minutes of boiling, 25 minutes of boiling, 30 minutes of boiling, 35 minutes of boiling, 40 minutes of boiling, 45 minutes of boiling, 50 minutes of boiling, 55 minutes of boiling, 60 minutes or longer, including, e.g., at least 70 minutes, at least 80 minutes, at least 90 minutes, at least 100 minutes, at least 110 minutes, at least about 120 minutes or longer. As used herein, the term "atmospheric boiling temperature" refers to a temperature at which a liquid boils under atmospheric pressure.

In some embodiments, silk fibroin-based materials of the present disclosure produced from silk fibroin fragments can be formed by degumming silk cocoons in an aqueous solution at temperatures of: about 30° C., about 35° C., about 40° C., about 45° C., about 50° C., about 45° C., about 60° C., about 65° C., about 70° C., about 75° C., about 80° C., about 85° C., about 90° C., about 95° C., about 100° C., about 105° C., about 110° C., about 115° C., about at least 120° C.

In some embodiments, such elevated temperature can be achieved by carrying out at least portion of the heating process (e.g., boiling process) under pressure. For example, suitable pressure under which silk fibroin fragments described herein can be produced are typically between about 10-40 psi, e.g., about 11 psi, about 12 psi, about 13 psi, about 14 psi, about 15 psi, about 16 psi, about 17 psi, about 18 psi, about 19 psi, about 20 psi, about 21 psi, about 22 psi, about 23 psi, about 24 psi, about 25 psi, about 26 psi, about 27 psi, about 28 psi, about 29 psi, about 30 psi, about 31 psi, about 32 psi, about 33 psi, about 34 psi, about 35 psi, about 36 psi, about 37 psi, about 38 psi, about 39 psi, or about 40 psi.

In some embodiments, provided silk fibroin-based materials are modulated by controlling a silk concentration. In some embodiments, a weight percentage of silk fibroin can be present in the solution at any concentration suited to the need. In some embodiments, a silk fibroin solution can have silk fibroin at a concentration of about 0.1 mg/mL to about 50 mg/mL. In some embodiments, a silk fibroin solution can comprise silk fibroin at a concentration of about less than 1 mg/mL, about less than 1.5 mg/mL, about less than 2 mg/mL, about less than 2.5 mg/mL, about less than 3 mg/mL, about less than 3.5 mg/mL, about less than 4 mg/mL, about less than 4.5 mg/mL, about less than 5 mg/mL, about less than 5.5 mg/mL, about less than 6 mg/mL, about less than 6.5 mg/mL, about less than 7 mg/mL, about less than 7.5 mg/mL, about less than 8 mg/mL, about less than 8.5 mg/mL, about less than 9 mg/mL, about less than 9.5 mg/mL, about less than 10 mg/mL, about less than 11 mg/mL, about less than 12 mg/mL, about less than 13 mg/mL, about less than 14 mg/mL, about less than 15 mg/mL, about less than 16 mg/mL, about less than 17 mg/mL, about less than 18 mg/mL, about less than 19 mg/mL, about less than 20 mg/mL, about less than 25 mg/mL, about less than 30 mg/mL, about less than 35 mg/mL, about less than 40 mg/mL, about less than 45 mg/mL, or about less than 50 mg/mL.

Degradation Properties of Silk-Based Materials

Additionally, as will be appreciated by those of skill in the art, much work has established that researchers have the ability to control the degradation process of silk. According to the present disclosure, such control can be particularly valuable in the fabrication of electronic components, and particularly of electronic components that are themselves and/or are compatible with biomaterials. Degradability (e.g., bio-degradability) is often essential for biomaterials used in tissue engineering and implantation. The present disclosure encompasses the recognition that such degradability is also relevant to and useful in the fabrication of silk electronic components.

According to the present disclosure, one particularly desirable feature of silk-based materials is the fact that they can be programmably degradable. That is, as is known in the art, depending on how a particular silk-based material is prepared, it can be controlled to degrade at certain rates. Degradability and controlled release of a substance from silk-based materials have been published (see, for example, WO 2004/080346, WO 2005/012606, WO 2005/123114, WO 2007/016524, WO 2008/150861, WO 2008/118133, each of which is incorporated by reference herein).

Control of silk material production methods as well as various forms of silk-based materials can generate silk compositions with known degradation properties. For example, using various silk fibroin-based materials entrapped agents such as therapeutics can be loaded in active form, which is then released in a controlled fashion, e.g., over the course of minutes, hours, days, weeks to months. It has been shown that layered silk fibroin coatings can be used to coat substrates of any material, shape and size, which then can be used to entrap molecules for controlled release, e.g., 2-90 days.

Crystalline Silk Materials

As known in the art and as described herein, silk proteins can stack with one another in crystalline arrays. Various properties of such arrays are determined, for example, by the degree of beta-sheet structure in the material, the degree of cross-linking between such beta sheets, the presence (or absence) of certain dopants or other materials. In some embodiments, one or more of these features is intentionally controlled or engineered to achieve particular characteristics of a silk matrix. In some embodiments, silk fibroin-based materials are characterized by crystalline structure, for example, comprising beta sheet structure and/or hydrogen bonding. In some embodiments, provided silk fibroin-based materials are characterized by a percent beta sheet structure within the range of about 0% to about 45%. In some embodiments, silk fibroin-based materials are characterized by crystalline structure, for example, comprising beta sheet structure of about 1%, about 2%, about 3%, about 4%, about 5%, about 6%, about 7%, about 8%, about 9%, about 10%, about 11%, about 12%, about 13%, about 1%, about 1%, about 1%, about 1%, about 1%, about 1%, about 1%, about 1%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, or about 45%.

Silk Fibroin-Based Materials

In some embodiments, provided silk fibroin-based materials are susceptible to compression. In some embodiments, provided silk fibroin-based materials can be compressed relative to its pre-compression volume, up to: about 30% of original, about 40% of original, about 50% of original, about 60% of original, about 70% of original, about 80% of original, or about 90% of original.

In some embodiments, compression is meant to mimic the stress required to compress a foam during injection via needle. Compressive stress of about 80% is meant to mimic insertion into a needle for injection.

In some embodiments, provided silk fibroin-based materials are injectable. In some embodiments, a viscosity of an injectable composition is modified by using a pharmaceutically acceptable thickening agent. In some embodiments, a thickening agent, for example, is methylcellulose, xanthan gum, carboxymethyl cellulose, hydroxypropyl cellulose, carbomer, or combination thereof. A preferred concentration of the thickener depends upon a selected agent and viscosity for injection.

In some embodiments, when exposed to a trigger and/or external stimulus, provided silk fibroin-based materials are characterized by volumetric expansion.

In some embodiments, when exposed to a trigger and/or external stimulus, provided silk fibroin-based materials exhibit rapid re-swelling. In some embodiments, rapid re-swelling is on an order of seconds or tens of seconds. In some embodiments, rapid swelling is on an order of minutes, such as about 2, about 3, about 4, about 5, or about 10. In some embodiments, swelling may take longer.

In some embodiments, when exposed to a trigger and/or external stimulus, provided silk fibroin-based materials exhibit volumetric swelling. In some embodiments, such silk fibroin-based materials swell by volume relative to that of a compressed state by about two times ("2×"), about 3×, about 4×, about 5×, about 6×, about 7×, about 8×, about 9×, about 10×, about 15×, about 20×, about 25×, about 30×, about 35×, about 40×, about 45×, about 50×, about 55×, about 60×, about 65×, about 70×, about 75×, or more.

In some embodiments, when exposed to a trigger and/or external stimulus, for example, exposure to an aqueous medium, provided silk fibroin-based materials swell by mass relative to that of a compressed state of at least: about 400%, about 450%, about 500%, about 550%, about 600%, about 650%, about 700%, about 750%, about 800%, about 850%, about 900%, about 950%, or about 1000%, or more.

In some embodiments, when compressed silk fibroin-based materials may deform relative to its pre-compressed state shape. In some embodiments, provided silk fibroin-based materials substantially recover from deformation to their pre-compressed state shape when exposed to a trigger and/or external stimulus.

In some embodiments, silk fibroin-based materials comprise modified silk.

In some embodiments, modified silk differs from unmodified silk because an additive, agent, and/or functional moiety reacts with silk in a silk solution during manufacturing of silk fibroin-based materials. In some embodiments, modified silk differs from unmodified silk because an additive, agent, and/or functional moiety is mixed with a silk solution during manufacturing of silk fibroin-based materials. In some embodiments, modified silk differs from unmodified silk because an additive, agent, and/or functional moiety is mixed with, added to, applied to a silk fibroin-based material. In some embodiments, modified silk differs from unmodified silk because an additive, agent, and/or functional moiety reacts with silk in a silk fibroin-based material.

In some embodiments, modified silk differs from unmodified silk due addition of one or more pendant moieties (e.g., to an R group of an amino acid), inclusion of one or more non-natural amino acids, association with (e.g., covalent linkage to) one or more moieties such as a peptide, lipid, carbohydrate, nucleic acid, small molecule, metal, etc. In some embodiments, a modified silk fibroin-based comprises one or more modified amino acid residues. In some embodiments, a modified amino acid residue is a modified tyrosine residue. In some embodiments, a modified tyrosine residue is covalently modified (e.g., by addition of one or more pendant groups).

In some embodiments, silk fibroin-based materials comprised of such modified silk are characterized by certain silk fibroin-based materials' unique swelling properties, e.g., as described herein. In some embodiments, silk fibroin based materials comprising modified silk have increased hydrophilicity, so that modified silk fibroin-based materials have improved its hydrophilicity relative to unmodified silk materials. In some embodiments, silk fibroin based materials have increased water absorption capacity, so that modified silk fibroin-based materials have improved water absorption capacity relative to unmodified silk materials. In some embodiments, modified silk shows an improved hydrophobicity relative to unmodified silk. In some embodiments, modified silk shows may be able to increase absorption of non-polar fluids (e.g. oils or fats) in silk materials.

In some particular embodiments, for example, a modified silk differs from a natural silk due to modification 4-sulfanilic acid. In some particular embodiments, a modified silk is modified with poly-lysine (e.g., is a fusion peptide comprising a poly-lysine portion and a silk fibroin portion). In some particular embodiments, a modified silk is pegylated. In some particular embodiments, a modified silk is modified with 4-(heptyloxy)aniline. In some particular embodiments, a modified silk is modified with 4'-aminoacetophenone. Other exemplary plasticizers are described throughout the present application.

In some embodiments, silk fibroin-based materials comprising modified silk are characterized by between about 5% and about 75% modified silk concentration. In some embodiments, silk fibroin-based materials are characterized by: at least about 5% modification, at least about 10% modification, at least about 15% modification, at least about 20% modification, at least about 25% modification, at least about 30% modification, at least about 35% modification, at least about 40% modification, at least about 45% modification, at least about 50% modification, at least about 55% modification, at least about 60% modification, at least about 65% modification, at least about 70% modification, at least about 75% modification, or more.

In some embodiments, provided silk fibroin-based materials include a plasticizer. In some embodiments, such silk fibroin-based materials that include a plasticizer exhibit enhanced properties when compared with silk fibroin-based materials that do not include a plasticizer materials. In some embodiments, such silk fibroin-based materials comprising plasticizers exhibit increased crystallinity relative to silk fibroin-based materials without a plasticizer. In some embodiments, provided silk fibroin-based materials comprising plasticizers exhibit improved recovery properties with increasing plasticizer concentration.

In some embodiments, silk fibroin-based materials include: at least 1% plasticizer, at least 2% plasticizer, at least 3% plasticizer, at least 4% plasticizer, at least 5% plasticizer, at least 6% plasticizer, at least 7% plasticizer, at least 8% plasticizer, at least 9% plasticizer, at least 10% plasticizer, at least 15% plasticizer, at least 20% plasticizer, at least 25% plasticizer, at least 30% plasticizer, at least 35% plasticizer, at least 40% plasticizer, at least 45% plasticizer, at least 50% plasticizer, at least 55% plasticizer, at least 60% plasticizer, at least 65% plasticizer, at least 70% plasticizer, or more.

In some embodiments, silk fibroin-based materials without plasticizer recover from compression as described herein. In some embodiments, silk fibroin-based materials without plasticizer recover to: at least about 25% of their original volume after compression, at least about 30% of their original volume after compression, at least about 35% of their original volume after compression, at least about 40% of their original volume after compression, at least about 45% of their original volume after compression, at least about 50% of their original volume after compression, at least about 55% of their original volume after compression, at least about 60% of their original volume after compression, at least about 65% of their original volume after compression, at least about 70% of their original volume after compression, or at least about 75% of their original volume after compression.

In some embodiments, silk fibroin-based materials comprising a plasticizer recover from compression as described herein. In some embodiments, silk fibroin-based materials with plasticizer recover to: at least about 25% of their original volume after compression, at least about 30% of their original volume after compression, at least about 35% of their original volume after compression, at least about 40% of their original volume after compression, at least about 45% of their original volume after compression, at least about 50% of their original volume after compression, at least about 55% of their original volume after compression, at least about 60% of their original volume after compression, at least about 65% of their original volume after compression, at least about 70% of their original volume after compression, at least about 75% of their original volume after compression, at least about 80% of their original volume after compression, at least about 85% of their original volume after compression, at least about 90% of their original volume after compression, at least about 95% of their original volume after compression, or about 100% of their original volume after compression.

In some embodiments, provided silk fibroin-based materials comprising at least 20% w/w glycerol recover to 90-95% of their original volume after compression. Without methanol treatment, glycerol containing silk fibroin materials as provided herein can recover almost 100% of their original volume after severe compression (about 80%).

In some embodiments, silk fibroin-based materials without plasticizer swelled approximately 400% of their starting mass. In some embodiments, silk fibroin-based materials without plasticizer exhibited incomplete recovery with respect to their original volume. In some embodiments, silk fibroin-based materials without plasticizer exhibited plastic deformation following recovery. In some embodiments, silk fibroin-based materials without plasticizer exhibited volume expansion from a compressed state to about 2 times the original volume.

In some embodiments, provided silk fibroin-based materials comprising a plasticizer swelled up to about 900% of their starting mass. In some embodiments, such silk fibroin-based materials with plasticizer exhibited complete recovery with respect to their original volume. In some embodiments, such silk fibroin-based materials with plasticizer did not show evidence of plastic deformation following recovery. In some embodiments, such silk fibroin-based materials with plasticizer exhibited volume expansion from a compressed state up to about 60 times the original volume.

In some embodiments, provided silk fibroin-based materials are characterized as insoluble in water when such materials comprise: at least about 20% plasticizer, at least about 25% plasticizer, at least about 30% plasticizer, at least about 35% plasticizer, at least about 40% plasticizer, at least about 45% plasticizer, at least about 50% plasticizer, at least about 55% plasticizer, at least about 60% plasticizer, at least about 65% plasticizer, or at least about 70% plasticizer.

In some embodiments, provided silk fibroin-based materials are characterized by a structure that includes open cells; pores. In some embodiments, provided silk fibroin-based materials comprise pores that are characterized in that they are substantially rounded. In some embodiments, provided silk fibroin-based materials comprise pores and such materials are characterized in that such pores evenly distributed through its bulk. In some embodiments, provided silk fibroin-based materials comprise pores and such materials are characterized in that such pores are interconnected throughout its bulk.

In some embodiments, pores formed by provided methods have an average pore diameter, including about 5 µm, about 10 µm, about 15 µm, about 20 µm, about 25 µm, about 30 µm, about 35 µm, about 40 µm, about 45 µm, about 50 µm, about 55 µm, about 60 µm, about 65 µm, about 70 µm, about 75 µm, about 80 µm, about 85 µm, about 90 µm, about 95 µm, about 100 µm, about 125 µm, about 150 µm, about 175 µm, about 200 µm, about 225 µm, about 250 µm, about 275 µm, about 300 µm, about 325 µm, about 350 µm, about 375 µm, about 400 µm, about 450 µm, about 475 µm, or about 500 µm, or more.

In some embodiments, an average pore size in provided silk fibroin-based materials is not compromised by compression or expansion, that is, average pore size in a pre-compressed state is substantially identical relative to its average pore size following recovery. In some embodiments, pore morphology in provided silk fibroin-based materials is not compromised by compression or expansion, in that one or more features that characterize the materials' pore morphology are substantially identical after recovery from compression and/or expansion relative to its pre-compressed state.

In some embodiments, provided silk fibroin-based materials are characterized by an elastic modulus value in a range between about 1 kPa and about 2500 kPa. In some embodiments, silk fibroin-based materials are characterized by an elastic modulus of: less than about 1 kPa, less than about 2 kPa, less than about 3 kPa, less than about 4 kPa, less than about 5 kPa, less than about 6 kPa, less than about 7 kPa, less than about 8 kPa, less than about 9 kPa, less than about 10 kPa, less than about 15 kPa, less than about 20 kPa, less than about 25 kPa, less than about 30 kPa, less than about 35 kPa, less than about 40 kPa, less than about 45 kPa, less than about 50 kPa, less than about 55 kPa, less than about 60 kPa, less than about 65 kPa, less than about 70 kPa, less than about 75 kPa, less than about 80 kPa, less than about 85 kPa, less than about 90 kPa, less than about 95 kPa, less than about 100 kPa, less than about 125 kPa, less than about 150 kPa, less than about 175 kPa, less than about 200 kPa, less than about 225 kPa, less than about 250 kPa, less than about 275 kPa, less than about 300 kPa, less than about 325 kPa, less than about 350 kPa, less than about 375 kPa, less than about 400 kPa, less than about 425 kPa, less than about 450 kPa, less than about 475 kPa, less than about 500 kPa, less than about 600 kPa, less than about 700 kPa, less than about 800 kPa, less than about 900 kPa, less than about 1000 kPa, less than about 1100 kPa, less than about 1200 kPa, less than about 1300 kPa, less than about 1400 kPa, less than about 1500 kPa, less than about 1600 kPa, less than about 1700 kPa, less than about 1800 kPa, less than about 1900 kPa, less than about 2000 kPa, less than about 2100 kPa, less than about 2200 kPa, less than about 2300 kPa, less than about 2400 kPa, or less than about 2500 kPa.

In some embodiments, provided silk fibroin-based materials are characterized by a compressive modulus value in a range between about 500 Pa and about 3000 kPa. In some embodiments, silk fibroin-based materials are characterized by a compressive modulus of: less than about 500 Pa, less than about 600 Pa, less than about 700 Pa, less than about 800 Pa, less than about 900 Pa, less than about 1 kPa, less than about 2 kPa, less than about 3 kPa, less than about 4 kPa, less than about 5 kPa, less than about 6 kPa, less than about 7 kPa, less than about 8 kPa, less than about 9 kPa, less than about 10 kPa, less than about 15 kPa, less than about 20 kPa, less than about 25 kPa, less than about 30 kPa, less than about 35 kPa, less than about 40 kPa, less than about 45 kPa, less than about 50 kPa, less than about 55 kPa, less than about 60 kPa, less than about 65 kPa, less than about 70 kPa, less than about 75 kPa, less than about 80 kPa, less than about 85 kPa, less than about 90 kPa, less than about 95 kPa, less than about 100 kPa, less than about 125 kPa, less than about 150 kPa, less than about 175 kPa, less than about 200 kPa, less than about 225 kPa, less than about 250 kPa, less than about 275 kPa, less than about 300 kPa, less than about 325 kPa, less than about 350 kPa, less than about 375 kPa, less than about 400 kPa, less than about 425 kPa, less than about 450 kPa, less than about 475 kPa, less than about 500 kPa, less than about 600 kPa, less than about 700 kPa, less than about 800 kPa, less than about 900 kPa, less than about 1000 kPa, less than about 1100 kPa, less than about 1200 kPa, less than about 1300 kPa, less than about 1400 kPa, less than about 1500 kPa, less than about 1600 kPa, less than about 1700 kPa, less than about 1800 kPa, less than about 1900 kPa, less than about 2000 kPa, less than about 2100 kPa, less than about 2200 kPa, less than about 2300 kPa, less than about 2400 kPa, less than about 2500 kPa, less than about 2600 kPa, less than about 2700 kPa, less than about 2800 kPa, less than about 2900 kPa, or less than about 3000 kPa.

In some embodiments, provided silk fibroin-based materials are characterized by a storage modulus value in a range between about 1 kPa and about 3000 kPa. In some embodiments, silk fibroin-based materials are characterized by a compressive modulus of: less than about 1 kPa, less than about 2 kPa, less than about 3 kPa, less than about 4 kPa, less than about 5 kPa, less than about 6 kPa, less than about 7 kPa, less than about 8 kPa, less than about 9 kPa, less than about 10 kPa, less than about 15 kPa, less than about 20 kPa, less than about 25 kPa, less than about 30 kPa, less than about 35 kPa, less than about 40 kPa, less than about 45 kPa, less than about 50 kPa, less than about 55 kPa, less than about 60 kPa, less than about 65 kPa, less than about 70 kPa, less than about 75 kPa, less than about 80 kPa, less than about 85 kPa, less than about 90 kPa, less than about 95 kPa, less than about 100 kPa, less than about 125 kPa, less than about 150 kPa, less than about 175 kPa, less than about 200 kPa, less than about 225 kPa, less than about 250 kPa, less than about 275 kPa, less than about 300 kPa, less than about 325 kPa, less than about 350 kPa, less than about 375 kPa, less than about 400 kPa, less than about 425 kPa, less than about 450 kPa, less than about 475 kPa, less than about 500 kPa, less than about 600 kPa, less than about 700 kPa, less than about 800 kPa, less than about 900 kPa, less than about 1000 kPa, less than about 1100 kPa, less than about 1200 kPa, less than about 1300 kPa, less than about 1400 kPa, less than about 1500 kPa, less than about 1600 kPa, less than about 1700 kPa, less than about 1800 kPa, less than about 1900 kPa, less than about 2000 kPa, less than about 2100 kPa, less than about 2200 kPa, less than about 2300 kPa, less than about 2400 kPa, less than about 2500 kPa, less than about 2600 kPa, less than about 2700 kPa, less than about 2800 kPa, less than about 2900 kPa, or less than about 3000 kPa.

In some embodiments, provided silk fibroin-based materials are biocompatible. In some embodiments, silk fibroin-based materials include additives, agents, and/or functional moieties.

In some embodiments, provided silk fibroin-based materials are pre-loaded with additives, agents, and/or functional moieties during material fabrication. In some embodiments, provided silk fibroin-based materials uptake additives, agents, and/or functional moieties when in an expanded state.

In some embodiments, provided silk fibroin-based materials are biodegradable.

In some embodiments, provided silk fibroin-based materials are characterized in that such materials decompose, degrade, delaminate, or dissolve. In some embodiments, provided silk fibroin-based materials are characterized in that such materials decompose, degrade, delaminate, or dissolve to release an additive, agent, and/or functional moiety.

In some embodiments, provided silk fibroin-based materials are introduced in vivo. In some embodiments, such silk fibroin-based materials decompose, degrade, delaminate, or dissolve when present in vivo. In some embodiments, such silk fibroin-based materials decompose, degrade, delaminate, or dissolve without significant immunological response when present in vivo. In some embodiments, such silk fibroin-based materials exhibit predictable degradation kinetics. In some embodiments, such silk fibroin-based materials are resorbed in vivo and replaced with natural tissues.

Additives, Agents, and/or Functional Moieties

In any of the embodiments embraced by the present invention, silk fibroin-based materials may further include one or more additives, agents, and/or functional moieties and other active or inactive agents, depending on particular use.

In some embodiments, provided silk fibroin-based materials can comprise one or more (e.g., one, two, three, four, five or more) additives, agents, and/or functional moieties. Without wishing to be bound by a theory, additives, agents, and/or functional moieties can provide or enhance one or more desirable properties, e.g., strength, flexibility, ease of processing and handling, biocompatibility, bioresorbability, surface morphology, release rates and/or kinetics of one or more active agents present in the composition, and the like. In some embodiments, one or more such additives, agents, and/or functional moieties can be covalently or non-covalently linked with the silk fibroin-based material (e.g., with a polymer such as silk fibroin that makes up the material) and can be integrated homogenously or heterogeneously within the silk composition.

In some embodiments, additives, agents, and/or functional moieties are or comprises a moiety covalently associated (e.g., via chemical modification or genetic engineering) with a polymer. In some embodiments, an additive is non-covalently associated with a silk fibroin-based material or silk fibroin-based material component.

In some embodiments, provided silk fibroin-based materials comprise additives, agents, and/or functional moieties at a total amount from about 0.01 wt % to about 99 wt %, from about 0.01 wt % to about 70 wt %, from about 5 wt % to about 60 wt %, from about 10 wt % to about 50 wt %, from about 15 wt % to about 45 wt %, or from about 20 wt % to about 40 wt %, of the total silk composition. In some embodiments, ratio of silk fibroin to additive in the composition can range from about 1000:1 (w/w) to about 1:1000 (w/w), from about 500:1 (w/w) to about 1:500 (w/w), from about 250:1 (w/w) to about 1:250 (w/w), from about 200:1 (w/w) to about 1:200 (w/w), from about 25:1 (w/w) to about 1:25 (w/w), from about 20:1 (w/w) to about 1:20 (w/w), from about 10:1 (w/w) to about 1:10 (w/w), or from about 5:1 (w/w) to about 1:5 (w/w).

In some embodiments, provided silk fibroin-based materials include one or more additives, agents, and/or functional moieties at a molar ratio relative to polymer (i.e., a silk: additive ratio) of, e.g., at least 1000:1, at least 900:1, at least 800:1, at least 700:1, at least 600:1, at least 500:1, at least 400:1, at least 300:1, at least 200:1, at least 100:1, at least 90:1, at least 80:1, at least 70:1, at least 60:1, at least 50:1, at least 40:1, at least 30:1, at least 20:1, at least 10:1, at least 7:1, at least 5:1, at least 3:1, at least 1:1, at least 1:3, at least 1:5, at least 1:7, at least 1:10, at least 1:20, at least 1:30, at least 1:40, at least 1:50, at least 1:60, at least 1:70, at least 1:80, at least 1:90, at least 1:100, at least 1:200, at least 1:300, at least 1:400, at least 1:500, at least 600, at least 1:700, at least 1:800, at least 1:900, or at least 1:100.

In some embodiments, moiety silk:additive ratio is, e.g., at most 1000:1, at most 900:1, at most 800:1, at most 700:1, at most 600:1, at most 500:1, at most 400:1, at most 300:1, at most 200:1, 100:1, at most 90:1, at most 80:1, at most 70:1, at most 60:1, at most 50:1, at most 40:1, at most 30:1, at most 20:1, at most 10:1, at most 7:1, at most 5:1, at most 3:1, at most 1:1, at most 1:3, at most 1:5, at most 1:7, at most 1:10, at most 1:20, at most 1:30, at most 1:40, at most 1:50, at most 1:60, at most 1:70, at most 1:80, at most 1:90, at most 1:100, at most 1:200, at most 1:300, at most 1:400, at most 1:500, at most 1:600, at most 1:700, at most 1:800, at most 1:900, or at most 1:1000.

In some embodiments, moiety silk:additive ratio is, e.g., from about 1000:1 to about 1:1000, from about 900:1 to about 1:900, from about 800:1 to about 1:800, from about 700:1 to about 1:700, from about 600:1 to about 1:600, from about 500:1 to about 1:500, from about 400:1 to about 1:400, from about 300:1 to about 1:300, from about 200:1 to about 1:200, from about 100:1 to about 1:100, from about 90:1 to about 1:90, from about 80:1 to about 1:80, from about 70:1 to about 1:70, from about 60:1 to about 1:60, from about 50:1 to about 1:50, from about 40:1 to about 1:40, from about 30:1 to about 1:30, from about 20:1 to about 1:20, from about 10:1 to about 1:10, from about 7:1 to about 1:7, from about 5:1 to about 1:5, from about 3:1 to about 1:3, or about 1:1.

In some embodiments, provided silk fibroin-based materials comprise additives, agents, and/or functional moieties, for example, therapeutic, preventative, and/or diagnostic agents.

In some embodiments, an additives, agents, and/or functional moieties is or comprises one or more therapeutic agents. In general, a therapeutic agent is or comprises a small molecule and/or organic compound with pharmaceutical activity (e.g., activity that has been demonstrated with statistical significance in one or more relevant pre-clinical models or clinical settings). In some embodiments, a therapeutic agent is a clinically-used drug. In some embodiments, a therapeutic agent is or comprises an cells, proteins, peptides, nucleic acid analogues, nucleotides, oligonucleotides, nucleic acids (DNA, RNA, siRNA), peptide nucleic acids, aptamers, antibodies or fragments or portions thereof, anesthetic, anticoagulant, anti-cancer agent, inhibitor of an enzyme, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, anti-glaucoma agent, neuroprotectant, angiogenesis inhibitor, hormones, hormone antagonists, growth factors or recombinant growth factors and fragments and variants thereof, cytokines, enzymes, antibiotics or antimicrobial compounds, antifungals, antivirals, toxins, prodrugs, chemotherapeutic agents, small molecules, drugs (e.g., drugs, dyes, amino acids, vitamins, antioxidants), pharmacologic agents, and combinations thereof.

In some embodiments, provided silk fibroin-based materials comprise additives, agents, and/or functional moieties, for example, cells. Cells suitable for use herein include, but are not limited to, progenitor cells or stem cells, smooth muscle cells, skeletal muscle cells, cardiac muscle cells, epithelial cells, endothelial cells, urothelial cells, fibroblasts, myoblasts, chondrocytes, chondroblasts, osteoblasts, osteoclasts, keratinocytes, hepatocytes, bile duct cells, pancreatic islet cells, thyroid, parathyroid, adrenal, hypothalamic, pituitary, ovarian, testicular, salivary gland cells, adipocytes, and precursor cells.

In some embodiments, provided silk fibroin-based materials comprise additives, agents, and/or functional moieties, for example, organisms, such as, a bacterium, fungus, plant or animal, or a virus. In some embodiments, an active agent may include or be selected from neurotransmitters, hormones, intracellular signal transduction agents, pharmaceutically active agents, toxic agents, agricultural chemicals, chemical toxins, biological toxins, microbes, and animal cells such as neurons, liver cells, and immune system cells. The active agents may also include therapeutic compounds, such as pharmacological materials, vitamins, sedatives, hypnotics, prostaglandins and radiopharmaceuticals.

In some embodiments, provided silk fibroin-based materials comprise additives, agents, and/or functional moieties, for example, antibiotics. Antibiotics suitable for incorporation in silk fibroin-based materials include, but are not limited to, aminoglycosides (e.g., neomycin), ansamycins, carbacephem, carbapenems, cephalosporins (e.g., cefazolin, cefaclor, cefditoren, cefditoren, ceftobiprole), glycopeptides (e.g., vancomycin), macrolides (e.g., erythromycin, azithromycin), monobactams, penicillins (e.g., amoxicillin, ampicillin, cloxacillin, dicloxacillin, flucloxacillin), polypeptides (e.g., bacitracin, polymyxin B), quinolones (e.g., ciprofloxacin, enoxacin, gatifloxacin, ofloxacin, etc.), sulfonamides (e.g., sulfasalazine, trimethoprim, trimethoprim-sulfamethoxazole (co-trimoxazole)), tetracyclines (e.g., doxycyline, minocycline, tetracycline, etc.), chloramphenicol, lincomycin, clindamycin, ethambutol, mupirocin, metronidazole, pyrazinamide, thiamphenicol, rifampicin, thiamphenicl, dapsone, clofazimine, quinupristin, metronidazole, linezolid, isoniazid, fosfomycin, fusidic acid, β-lactam antibiotics, rifamycins, novobiocin, fusidate sodium, capreomycin, colistimethate, gramicidin, doxycycline, erythromycin, nalidixic acid, and vancomycin. For example, β-lactam antibiotics can be aziocillin, aztreonam, carbenicillin, cefoperazone, ceftriaxone, cephaloridine, cephalothin, moxalactam, piperacillin, ticarcillin and combination thereof.

In some embodiments, provided silk fibroin-based materials comprise additives, agents, and/or functional moieties, for example, anti-inflammatories. Anti-inflammatory agents may include corticosteroids (e.g., glucocorticoids), cycloplegics, non-steroidal anti-inflammatory drugs (NSAIDs), immune selective anti-inflammatory derivatives (ImSAIDs), and any combination thereof. Exemplary NSAIDs include, but not limited to, celecoxib (Celebrex®); rofecoxib (Vioxx®), etoricoxib (Arcoxia®), meloxicam (Mobic®), valdecoxib, diclofenac (Voltaren®, Cataflam®), etodolac (Lodine®), sulindac (Clinori®), aspirin, alclofenac, fenclofenac, diflunisal (Dolobid®), benorylate, fosfosal, salicylic acid including acetylsalicylic acid, sodium acetylsalicylic acid, calcium acetylsalicylic acid, and sodium salicylate; ibuprofen (Motrin), ketoprofen, carprofen, fenbufen, flurbiprofen, oxaprozin, suprofen, triaprofenic acid, fenoprofen, indoprofen, piroprofen, flufenamic, mefenamic, meclofenamic, niflumic, salsalate, rolmerin, fentiazac, tilomisole, oxyphenbutazone, phenylbutazone, apazone, feprazone, sudoxicam, isoxicam, tenoxicam, piroxicam (Feldene®), indomethacin (Indocin®), nabumetone (Relafen®), naproxen (Naprosyn®), tolmetin, lumiracoxib, parecoxib, licofelone (ML3000), including pharmaceutically acceptable salts, isomers, enantiomers, derivatives, prodrugs, crystal polymorphs, amorphous modifications, co-crystals and combinations thereof.

In some embodiments, provided silk fibroin-based materials comprise additives, agents, and/or functional moieties, for example, antibodies. Suitable antibodies for incorporation in silk fibroin-based materials include, but are not limited to, abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, ofatumumab omalizumab, palivizumab, panitumumab, ranibizumab, rituximab, tositumomab, trastuzumab, altumomab pentetate, arcitumomab, atlizumab, bectumomab, belimumab, besilesomab, biciromab, canakinumab, capromab pendetide, catumaxomab, denosumab, edrecolomab, efungumab, ertumaxomab, etaracizumab, fanolesomab, fontolizumab, gemtuzumab ozogamicin, golimumab, igovomab, imciromab, labetuzumab, mepolizumab, motavizumab, nimotuzumab, nofetumomab merpentan, oregovomab, pemtumomab, pertuzumab, rovelizumab, ruplizumab, sulesomab, tacatuzumab tetraxetan, tefibazumab, tocilizumab, ustekinumab, visilizumab, votumumab, zalutumumab, and zanolimumab.

In some embodiments, provided silk fibroin-based materials comprise additives, agents, and/or functional moieties, for example, polypeptides (e.g., proteins), including but are not limited to: one or more antigens, cytokines, hormones, chemokines, enzymes, and any combination thereof as an agent and/or functional group. Exemplary enzymes suitable for use herein include, but are not limited to, peroxidase, lipase, amylose, organophosphate dehydrogenase, ligases, restriction endonucleases, ribonucleases, DNA polymerases, glucose oxidase, laccase, and the like.

In some embodiments, provided silk fibroin-based materials comprise additives, agents, and/or functional moieties, for example, particularly useful for wound healing. In some embodiments, agents useful for wound healing include stimulators, enhancers or positive mediators of the wound healing cascade which 1) promote or accelerate the natural wound healing process or 2) reduce effects associated with improper or delayed wound healing, which effects include, for example, adverse inflammation, epithelialization, angiogenesis and matrix deposition, and scarring and fibrosis.

In some embodiments, provided silk fibroin-based materials comprise additives, agents, and/or functional moieties, for example, an optically or electrically active agent, including but not limited to, chromophores; light emitting organic compounds such as luciferin, carotenes; light emitting inorganic compounds, such as chemical dyes; light harvesting compounds such as chlorophyll, bacteriorhodopsin, protorhodopsin, and porphyrins; light capturing complexes such as phycobiliproteins; and related electronically active compounds; and combinations thereof.

In some embodiments, provided silk fibroin-based materials comprise additives, agents, and/or functional moieties, for example, particularly useful for chemical modification of silk fibroin-based material. In some embodiments, provided silk fibroin-based materials comprise additives, agents, and/or functional moieties, for example, particularly to improve hydrophilicity, absorbency of water, shape retention, or hydrophobicity, including but not limited to: 4-sulfanilic acid, poly-lysine, 4-(heptyloxy)aniline, 4'-aminoacetophenone, superabsorbent polymers; examples include but are not limited to sodium polyacrylate, crosslinked polyvinyl alcohol (PVA), polyethylene oxide (PEO), polyacrylic acid, hygroscopic materials, cellulose and starch (e.g. modified or unmodified), nylon, polycarbonate, polyethylene glycol, or combinations thereof.

Plasticizers

In some embodiments, while not required, examples of suitable additives may include, without limitation, one or more plasticizers. As used in the context of the present disclosure, the terms "plasticizer" and "plasticizing agent" interchangeably are used.

In some embodiments, provided silk fibroin-based materials comprising plasticizers exhibit improved recovery properties with increasing plasticizer concentration. In some embodiments, silk fibroin-based material preparation includes a plasticizer to promote plasticity and flexibility and to reduce brittleness. In some embodiments, such silk fibroin-based materials comprising plasticizers exhibit increased crystallinity relative to silk fibroin-based materials without a plasticizer. In some embodiments, provided silk fibroin-based materials comprising plasticizers exhibit improved recovery properties with increasing plasticizer concentration. Typically, in some embodiments, a plasticizer is a hygroscopic substance that forms hydrogen or electrostatic bonds with the biopolymer and that increases the amount of free and freezing bond water retained in the biopolymer materials.

In some embodiments, plasticizers are or comprise, but are not limited to: glycerol, 1,2 Propanediol, 1,3 Propanediol, 1,4 Butanediol, 1,2,4 Butanetriol, Threitol, Erythritol, 1,2 Pentanediol, 1,5 Pentanediol, Adonitol, 1,2,6 Hexanetriol, Glycerin; Glyceryl oleate; Oleyl alcohol; PEG-4 PEG-6; PEG-8; PEG-12; PEG-16; PEG-20 PEG-32; PEG-75 (Ref. Handbook of Green Chemistry, Part IV Functional/Application, pp. 2759), stearic acid, oleic acid, sodium lactate, Emerest® 2618; Emerest® 2619; Hydrobrite® 200PO; Hydrobrite® 380PO; Hydrobrite® 550PO PEG-20 stearate; Propylene glycol laurate; Semtol® 40; Semtol® 70; Semtol® 85 Semtol® 100; Semtol® 350 (Ref. Handbook of Green Chemistry, Part IV Functional/Application, pp. 2755), sodium polyacrylate, crosslinked polyvinyl alcohol (PVA), polyethylene oxide (PEO), polyacrylic acid, hygroscopic materials, cellulose and starch (e.g. modified or unmodified), nylon, polycarbonate, polyethylene glycol, methanol, ethanol, propanol isomers: 1-propanol, isopropyl alcohol, butanol isomers: n-butanol; sec-butanol; isobutanol; tert-butanol, pentanol isomers (amyl alcohol): n-pentanol; isobutyl carbinol; active amyl alcohol; tertiary butyl carbinol; 3-pentanol; methyl (n) propyl carbinol; methyl isopropyl carbinol; dimethyl ethyl carbinol, hexanol: n-hexanol and related isomers, heptanol and related isomers, octanol and related isomers, nonanol and related isomers, decanol and related isomers, diols, vicinal diols (hydroxyl groups attached to adjacent atoms); examples include but are not limited to: propane-1,2-diol, ethylene glycol, propylene glycol, 1,3 diols; examples include but are not limited to: propane-1,3-diol, 2,2-dimethyl-1,3-propanediol, 1,3 butanediol, 1,4 diols; examples include but are not limited to: 1,4-butanediol, 1,4-pentanediol, 1,5 diols and longer; triols; examples include but are not limited to: Glycerol, Benzenetriol, Pyrogallol, 1,2,6 Hexanetriol, 1,3,5-pentanetriol, Phenols; examples include but are not limited to: Hydroquinone, Resorcinol, Meta-cresol, Eugenol, Thymol, Pyrogallol, Sugar Alcohols or polyhydric alcohols, Arabitol, Erythritol, Fucitol, Galactitol, Glycerol, Iditol, Inositol, Isomalt, Lactitol, Maltitol, Maltotetraitol, Maltotriitol, Mannitol, Ribitol (adonitol), Sorbitol, Threitol, Volemitol, Xylitol, Ethylene glycol, diethylene glycol, Hydrogenated starch hydrolysates; polyglycitol (mixtures of sugar alcohols used in food industries), propylene glycol (E1520), hexylene glycol, and butylene glycol; glyceryl triacetate (E1518); vinyl alcohol; neoagarobiose; Sugar alcohols/sugar polyols: glycerol/glycerin, sorbitol (E420), xylitol, maltitol (E965); polymeric polyols (e.g., polydextrose (E1200)); quillaia (E999); urea; aloe vera gel; MP Diol; alpha hydroxy acids (e.g., lactic acid); honey, sugars and simple sugars (e.g. monosaccharides, disaccharides, oligosaccharides, polysaccharides); examples include but are not limited to: sucrose, glucose, fructose, ribose, galactose, maltose, lactose, triose, tetrose, pentose, hexose, trehalose, or combinations thereof.

Nucleic Acids

In some embodiments, provided silk fibroin-based materials comprise additives, agents, and/or functional moieties, for example, nucleic acid agents. In some embodiments, a silk fibroin-based materials may release nucleic acid agents. In some embodiments, a nucleic acid agent is or comprises a therapeutic agent. In some embodiments, a nucleic acid agent is or comprises a diagnostic agent. In some embodiments, a nucleic acid agent is or comprises a prophylactic agent.

It would be appreciated by those of ordinary skill in the art that a nucleic acid agent can have a length within a broad range. In some embodiments, a nucleic acid agent has a nucleotide sequence of at least about 40, for example at least about 60, at least about 80, at least about 100, at least about 200, at least about 500, at least about 1000, or at least about 3000 nucleotides in length. In some embodiments, a nucleic acid agent has a length from about 6 to about 40 nucleotides. For example, a nucleic acid agent may be from about 12 to about 35 nucleotides in length, from about 12 to about 20 nucleotides in length or from about 18 to about 32 nucleotides in length.

In some embodiments, nucleic acid agents may be or comprise deoxyribonucleic acids (DNA), ribonucleic acids (RNA), peptide nucleic acids (PNA), morpholino nucleic acids, locked nucleic acids (LNA), glycol nucleic acids (GNA), threose nucleic acids (TNA), and/or combinations thereof.

In some embodiments, a nucleic acid has a nucleotide sequence that is or comprises at least one protein-coding element. In some embodiments, a nucleic acid has a nucleotide sequence that is or comprises at least one element that is a complement to a protein-coding sequence. In some embodiments, a nucleic acid has a nucleotide sequence that includes one or more gene expression regulatory elements (e.g., promoter elements, enhancer elements, splice donor sites, splice acceptor sites, transcription termination sequences, translation initiation sequences, translation termination sequences, etc.). In some embodiments, a nucleic acid has a nucleotide sequence that includes an origin of replication. In some embodiments, a nucleic acid has a nucleotide sequence that includes one or more integration sequences. In some embodiments, a nucleic acid has a nucleotide sequence that includes one or more elements that participate in intra- or inter-molecular recombination (e.g., homologous recombination). In some embodiments, a nucleic acid has enzymatic activity. In some embodiments, a nucleic acid hybridizes with a target in a cell, tissue, or organism. In some embodiments, a nucleic acid acts on (e.g., binds with, cleaves, etc.) a target inside a cell. In some embodiments, a nucleic acid is expressed in a cell after release from a provided composition. In some embodiments, a nucleic acid integrates into a genome in a cell after release from a provided composition.

In some embodiments, nucleic acid agents have single-stranded nucleotide sequences. In some embodiments, nucleic acid agents have nucleotide sequences that fold into higher order structures (e.g., double and/or triple-stranded structures). In some embodiments, a nucleic acid agent is or comprises an oligonucleotide. In some embodiments, a nucleic acid agent is or comprises an antisense oligonucleotide. Nucleic acid agents may include a chemical modification at the individual nucleotide level or at the oligonucleotide backbone level, or it may have no modifications.

In some embodiments of the present disclosure, a nucleic acid agent is an siRNA agent. Short interfering RNA (siRNA) comprises an RNA duplex that is approximately 19 basepairs long and optionally further comprises one or two single-stranded overhangs. An siRNA may be formed from two RNA molecules that hybridize together, or may alternatively be generated from a single RNA molecule that includes a self-hybridizing portion. It is generally preferred that free 5' ends of siRNA molecules have phosphate groups, and free 3' ends have hydroxyl groups. The duplex portion of an siRNA may, but typically does not, contain one or more bulges consisting of one or more unpaired nucleotides. One strand of an siRNA includes a portion that hybridizes with a target transcript. In certain preferred embodiments of the invention, one strand of the siRNA is precisely complementary with a region of the target transcript, meaning that the siRNA hybridizes to the target transcript without a single mismatch. In other embodiments of the invention one or more mismatches between the siRNA and the targeted portion of the target transcript may exist. In most embodiments of the invention in which perfect complementarity is not achieved, it is generally preferred that any mismatches be located at or near the siRNA termini.

Short hairpin RNA refers to an RNA molecule comprising at least two complementary portions hybridized or capable of hybridizing to form a double-stranded (duplex) structure sufficiently long to mediate RNAi (typically at least 19 base pairs in length), and at least one single-stranded portion, typically between approximately 1 and 10 nucleotides in length that forms a loop. The duplex portion may, but typically does not, contain one or more bulges consisting of one or more unpaired nucleotides. As described further below, shRNAs are thought to be processed into siRNAs by the conserved cellular RNAi machinery. Thus shRNAs are precursors of siRNAs and are, in general, similarly capable of inhibiting expression of a target transcript.

In describing siRNAs it will frequently be convenient to refer to sense and antisense strands of the siRNA. In general, the sequence of the duplex portion of the sense strand of the siRNA is substantially identical to the targeted portion of the target transcript, while the antisense strand of the siRNA is substantially complementary to the target transcript in this region as discussed further below. Although shRNAs contain a single RNA molecule that self-hybridizes, it will be appreciated that the resulting duplex structure may be considered to comprise sense and antisense strands or portions. It will therefore be convenient herein to refer to sense and antisense strands, or sense and antisense portions, of an shRNA, where the antisense strand or portion is that segment of the molecule that forms or is capable of forming a duplex and is substantially complementary to the targeted portion of the target transcript, and the sense strand or portion is that segment of the molecule that forms or is capable of forming a duplex and is substantially identical in sequence to the targeted portion of the target transcript.

For purposes of description, the discussion below may refer to siRNA rather than to siRNA or shRNA. However, as will be evident to one of ordinary skill in the art, teachings relevant to the sense and antisense strand of an siRNA are generally applicable to the sense and antisense portions of the stem portion of a corresponding shRNA. Thus in general the considerations below apply also to shRNAs.

An siRNA agent is considered to be targeted to a target transcript for the purposes described herein if 1) the stability of the target transcript is reduced in the presence of the siRNA or shRNA as compared with its absence; and/or 2) the siRNA or shRNA shows at least about 90%, more preferably at least about 91%, 92%, 93%, 94%, 95%, 96%, 97%, 98%, 99%, or 100% precise sequence complementarity with the target transcript for a stretch of at least about 15, more preferably at least about 17, yet more preferably at least about 18 or 19 to about 21-23 nucleotides; and/or 3) one strand of the siRNA or one of the self-complementary portions of the shRNA hybridizes to the target transcript under stringent conditions for hybridization of small (<50 nucleotide) RNA molecules in vitro and/or under conditions typically found within the cytoplasm or nucleus of mammalian cells. Since the effect of targeting a transcript is to reduce or inhibit expression of the gene that directs synthesis of the transcript, an siRNA, shRNA, targeted to a transcript is also considered to target the gene that directs synthesis of the transcript even though the gene itself (i.e., genomic DNA) is not thought to interact with the siRNA, shRNA, or components of the cellular silencing machinery. Thus in some embodiments, an siRNA, shRNA, that targets a transcript is understood to target the gene that provides a template for synthesis of the transcript.

In some embodiments, an siRNA agent can inhibit expression of a polypeptide (e.g., a protein). Exemplary polypeptides include, but are not limited to, matrix metallopeptidase 9 (MMP-9), neutral endopeptidase (NEP) and protein tyrosine phosphatase 1B (PTP1B).

Growth Factor

In some embodiments, provided silk fibroin-based materials comprise additives, agents, and/or functional moieties, for example, growth factor. In some embodiments, silk fibroin-based materials may release growth factor. In some embodiments, silk fibroin-based materials may release multiple growth factors. In some embodiments growth factor known in the art include, for example, adrenomedullin, angiopoietin, autocrine motility factor, basophils, brain-derived neurotrophic factor, bone morphogenetic protein, colony-stimulating factors, connective tissue growth factor, endothelial cells, epidermal growth factor, erythropoietin, fibroblast growth factor, fibroblasts, glial cell line-derived neurotrophic factor, granulocyte colony stimulating factor, granulocyte macrophage colony stimulating factor, growth differentiation factor-9, hepatocyte growth factor, hepatoma-derived growth factor, insulin-like growth factor, interleukins, keratinocyte growth factor, keratinocytes, lymphocytes, macrophages, mast cells, myostatin, nerve growth factor, neurotrophins, platelet-derived growth factor, placenta growth factor, osteoblasts, platelets, proinflammatory, stromal cells, T-lymphocytes, thrombopoietin, transforming growth factor alpha, transforming growth factor beta, tumor necrosis factor-alpha, vascular endothelial growth factor and combinations thereof.

In some embodiments, provided silk fibroin-based materials comprise additives, agents, and/or functional moieties, for example, that are particularly useful for healing. Exemplary agents useful as growth factor for defect repair and/or healing can include, but are not limited to, growth factors for defect treatment modalities now known in the art or later-developed; exemplary factors, agents or modalities including natural or synthetic growth factors, cytokines, or modulators thereof to promote bone and/or tissue defect healing. Suitable examples may include, but not limited to 1) topical or dressing and related therapies and debriding agents (such as, for example, Santyl® collagenase) and Iodosorb® (cadexomer iodine); 2) antimicrobial agents, including systemic or topical creams or gels, including, for example, silver-containing agents such as SAGs (silver antimicrobial gels), (CollaGUARD™ Innocoll, Inc) (purified type-I collagen protein based dressing), CollaGUARD Ag (a collagen-based bioactive dressing impregnated with silver for infected wounds or wounds at risk of infection), Derma-SIL™ (a collagen-synthetic foam composite dressing for deep and heavily exuding wounds); 3) cell therapy or bioengineered skin, skin substitutes, and skin equivalents, including, for example, Dermograft (3-dimensional matrix cultivation of human fibroblasts that secrete cytokines and growth factors), Apligraf® (human keratinocytes and fibroblasts), Graftskin® (bilayer of epidermal cells and fibroblasts that is histologically similar to normal skin and produces growth factors similar to those produced by normal skin), TransCyte (a Human Fibroblast Derived Temporary Skin Substitute) and Oasis® (an active biomaterial that comprises both growth factors and extracellular matrix components such as collagen, proteoglycans, and glycosaminoglycans); 4) cytokines, growth factors or hormones (both natural and synthetic) introduced to the wound to promote wound healing, including, for example, NGF, NT3, BDGF, integrins, plasmin, semaphoring, blood-derived growth factor, keratinocyte growth factor, tissue growth factor, TGF-alpha, TGF-beta, PDGF (one or more of the three subtypes may be used: AA, AB, and B), PDGF-BB, TGF-beta 3, factors that modulate the relative levels of TGFβ3, TGFβ1, and TGFβ2 (e.g., Mannose-6-phosphate), sex steroids, including for example, estrogen, estradiol, or an oestrogen receptor agonist selected from the group consisting of ethinyloestradiol, dienoestrol, mestranol, oestradiol, oestriol, a conjugated oestrogen, piperazine oestrone sulphate, stilboestrol, fosfesterol tetrasodium, polyestradiol phosphate, tibolone, a phytoestrogen, 17-beta-estradiol; thymic hormones such as Thymosin-beta-4, EGF, HB-EGF, fibroblast growth factors (e.g., FGF1, FGF2, FGF7), keratinocyte growth factor, TNF, interleukins family of inflammatory response modulators such as, for example, IL-10, IL-1, IL-2, IL-6, IL-8, and IL-10 and modulators thereof; INFs (INF-alpha, -beta, and -delta); stimulators of activin or inhibin, and inhibitors of interferon gamma prostaglandin E2 (PGE2) and of mediators of the adenosine 3',5'-cyclic monophosphate (cAMP) pathway; adenosine A1 agonist, adenosine A2 agonist or 5) other agents useful for wound healing, including, for example, both natural or synthetic homologues, agonist and antagonist of VEGF, VEGFA, IGF; IGF-1, proinflammatory cytokines, GM-CSF, and leptins and 6) IGF-1 and KGF cDNA, autologous platelet gel, hypochlorous acid (Sterilox® lipoic acid, nitric oxide synthase3, matrix metalloproteinase 9 (MMP-9), CCT-ETA, alphavbeta6 integrin, growth factor-primed fibroblasts and Decorin, silver containing wound dressings, Xenaderm™, papain wound debriding agents, lactoferrin, substance P, collagen, and silver-ORC, placental alkaline phosphatase or placental growth factor, modulators of hedgehog signaling, modulators of cholesterol synthesis pathway, and APC (Activated Protein C), keratinocyte growth factor, TNF, Thromboxane A2, NGF, BMP bone morphogenetic protein, CTGF (connective tissue growth factor), wound healing chemokines, decorin, modulators of lactate induced neovascularization, cod liver oil, placental alkaline phosphatase or placental growth factor, and thymosin beta 4. In certain embodiments, one, two three, four, five or six agents useful for wound healing may be used in combination. More details can be found in U.S. Pat. No. 8,247,384, the contents of which are incorporated herein by reference.

It is to be understood that agents useful for growth factor for healing (including for example, growth factors and cytokines) encompass all naturally occurring polymorphs (for example, polymorphs of the growth factors or cytokines). Also, functional fragments, chimeric proteins comprising one of said agents useful for wound healing or a functional fragment thereof, homologues obtained by analogous substitution of one or more amino acids of the wound healing agent, and species homologues are encompassed. It is contemplated that one or more agents useful for wound healing may be a product of recombinant DNA technology, and one or more agents useful for wound healing may be a product of transgenic technology. For example, platelet derived growth factor may be provided in the form of a recombinant PDGF or a gene therapy vector comprising a coding sequence for PDGF.

In some embodiments, provided silk fibroin-based materials comprise additives, agents, and/or functional moieties, for example, that are particularly useful as diagnostic agents. In some embodiments, diagnostic agents include gases; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

In some embodiments, provided silk fibroin-based materials comprise additives, agents, and/or functional moieties, for example, radionuclides that are particularly useful as therapeutic and/or diagnostic agents. Among the radionuclides used, gamma-emitters, positron-emitters, and X-ray emitters are suitable for diagnostic and/or therapy, while beta emitters and alpha-emitters may also be used for therapy. Suitable radionuclides for forming thermally-responsive conjugates in accordance with the invention include, but are not limited to, $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$Pd, $^{101m}$Rh, $^{119}$Sb, $^{128}$Ba, $^{197}$Hg, $^{211}$At, $^{212}$Bi, $^{212}$Pb, $^{109}$Pd, $^{111}$In, $^{67}$Ga, $^{68}$Ga, $^{67}$Cu, $^{75}$Br, $^{77}$Br, $^{99m}$Tc, $^{14}$C, $^{13}$N, $^{15}$O, $^{32}$P, $^{33}$P, and $^{18}$F. In some embodiments, a diagnostic agent may be a fluorescent, luminescent, or magnetic moiety.

Fluorescent and luminescent moieties include a variety of different organic or inorganic small molecules commonly referred to as "dyes," "labels," or "indicators." Examples include fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase, aequorin and derivatives thereof. Numerous fluorescent and luminescent dyes and proteins are known in the art (see, e.g. U.S. Patent Application Publication No.: 2004/0067503; Valeur, B., "Molecular Fluorescence: Principles and Applications," John Wiley and Sons, 2002; *Handbook of Fluorescent Probes and Research Products*, Molecular Probes, 9$^{th}$ edition, 2002; and *The Handbook—A Guide to Fluorescent Probes and Labeling Technologies*, Invitrogen, 10$^{th}$ edition, available at the Invitrogen web site; both of which are incorporated herein by reference).

Method of Manufacturing Silk Fibroin-Based Materials

In some embodiments, methods of providing, preparing, and/or manufacturing silk fibroin-based materials of the present disclosure include providing a silk solution as described herein.

In some embodiments, methods of providing, preparing, and/or manufacturing silk fibroin-based materials of the present disclosure includes preparing and/or providing a silk fibroin solution comprising modified silk as described herein.

In some embodiments, methods of providing, preparing, and/or manufacturing silk fibroin-based materials of the present disclosure include providing a silk fibroin solution comprising modified silk. In some embodiments, modified silk comprises modified amino acid residues. In some embodiments, a modified tyrosine residue is or comprises covalently modified tyrosine residues (e.g. by addition of one or more pendant groups). In some embodiments, provided silk fibroin-based materials comprise a concentration of such modified silk between about 1% and about 90%. In some embodiments, covalently modified tyrosine residues. In some embodiments, provided silk fibroin-based materials comprise a concentration of such modified silk of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or more.

In some embodiments, methods of providing, preparing, and/or manufacturing silk fibroin-based materials of the present disclosure include modifying a silk fibroin solution or modifying a silk fibroin-based material. In some embodiments, methods of modifying a silk fibroin solution or modifying a silk fibroin-based material include adding, mixing, and/or applying an additive, agent, and/or functional moiety to a silk solution or a silk fibroin-based material. In some embodiments, methods of modifying a silk fibroin solution or modifying a silk fibroin-based material include reacting an additive, agent, and/or functional moiety with a silk solution or a silk fibroin-based material.

In some embodiments, methods of providing, preparing, and/or manufacturing silk fibroin-based materials of the present disclosure includes preparing a silk fibroin solution comprising modified silk. In some embodiments, methods of providing, preparing, and/or manufacturing silk fibroin-based materials of the present disclosure include providing a silk fibroin solution (e.g. an aqueous silk fibroin solution) and modifying the solution. In some embodiments, methods of providing, preparing, and/or manufacturing silk fibroin-based materials of the present disclosure include providing a silk fibroin-based material and modifying the material.

In some embodiments, methods of providing, preparing, and/or manufacturing silk fibroin-based materials of the present disclosure includes providing an aqueous silk fibroin solution and/or providing a silk fibroin-based material. In some particular embodiments, such methods comprise modifying with 4-sulfonic acid. In some particular embodiments, such methods comprise a modifying by a diazonium coupling reaction. In some embodiments, such methods comprise modifying with poly-lysine. In some particular embodiments, such methods comprise modifying with 4-(heptyloxy)aniline. In some particular embodiments, such methods comprise modifying with 4'-aminoacetophenone.

In some embodiments, methods of providing, preparing, and/or manufacturing silk fibroin-based materials of the present disclosure include preparing and/or providing a silk fibroin solution comprising between about 1% and about 75% modified silk (e.g. in some embodiments, tyrosine residues that are covalently modified by an addition of one or more pendant groups). In some embodiments, preparing and/or providing such a solution comprises mixing a silk solution comprised of modified silk with an unmodified silk solution.

In some embodiments, methods of providing, preparing, and/or manufacturing silk fibroin-based materials of the present disclosure includes mixing silk solutions as described herein with a plasticizer. In some embodiments, mixing a silk solution and a plasticizer yields a solution with a weight ratio of plasticizer to silk between about 5% and about 80%. In some embodiments, mixing a silk solution and a plasticizer yields a solution with a weight ratio of plasticizer to silk of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or more.

In some embodiments, methods of providing, preparing, and/or manufacturing silk fibroin-based materials of the present disclosure includes lyophilizing a silk fibroin solution. In some embodiments, methods of providing, preparing, and/or manufacturing silk fibroin-based materials of the present disclosure includes controlled lyophilizing over a period and/or slow freezing. In some embodiments, controlled lyophilizing over a period and/or slow freezing is used for generating porous structures within silk fibroin matrices. While not wishing to be bound to a particular theory, in some embodiments, a rate dictates how ice crystals form, which ultimately affects the morphology and mechanical properties of provided silk fibroin-based materials. In some embodiments, controlled lyophilizing over a period and/or slow freezing forms silk fibroin-based materials have evenly spaced, interconnected, rounded pore morphology.

In some embodiments, methods of providing, preparing, and/or manufacturing silk fibroin-based materials of the present disclosure includes controlled lyophilizing over a period and/or slow freezing to a target temperature. In some embodiments, a target temperatures is between about −20° C. or about −50° C. In some embodiments, a target temperatures is at least colder that the glass transition temperature of silk. In some embodiments, a target temperature is: at least about −20° C., at least about −25° C., at least about −30° C., at least about −35° C., at least about −40° C., at least about −450° C., or at least about −50° C.

In some embodiments, methods of providing, preparing, and/or manufacturing silk fibroin-based materials of the present disclosure includes controlled lyophilizing over a period and/or slow freezing at fixed or variable rate. In some embodiments, a shelf temperature is cooled according to a fixed or variable rate. In some embodiments, cooling at such a rate occurs until a target temperature is reached. In some embodiments, a time to reach a target temperature, for example, is between about 10 and about or 20 hours.

In some embodiments, methods of providing, preparing, and/or manufacturing silk fibroin-based materials of the present disclosure include controlled lyophilizing over a period and/or slow freezing at a rate of between about −1.0° C./min and about 0.001° C./min. In some embodiments, methods of providing, preparing, and/or manufacturing silk fibroin-based materials of the present disclosure include controlled lyophilizing over a period and/or slow freezing at a rate of about: less than about −1.0° C./min, less than about −0.09° C./min, less than about −0.08° C./min, less than about −0.07° C./min, less than about −0.06° C./min, less than about −0.05° C./min, less than about −0.04° C./min, less than about −0.03° C./min, less than about −0.02° C./min, less than about −0.01° C./min, less than about −0.009° C./min, less than about −0.008° C./min, less than about −0.007° C./min, less than about −0.006° C./min, less than about −0.005° C./min, less than about −0.004° C./min, less than about −0.003° C./min, less than about −0.002° C./min, or less than about −0.001° C./min.

In some embodiments, methods of providing, preparing, and/or manufacturing silk fibroin-based materials of the present disclosure include providing a container that possesses an optimized geometry such that a volume of a provided silk solution uniformly freezes during lyophilization. In some embodiments, a container is thermally conductive. In some embodiments, a container has a thermal conductivity equivalent to or greater than: 167 W/m-K (metric) or 1160 BTU-in/hr-ft$^2$-° F. (English). In some embodiments, for example, a container is made of: alumina, aluminum, beryllia, brass, copper, gold, iron, silver, tungsten, and/or zinc.

In some embodiments, methods of providing, preparing, and/or manufacturing silk fibroin-based materials of the present disclosure includes immersing provided silk fibroin-based materials in methanol after lyophilization to form silk fibroin-based materials that are substantially insoluble in water. In some embodiments, silk fibroin-based materials containing 0-15% (w/w) glycerol were immersed in 90% (v/v) methanol for 1 hour and dried in a fume hood for 12 hours. In some embodiments, materials containing at least 20% (w/w) glycerol were insoluble in water without the methanol treatment.

EXEMPLIFICATION

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1

The present example describes a silk material that rapid re-swelling after deformation triggered by the presence of aqueous media like water or PBS in accordance with some embodiments of the present disclosure.

Methodology:

Cocoons of *Bombyx mori* were boiled for either 10 or 20 minutes in an aqueous solution of 0.02 M sodium carbonate and then rinsed with pure water. The extracted silk fibroin was dried for 12 hours in a chemical hood before being dissolved in 9.3 M LiBr solution at 60° C. for 4 hours, yielding a 20% (w/v) solution. This solution was dialyzed against distilled water using Pierce Slide-a-Lyzer cassettes, MWCO 3500 Da (Rockford, Ill.) for 3 days to remove LiBr. The solution was centrifuged to remove aggregates that formed during purification. The final concentration of aqueous silk fibroin was between 6-8% (w/v). This concentration was diluted with pure water down to 3% (w/v) for all experiments.

Figure 2:
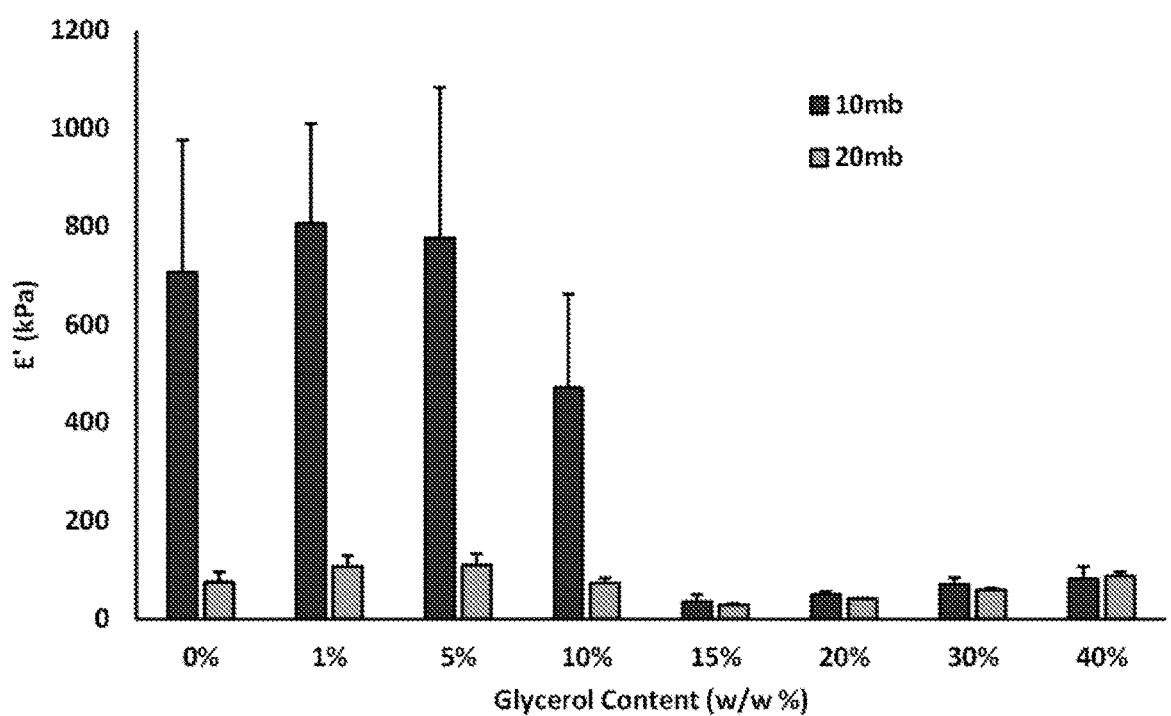
FIG. 2 shows a storage modulus of foams derived from silk boiled for 10 minutes vs. 20 minutes. Boil time of cocoons impacts the molecular weight of purified fibroin. Shorter boil times result in higher molecular weight. In foams containing 10% (w/w) glycerol or less, higher molecular weight fibroin incurs a significantly larger storage modulus compared to lower molecular weight fibroin. This can be used to create foams with specific mechanical properties tailored for various tissue regeneration or therapeutic applications.

The boil time impacts the molecular weight of the silk fibroin, and the molecular weight has shown to impact the storage modulus of the resulting foams (FIG. 2). So far, only 10 and 20 minute boil silk has been tested, but it is expected that higher molecule weight silk (from 5 minute boil) or lower molecular weight silk (from 30 or 60 minute boil) will produce harder or softer foams, respectively. It is undetermined as to how the molecular weight will impact swelling and deformation recovery.

Preparation of Plasticizer/Silk Fibroin Blends

Figure 3:
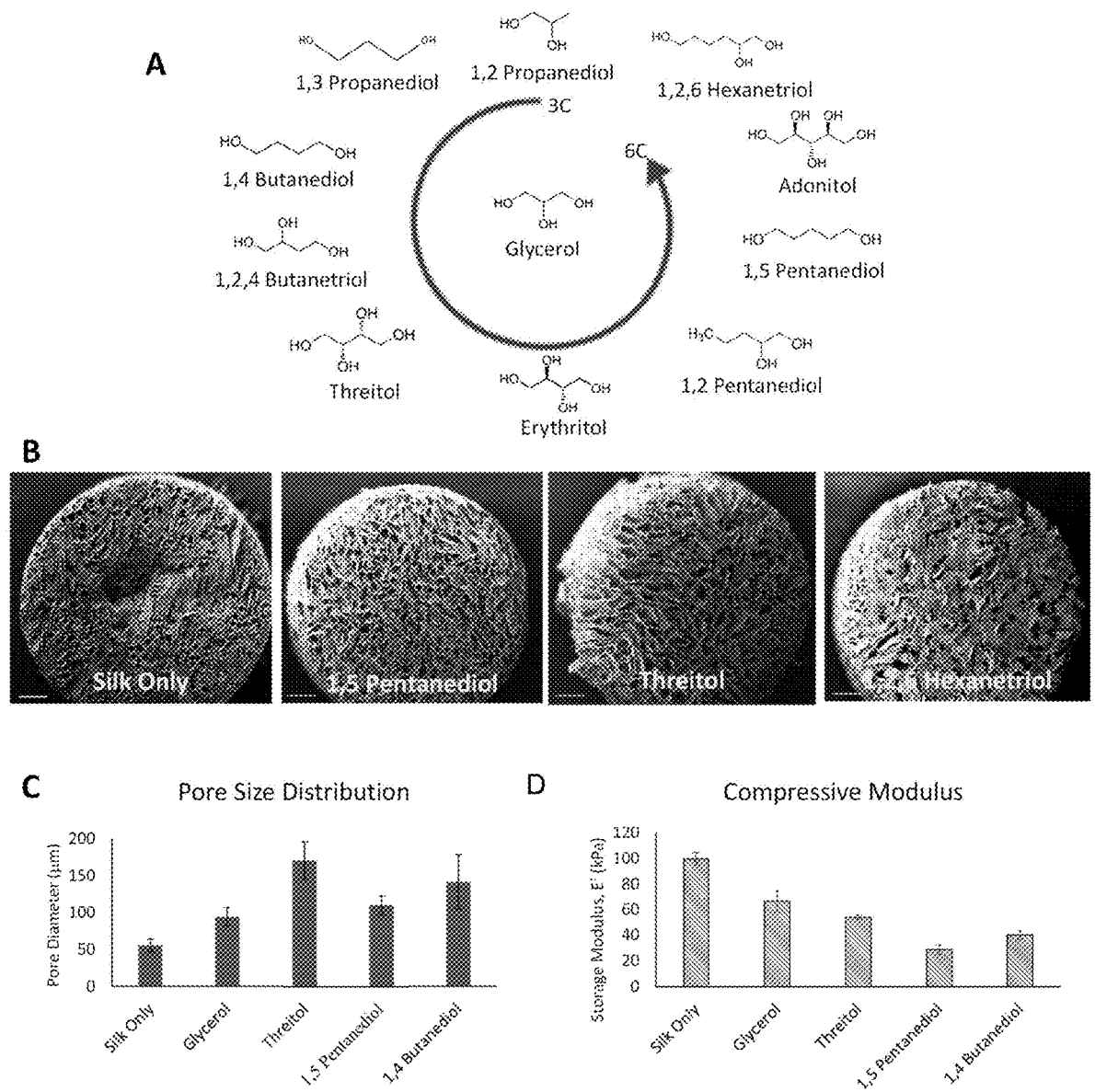
FIG. 3 shows different polyol additives that act as plasticizers in silk foams, imparting shape memory and elastomeric characteristics.

Several polyol plasticizers have been used as additives, agents, and/or functional moieties to make silk memory foams with unique physical characteristics. Each polyol differs slightly in molecular composition, which as a result produces silk foams with varying pore morphologies and storage moduli (FIG. 3). Current work has focused predominantly on glycerol, however, some preliminary data has been collected using other polyols such as threitol, 1,5 pentanediol, 1,3 propanediol and 1,2,6 hexanetriol. Future work will focus on selecting only those polyols which are considered non-toxic in order to preserve the biocompatible nature of these foams.

To make silk/glycerol foams, an aqueous glycerol solution was mixed with purified silk fibroin solution at weight ratios of 0, 1, 5, 10, 15, 20, 30 and 40% (w glycerol/w silk).

Freeze-Dry Processing

A controlled lyophilization method was used for generating porous structures within silk fibroin matrices. Unlike other freeze-dry methods which focus on quickly freezing silk solutions in a constant temperature environment (lab freezer or chest freezer) and allowing samples to sit at temperature for several days, this new process utilizes a highly controlled slow-freeze process that affects foam porosity, pore morphology, swelling kinetics and mechanical strength.

Silk/glycerol solutions were frozen in a lyophilizer at either $-20°$ C. or $-50°$ C. Silk solutions can be frozen anywhere within this range to make shape memory foams. The only limitations on freezing temperature are the glass transition temperature of aqueous silk (must be below this temperature to get proper solidification) and the ability of the freezer (the lab lyophilizer cannot consistently maintain temperatures lower than $-50°$ C.). Therefore, these two temperatures were chosen as the extremes.

Figure 4:
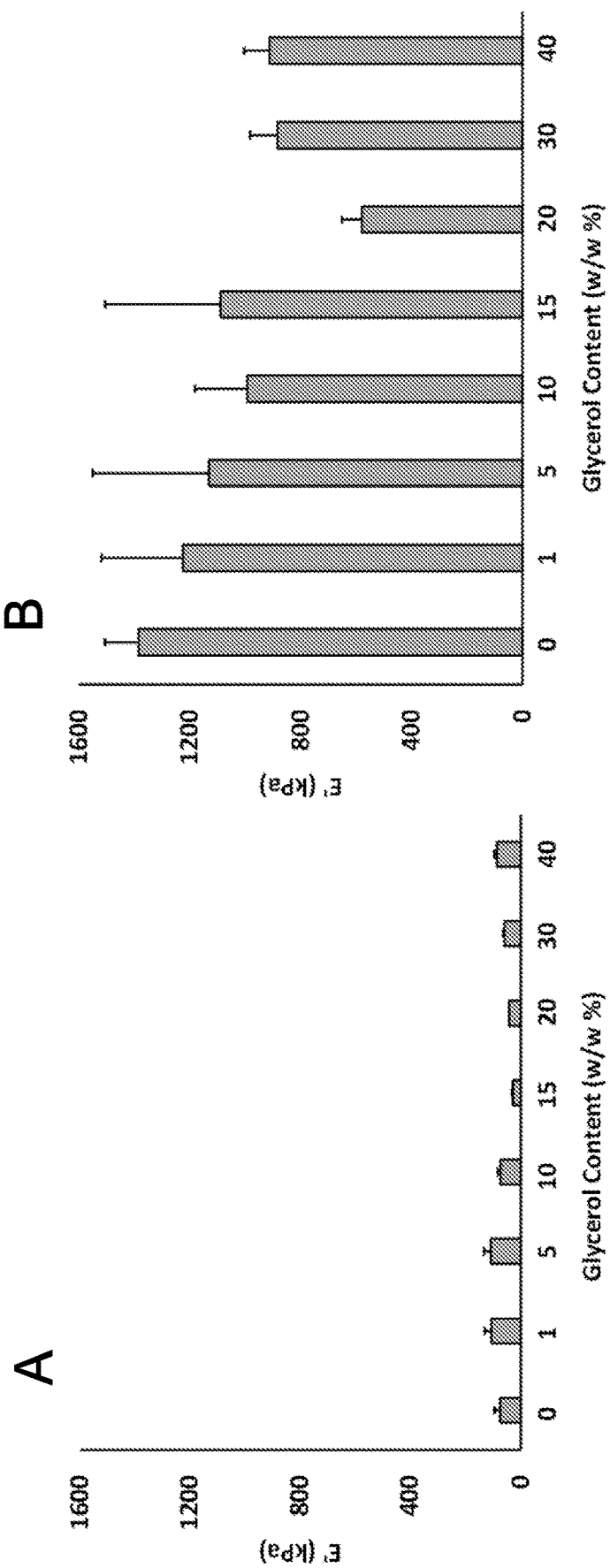
FIG. 4 shows a storage modulus.

The shelf temperature was cooled at a fixed rate of $-0.05°$ C./min until the target temperature was reached, which took either 10 or 20 hours for $-20°$ C. and $-50°$ C., respectively. The freezing rate is highly important as it dictates how ice crystals form, which ultimately affects the morphology and mechanical properties of the foams (FIG. 4). Controlled slow freezing will result in an evenly spaced, interconnected, rounded pore morphology in foams. Fast freezing is accomplished by setting the shelf temperature to the target temperature, which results in the solution freezing in less than an hour. Fast freezing causes ice crystals to grow in random shapes and sizes, creating an unpredictable array of different pore geometries. Future work will focus on determining how different fixed freezing rates (e.g. $-0.01°$ C. or $-0.1°$ C.) will impact the mechanical and morphological features of shape memory silk foams.

Custom Mold Design

Figure 5:
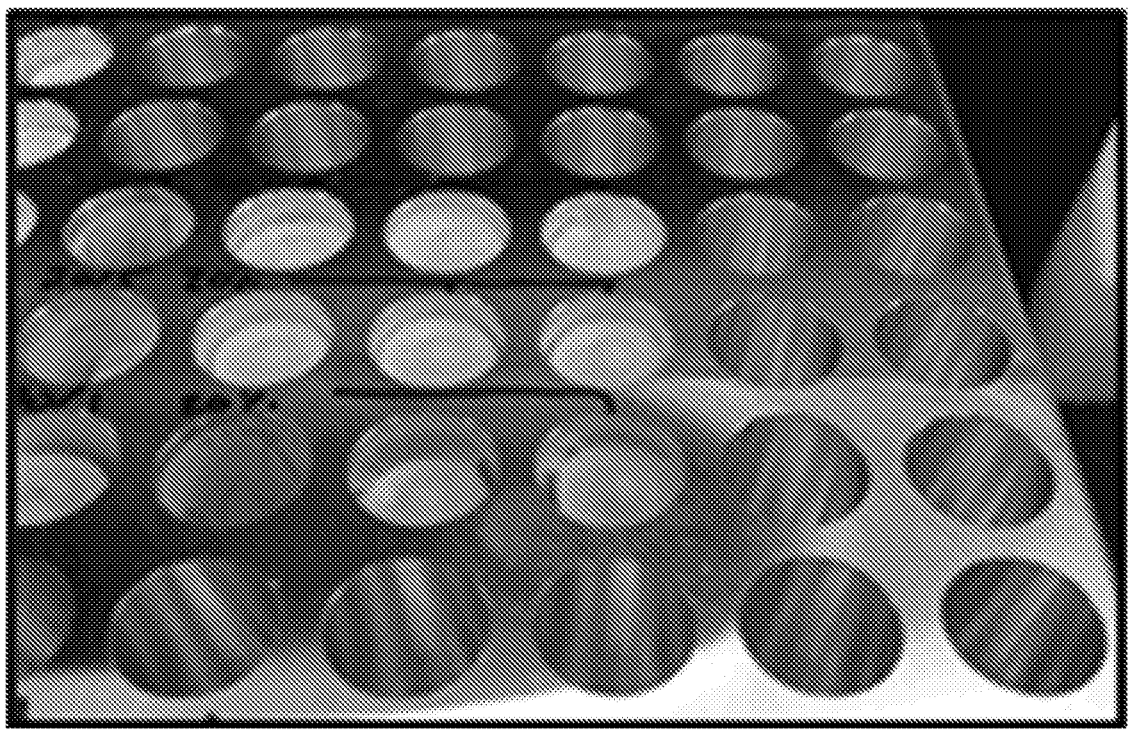
FIG. 5 shows a custom build aluminum mold. In some embodiments, for example a well is 12 mm (dia)×20 mm (depth), and holds approximately 2 mL of solution. The high thermal conductivity of aluminum allows for fine control over the temperature of the solution during freezing, which ultimately impacts the crystallization of water and therefore the porosity and pore geometry within the foams.

Silk/glycerol blends were frozen in a custom designed aluminum mold (FIG. 5). The plate holds 380 wells for making large batches of foams, and each well has a diameter of 12 mm and depth of 20 mm.

Figure 6:
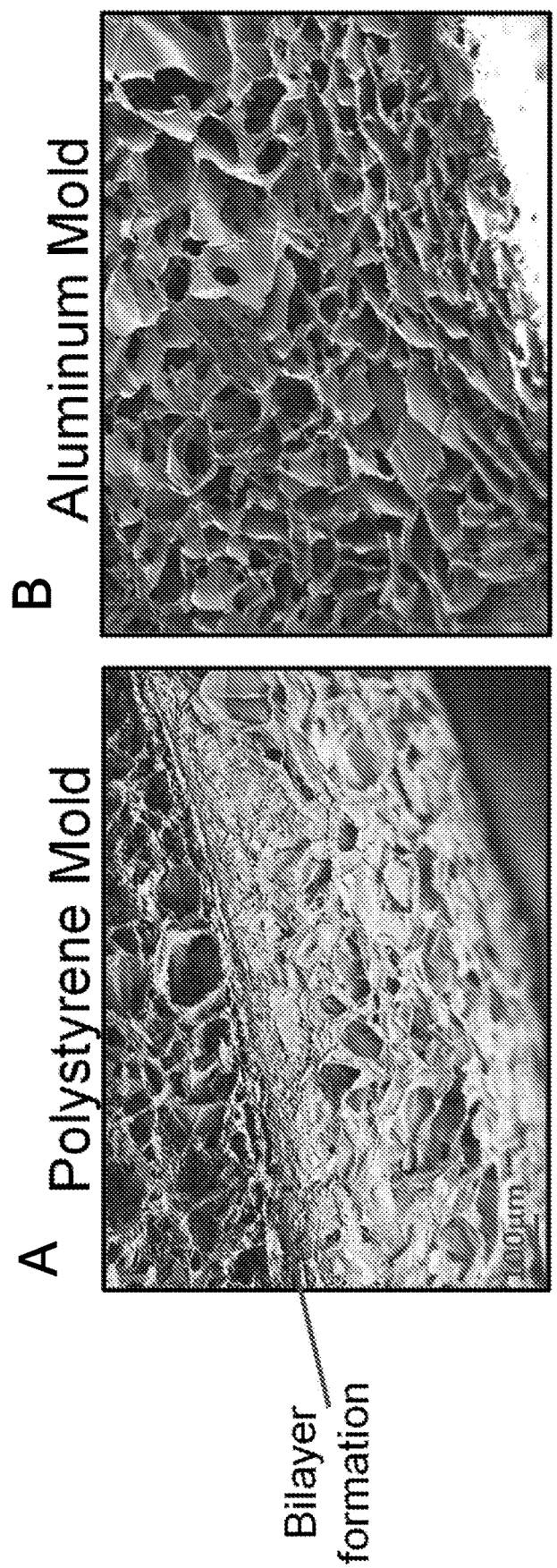
FIG. 6 shows SEM images of materials.

Unlike previous freeze-drying methods that utilized polystyrene well plates to mold foams, the aluminum's high thermal conductivity allows for better control over the temperature of the silk solution. Plastic, which does not conduct heat, results in the silk solution being warmer than the set-point of the shelf. This causes inconsistencies in how the solution freezes. For example, plastic molds typically cause a bilayer to form where half the foam has rounded pores and half contains a heterogeneous distribution of pore sizes and geometries. Aluminum does not create a bilayer, but instead produces rounded pores throughout the entire foam (FIG. 6).

Post-Processing

After lyophilization, all foams containing 0-15% (w/w) glycerol were immediately immersed in 90% (v/v) methanol for 1 hour and dried in a fume hood for 12 hours. Foams containing 20% (w/w) glycerol or more were split into two groups: 1) methanol treatment for 1 hour and 12 hour dry, and 2) no post-processing treatment. Methanol treatment was used to make the foams insoluble in water, but it was observed that foams containing 20% (w/w) glycerol or more were insoluble in water without the methanol treatment.

Results: Swelling, Mechanics and Pore Morphology

Figure 7:
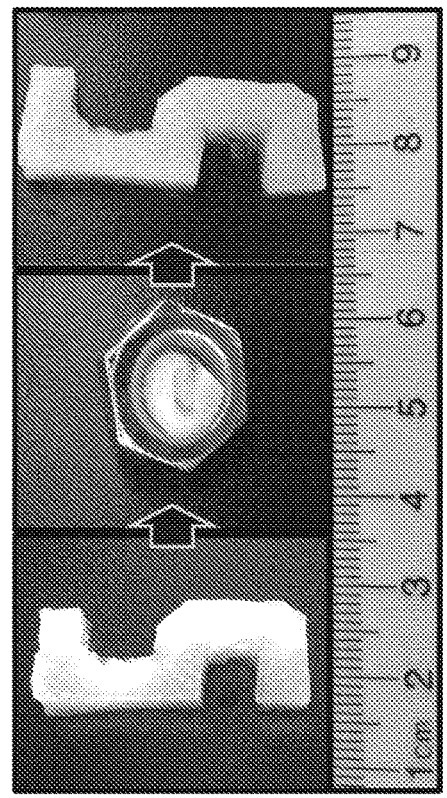
FIG. 7 shows shape memory silk foams that retain their original shape after extensive compression. Here, a foam with complicated geometry, approximately 3 cm long by 1 cm width is rolled up, dried and inserted into the inner diameter of a ½ inch hex nut. Immediately upon immersion in PBS, the foam recovers to its original shape and size.
Figure 8:
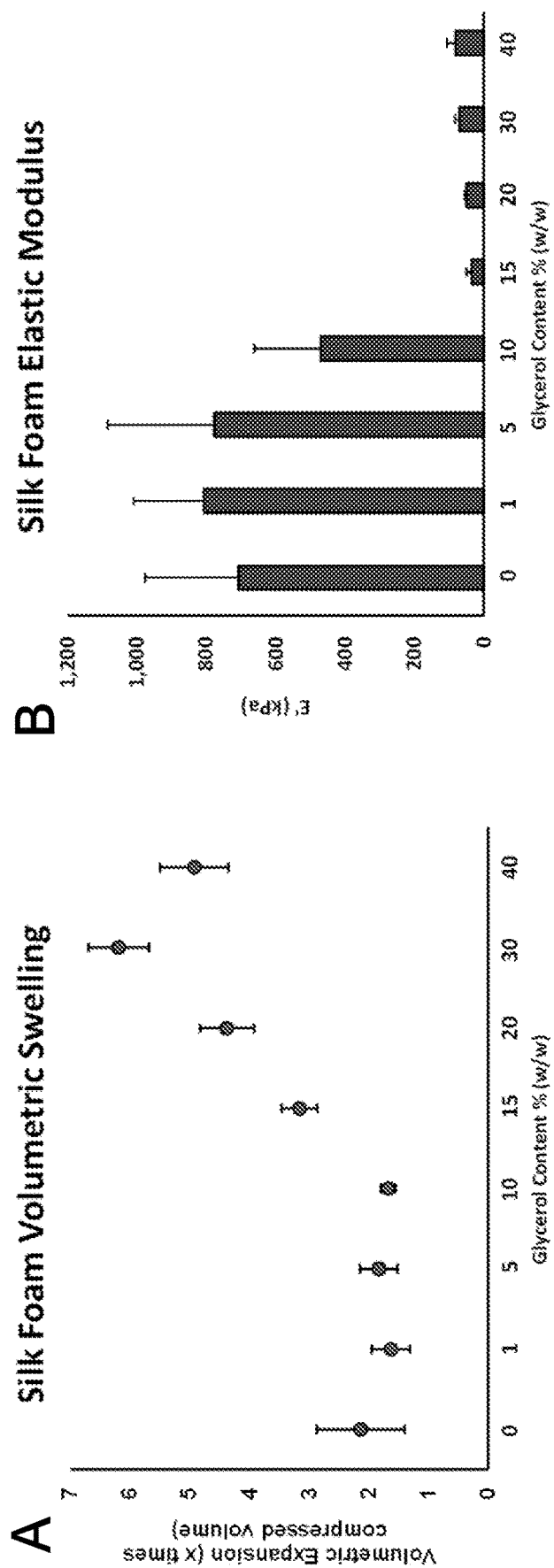
FIG. 8 shows swelling and elastic modulus data for shape memory silk foams.

Swelling was quantified by measuring both mass and volume of foams before after compression. To simulate injection, sponges were compressed to 90% strain (or 10% of their original height) and submerged in PBS. Swelling was calculated by measuring both the mass and dimensions of samples before and after submersion in PBS, thereby measuring PBS absorption. After compression, the silk only (controls) sponges swelled approximately 400% of their starting mass, but exhibited plastic deformation and incomplete recovery to their original volume. Silk sponges with glycerol swelled over 800% of their starting mass and exhibited almost complete recovery of their initial volume (FIG. 7). Volume expansion from the compressed state for silk only sponges was approximate 2×, while sponges with glycerol was about 6×. (FIG. 8, Left).

Stiffness of silk sponges with plasticizer ranged from approximately 7.5 kPa to 810 kPa after expansion in PBS, a range which is suitable for reconstruction of a variety of soft tissues. Mechanical stiffness can be tuned by varying the molecular weight of silk, the glycerol content and by methanol treatment time (no treatment vs. 1 hour methanol treatment). In FIG. 8, Right, by tuning glycerol content alone, the elastic modulus can range by more than an order of magnitude, from approximately 35 kPa to 810 kPa.

Sponges had pore diameters between 100-200 μm, which is large enough to accommodate the infiltration of cells into the bulk material. Furthermore, pore size and shape was not compromised by compression in certain silk/glycerol foam formulations. Pore size and geometry can be tuned via the controlled freeze-dry process by altering the rate of freezing.

Results: In Vivo Degradation

Figure 9:
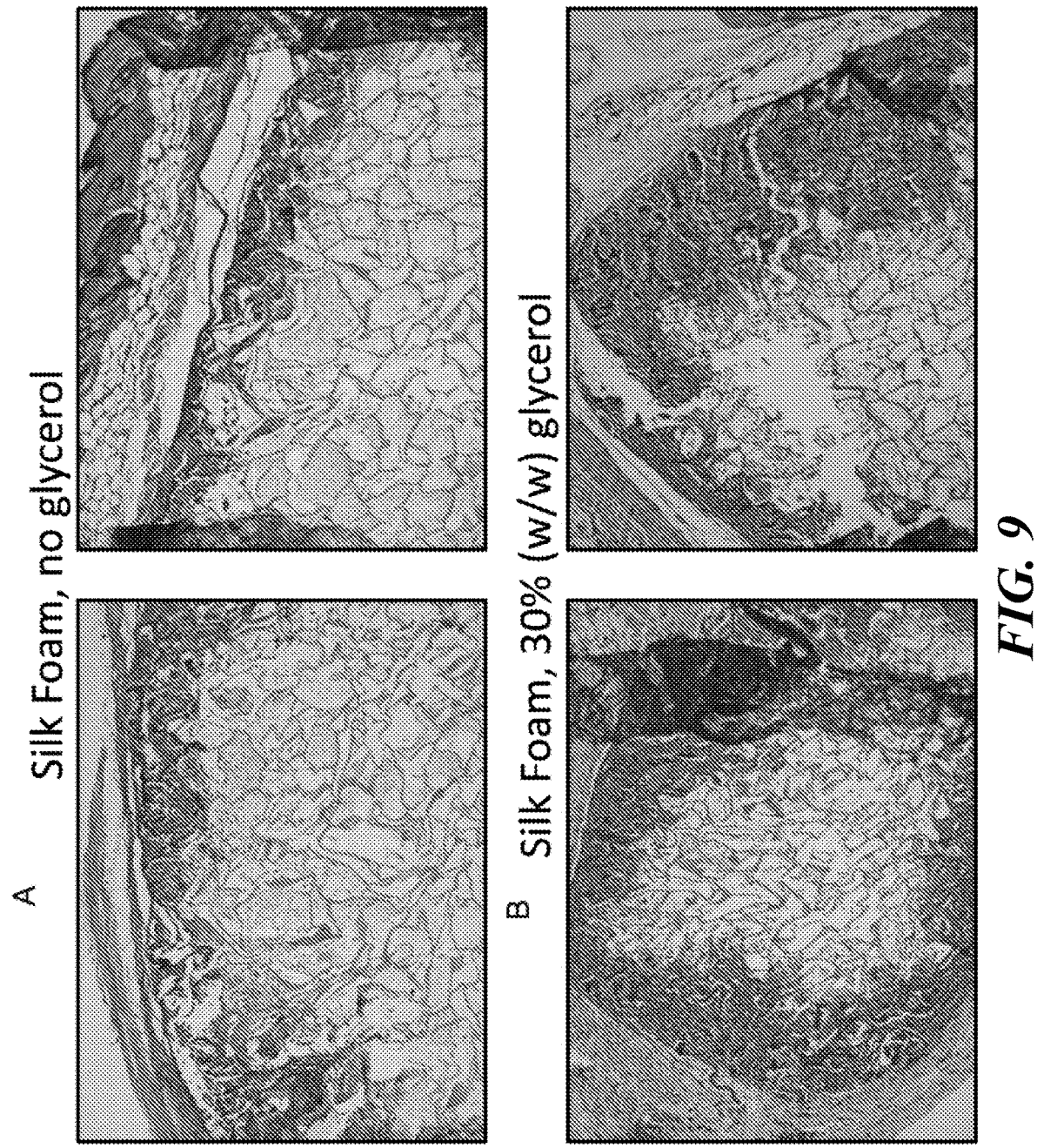
FIG. 9 shows histology of foams recovered after 8 week subcutaneous implantation in mice.

Subcutaneous implantation of silk only (control) and silk-glycerol foams into mice was performed to observe any inflammatory response that may occur as a result of the materials or processing methods. Foams were sterilized via ethylene oxide gas and implanted after being fully-hydrated. Histological analysis of recovered materials after 2, 4, 8 and 12 weeks show that there is minimal immune response in both groups, but extensive cell infiltration and material degradation in silk-glycerol foams only (FIG. 9). These are ideal qualities as degradation and cell infiltration are required for the resorption of materials and replacement by natural tissue. Future work will determine how to control and tune degradation by altering glycerol concentration, foam density or fibroin molecular weight.

Conclusions

The approach discussed here improves upon the current silk foam technology by providing a material which now can undergo rapid re-swelling after deformation triggered by the presence of aqueous media like water or PBS (materials will stay compressed when dry and only expand after immersion into media). Without the use of a plasticizer molecule and a controlled freeze-dry process, silk foams will generally plastically deform when compressed. This is an unfavorable quality, as a compressed material will exhibit different mechanical properties than the original shape, will be unable to fill a void space in the body, and will prevent cellular infiltration and predictable degradation kinetics. These shape memory silk foams also show comparable or better volumetric swelling, biocompatibility and degradability compared to current memory polymers derived from natural materials and can easily be tuned to satisfy a range of elastic moduli. Because of this, silk memory foams could be used as soft tissue fillers for skin defects, aesthetic enhancements (breast, thigh, butt, etc.) or as resorbable grafts for facial disfigurement. Additionally, the elastomeric properties of silk memory foams also make them viable materials for minimally invasive implantation devices for drug delivery, tissue regeneration or wound clotting.

Example 2

The present example describes a shape memory silk material with sulfonic acid modification in accordance with some embodiments of the present disclosure.

Methodology:

Cocoons of *Bombyx mori* were boiled for either 10 or 20 minutes in an aqueous solution of 0.02 M sodium carbonate and then rinsed with pure water. The extracted silk fibroin was dried for 12 hours in a chemical hood before being dissolved in 9.3 M LiBr solution at 60° C. for 4 hours, yielding a 20% (w/v) solution. This solution was dialyzed against distilled water using Pierce Slide-a-Lyzer cassettes, MWCO 3500 Da (Rockford, Ill.) for 3 days to remove LiBr. The solution was centrifuged to remove aggregates that formed during purification. The final concentration of aqueous silk fibroin was between 6-8% (w/v). This concentration was diluted with pure water down to 3% (w/v) for all experiments.

Preparation of Modified Silk Foams

To make silk/glycerol foams, an aqueous glycerol solution was mixed with purified silk fibroin solution at weight ratios of 0, 10, 20, 30, 40, 50, 60, and 75% (w glycerol/w silk).

Sulfonic acid modification of tyrosine residues within silk fibroin proteins was performed via a diazonium coupling reaction as seen in Murphy et al. See Murphy, Amanda R.; St. John, Peter; Kaplan, David L. Modification of silk fibroin using diazonium coupling chemistry and the effects on hMSC proliferation and differentiation. Biomaterials 2008; 29:2829-2838. The reaction yielded silk solution with approximately 60% of its tyrosine residues modified with sulfonic acid. This solution was blended with unmodified silk solution to produce solutions with less modification (e.g. 10% and 30% modified tyrosine).

After lyophilization, foams were split into 2 groups: 1) methanol treated for 1 hour and 2) no treatment.

Mechanical Testing

Volumetric Swelling: Wetted foam cylinders (4.5 mm diameter) were compressed unilaterally to 10% of their max height. The volume of the foam was measured in compressed state, then submerged in water for 15 seconds. The resulting foam volume was re-measured and a ratio between swollen and compressed volumes was calculated.

Compressive Modulus and Recovery: Foams were loaded onto a Dynamic Mechanical Analysis (DMA) machine and compressed to 80% strain in order to simulate the compression experienced during injection. Compressive modulus was calculated via the slope of the stress-strain curve between 1-2% strains. Peak compressive stress was calculated by measuring the stress at 80% strain. Ramp rate was 1 mm/min.

Results: Swelling, Recovery and Mechanics

It has been observed that the addition of glycerol to freeze-dried silk foams increases elasticity and recovery post compression. In addition, glycerol in high concentrations (>20% w/w) causes silk materials to crystallize, rendering the material insoluble in water. In comparison, silk only foams require post-treatments (e.g. methanol, autoclaving, water annealing) in order to be insoluble in water.

Figure 10:
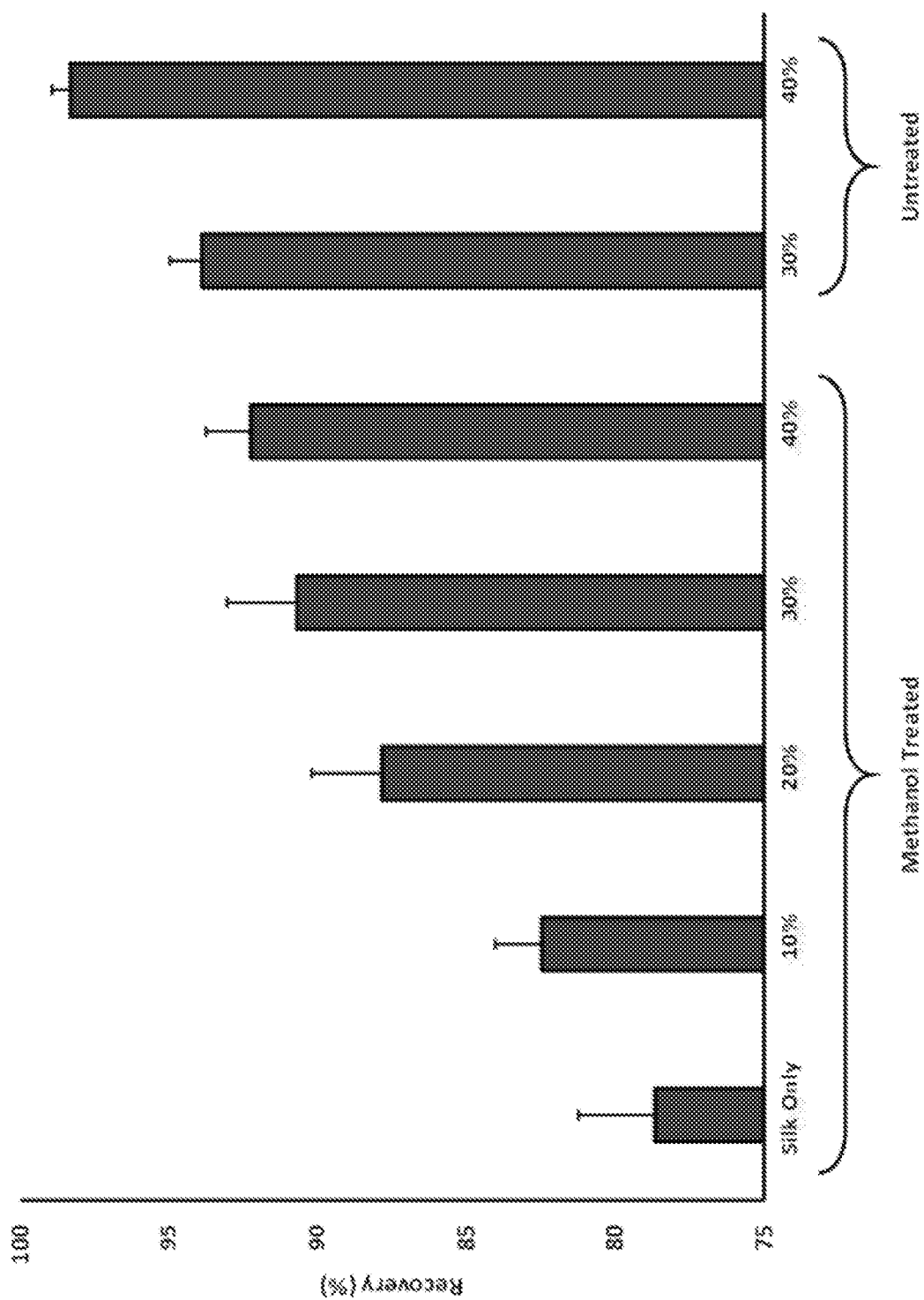
FIG. 10 shows recovery post-compression to 80% strain. Silk foams with and without glycerol were either treated with methanol or left untreated (for high glycerol containing foams only), and the ability to recover back to their original size after severe compression was measured via DMA. As glycerol content increases, foams exhibit higher recovery. For foams containing 40% w/w glycerol without methanol treatment, recovery is almost 100% after compression.

In FIG. 10, silk foams are shown to have improved recovery with increasing concentration of glycerol. In order to have an accurate comparison, foams containing 0% (controls) to 40% w/w glycerol were methanol treated. Silk only control foams recover to about 75-80% of their original volume after compression, whereas >20% w/w glycerol containing foams recover to 90-95%. Without methanol treatment, glycerol containing foams can recover almost 100% of their original volume after severe compression.

With regard to volumetric swelling, silk only controls could expand 2-3× from their compressed volume, while the addition of 30% w/w glycerol allowed improved swelling up to 6-7× the compressed volume. In order to further improve the swelling potential of silk foams, a diazonium coupling reaction was used to modify silk tyrosine residues with sulfonic acid. Sulfonic acid modification was chosen to increase the hydrophilicity of the freeze-dried silk scaffolds. In combination with glycerol, it was believed that these modifications would yield hydrophilic foams capable of absorbing large quantities of water and high volumetric swelling in comparison to silk only controls.

Figure 11:
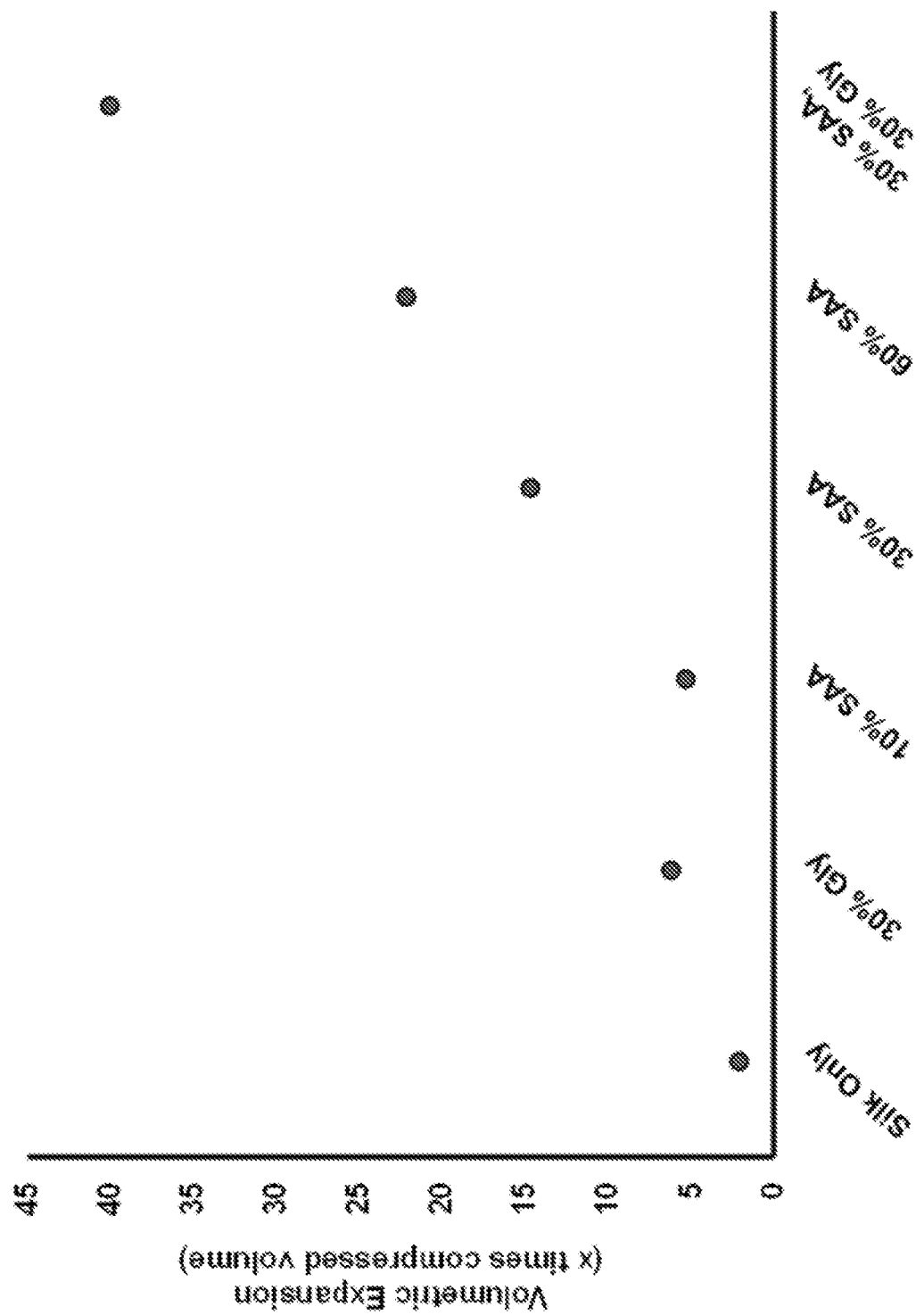
FIG. 11 shows volumetric expansion of foams from a highly compressed state. Addition of glycerol or low sulfonic acid modification yield mild improvements in swelling compared to silk only controls. However, high sulfonic acid modification increases swelling up 20-25×. High sulfonic acid modification with glycerol results in very high swelling after compression, however, the material transforms into a semi-gel state, no longer maintaining a rigid open-celled porous material. SAA=Sulfonic Acid Azosilk modification

In FIG. 11, silk scaffolds modified with 10% sulfonic acid showed no improvement over glycerol-silk foams, however, higher modifications showed improved swelling, greater than 20× the compressed volume. With the addition of glycerol, 30% sulfonic acid modified silk could swell over 40× the compressed volume while maintaining some structure. After swelling, glycerol/30% sulfonic acid modified silk scaffolds turned into amorphous shaped semi-gels with some identifiable solid particles within its polymer network.

Figure 12:
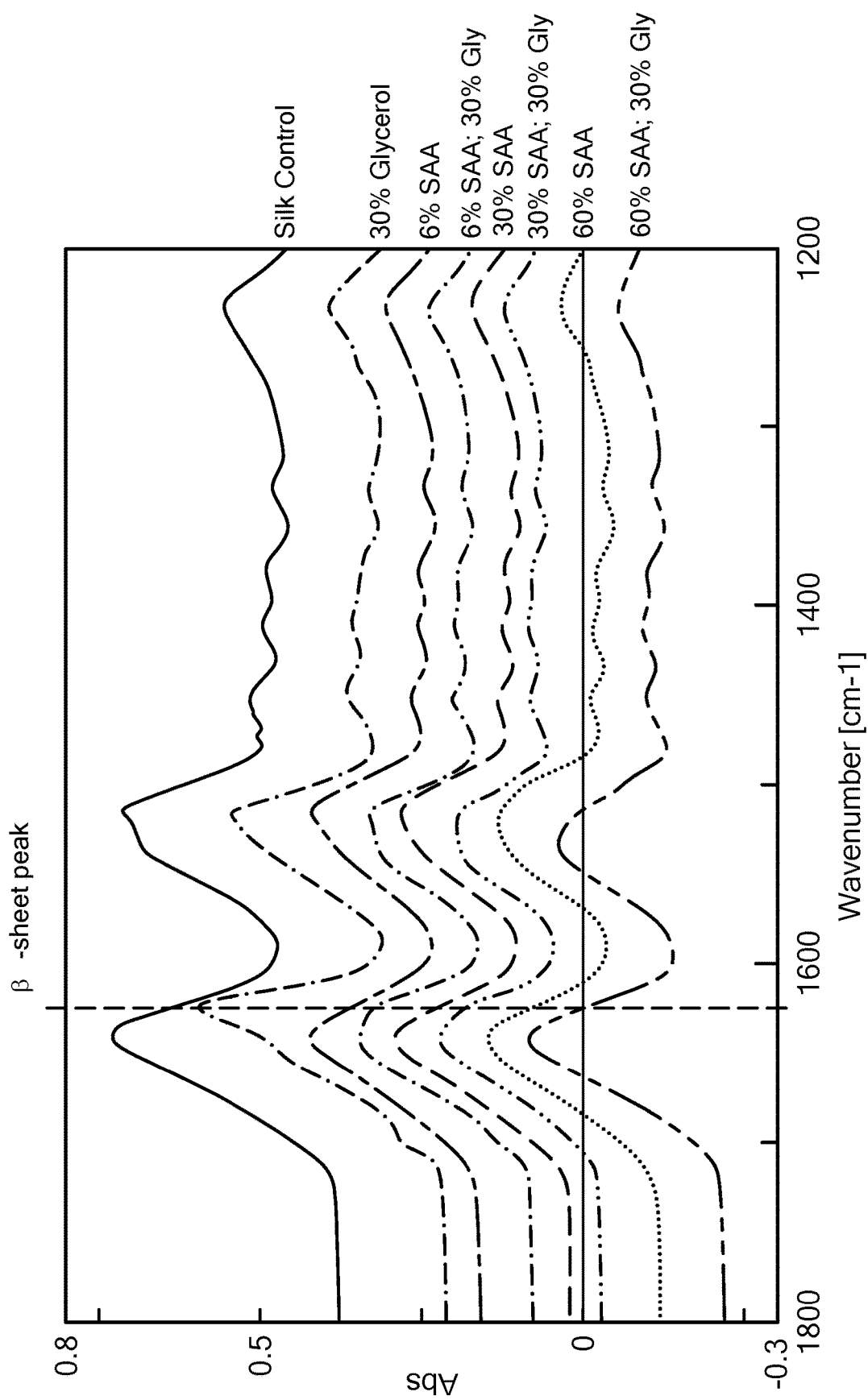
FIG. 12 shows FTIR analysis of the secondary structure of silk only, silk-glycerol and silk-sulfonic acid modified foams. With increasing sulfonic acid modification, the crystallization caused by high glycerol content decreases, resulting in a lower β-sheet structure. SAA=Sulfonic Acid Azosilk modification

Untreated diazonium coupled silk foams without glycerol dissolved in water. As expected, the addition of glycerol prevented dissolution as long as the sulfonic acid modification was not too high. For example, 30% sulfonic acid modified scaffolds containing glycerol did not dissolve, but 60% modified scaffolds with glycerol quickly dissolved in water. It was predicted that the modification of tyrosine residues with hydrophilic chemistries would prevent β-sheet formation in foams with glycerol or methanol treatment. To confirm this, the secondary structure of foams with varying levels of sulfonic acid were compared with and without glycerol present (FIG. 12).

As expected, control foams show predominantly amorphous structure, while silk-glycerol foams have a strong β-sheet peak. In sulfonic acid modified foams, with increasing modification and constant glycerol concentration, the β-sheet peak disappears. This likely explains the ability of the foams to expand while absorbing water. Decreased crystallinity would likely allow higher expansion, to a point at which the foams do not possess enough physical crosslinks to hold together.

Figure 13:
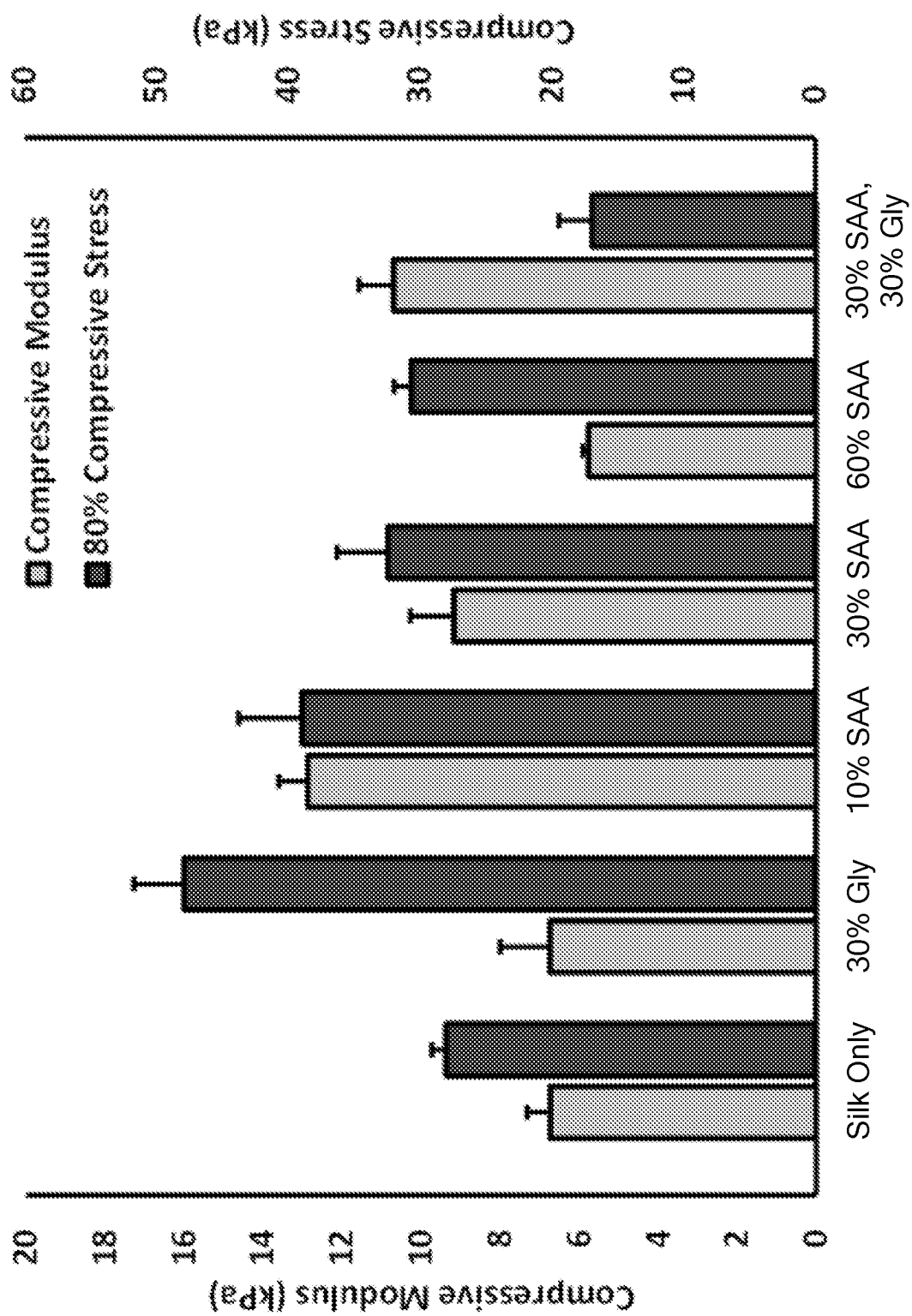
FIG. 13 shows a compressive modulus and compressive stress at 80% strain for modified silk foams. Modified silk foams show comparable mechanical stiffness compared to silk-only controls. The compressive stress at 80% is meant to mimic the stress required to compress a foam during injection via needle. Silk-glycerol foams show significantly increased compressive stress at high compression, however sulfonic azosilk modified foams show decreased compressive stress at high modification. Silk-glycerol/sulfonic acid modified foams require less force for high compression compared to controls, indicating that they may require less force for injectable applications. SAA=Sulfonic Acid Azosilk modification.

Finally, FIG. 13 highlights the mechanical properties of modified foams vs. silk only controls. Silk only, silk-glycerol and silk-sulfonic acid modified foams all possess similar mechanical stiffness. Silk-glycerol/sulfonic acid modified foams which transform into soft gels when fully swollen are nearly as soft as silk only foams, despite the high water retention. Of note, the peak compressive stress at 80% strain is meant to mimic the force required to compress a foam to 20% of its original size, thus simulating the effects of injection. While silk-glycerol foams appear to require greater force for high compression, the silk-sulfonic acid modified foams require comparable force for compression. Furthermore, silk-glycerol/sulfonic acid modified foams require significantly less force for compression, likely due to the amorphous shape of the material. This indicates that modified silk foams may be easier to compress during injection.

Conclusions

The addition of sulfonic acid further modified the shape memory and superabsorbency of these freeze-dried silk-glycerol foams. By tuning both the glycerol content and sulfonic acid modification, control over the crystallinity and thus swelling can be attained. A balance must be made between high swelling and structural integrity. Ideally these foams will be highly porous solids, however, there can also be use for highly absorbent hydrogels.

The resulting foams can achieve better recovery over silk only controls, an order of magnitude greater swelling, and comparable or lower compressive strength at high strains, indicating that they may require less force for injection while still maintaining highly recoverable shape memory properties.

Example 3

The present example describes a silk material that rapid re-swelling after deformation triggered by the presence of aqueous media like water or PBS in accordance with some embodiments of the present disclosure.

Materials & Methods

Preparation of Silk Solutions

Silk fibroin solution was prepared as previously reported. See for example Rockwood, D. N., Preda, R. C., Yücel, T., Wang, X., Lovett, M. L., & Kaplan, D. L., Materials fabrication from Bombyx mori silk fibroin, 6 Nature Protocols 10, 1612-31 (2011). Briefly, silk fibroin protein was extracted from Bombyx mori cocoons by boiling in a 0.02 M sodium carbonate solution for 10, 30 or 60 minutes (hereafter referred to as 10 mE ("minutes extracted"), 30 mE, and 60 mE, respectively) to remove sericin. The extracted silk fibroin was washed and dried for 12 hours in a chemical hood before being dissolved in 9.3 M LiBr solution at 60° C. for 4 hours, yielding a 20% w/v solution. This solution was dialyzed against distilled water using Pierce Slide-a-Lyzer cassettes, MWCO 3500 Da (Rockford, Ill.) for 3 days to remove LiBr. The solution was centrifuged to remove aggregates that formed during purification. The final concentration of aqueous silk fibroin (hereafter referred to as silk) was ~6-8% w/v. This concentration was diluted with deionized water to 3% w/v for all experiments and stored at 2-5° C. until use. For diazonium coupling modifications only, silk solution was additionally dialyzed against borate buffer (100 mM borate, 150 mM sodium chloride, pH 9) (Buph borate buffer packs; Pierce, Woburn Mass.) for 24 hours.

Preparation of Modified Silk Blends

Two methods were employed to fabricate silk sponges with enhanced hydrophilicity and shape memory characteristics. All formulations are summarized in. First, aqueous silk protein was blended with specific polyol additives, such as glycerol (Sigma-Aldrich, St. Louis, Mo.), as described previously. See for example Lu, S., Wang, X., Lu, Q., Zhang, X., Kluge, J., Uppal, N., Kaplan, D. L., Insoluble and flexible silk films containing glycerol, 11 Biomacromolecules 1, 143-50 (2010). Briefly, glycerol solution at 700 mg/mL was added to silk solutions at various weight:weight (w/w) ratios: 1:99, 5:95, 10:90, 15:85, 20:80, 30:70 and 40:60 weight glycerol:weight silk. Solutions were homogenized via gentle inversion until phase separation was no longer visible.

The second method of silk modification was by a diazonium coupling reaction to modify tyrosine residues with sulfanilic acid. See for example, Murphy, A. R., St John, P., & Kaplan, D. L., Modification of silk fibroin using diazonium coupling chemistry and the effects on hMSC proliferation and differentiation, 29 Biomaterials 19, 2829-38 (2008). Briefly, chilled solutions of sulfanilic acid (30 mL in water, 0.065 M) and p-toluenesulfonic acid (7.5 mL, 1.76 M) were vortexed and kept in an ice bath for 10 minutes. Next, sodium nitrite (7.5 mL, 0. M) was added to the solution, vortexed briefly and kept on ice for an additional 30 minutes. Diazonium salt solution was then added to 10 mE silk solution in borate buffer to achieve a theoretical yield of approximately 60% tyrosine modification. Modification of silk protein was confirmed and quantified by spectrophotometric analysis. Absorbance values of modified silk solutions at 325 nm were used to calculate the relative concentration of modified tyrosine residues. Diazonium modified silk solution was diluted in unmodified 10 mE silk solution to achieve blends with 10% and 30% yield of modified tyrosine residues. Solutions were diluted to a 3% w/v silk protein concentration and stored at 2-5° C. for no longer than 24 hours before use. In the figures, diazonium modified sponges are abbreviated to SAA for "sulfonic acid azosilk."

Freeze-Dry Processing and Post-Treatment

A controlled lyophilization method was used for generating homogenously distributed porous structures within silk matrices. Modified silk blends were frozen in a custom designed aluminum mold (FIG. 5). The aluminum mold contained 380 wells (12 mm 0; 20 mm depth) for making large batches of sponges. 1.5 mL aliquots of silk solution were added to each well before being transferred to a VirTis Genesis 25L Super XL Freeze Dryer (SP Scientific, Stone Ridge, N.Y.). Samples were frozen using a modified version of a previously published protocol. See for example Guziewicz, N., Best, A., Perez-Ramirez, B., & Kaplan, D. L., Lyophilized silk fibroin hydrogels for the sustained local delivery of therapeutic monoclonal antibodies, 32 Biomaterials 10, 2642-2650 (2011). Briefly, samples were cooled from ambient temperature and held at 5° C. for 1 hour, then frozen to −45° C. (ramp rate: −0.05° C./min) and held for 12 hours. Primary drying was performed at −20° C. at 50 mT vacuum until the Pirani gauge pressure registered lower than the capacitance manometer pressure. Patel, S. M., Doen, T., & Pikal, M. J., Determination of End Point of Primary Drying in Freeze-Drying Process Control, 11 AAPS PharmSciTech, 1, 73-84 (2010). A secondary drying step was performed at 4° C. for 10 hours.

Post-Processing

Upon completion of lyophilization, sponges containing 0-15% (w/w) glycerol were immediately immersed in 90% (v/v) methanol for 12 hours before being washed and stored in deionized water until testing. Sponges containing 20% (w/w) glycerol or more were post-processed in one of two ways: 1) methanol treatment for 12 hours and storage in deionized water, or 2) directly stored in deionized water with no post-processing methanol treatment. For each group, a subset of samples was removed from deionized water and lyophilized a second time to dry the materials. These samples were stored in closed tubes with desiccant packets at room temperature for image analysis and porosity characterization.

Analytical Techniques

Compressive Modulus, Recovery, Swelling and Fatigue

The mechanical properties of silk sponges were assessed via unconfined compression testing on a TA Instruments RSA3 Dynamic Mechanical Analyzer (TA Instruments, New Castle, Del.). Prior to testing, sponges were cut into a uniform cylindrical size (8 mm Ø; 5 mm height) and rehydrated in 1×PBS under vacuum (approximately 60 kPa vacuum) for 30 minutes to ensure proper hydration throughout the material. Samples were then kept in PBS for 12 hours at room temperature and pressure. After rehydration, sponge samples were loaded between stainless steel parallel plates within an immersion bath containing 1×PBS. All samples were analyzed with an initial preload of 0.5 grams to ensure proper contact between the upper plate and the sample. Each sponge was subjected to a custom macro that measured in sequence the elastic modulus, hysteresis and shape recovery before and after the application of 80% axial strain (20% of initial height) to simulate a demanding physical stress, such as injection. Preceding each test, sponges were pre-conditioned via four cycles to 40% axial strain at 1 mm/min ramp rate and allowed to recover in PBS for 30 minutes before primary testing began. After pre-conditioning, the initial height of the sample was recorded with the applied 0.5 gram preload.

Sponge samples were subjected to the following sequence of tests: 1) load/unload to 20% strain (for pre-compressed modulus; referred as "pre"); 2) load/unload to 80% axial strain (high compression cycle); 3) load/unload to 20% axial strain (for post-compressed modulus; referred to as "post"). The ramp rate was kept constant at 1 mm/min for all tests. The compressive modulus was calculated by the slope of the linear elastic region of each stress-strain curve in the range of 1-5% axial strain. The recovery was calculated by comparing the height of the sponge (with applied 0.5 gram preload) pre vs. post 80% axial strain. Hysteresis was measured as the ratio of the area under the curve between the loading and unloading regions of each strain sweep. For fatigue measurements, storage modulus was monitored on samples under cyclic load at a frequency of 0.5 Hz at either 1, 5 or 10% axial strain for 1000 cycles. Swelling ratios were calculated by measuring the axial and radial dimensions of sponges at a chosen maximal compression (5% initial height; 95% axial strain) and after dehydration by wicking away residual water. Samples were rehydrated in 1×PBS for 30 seconds. Sample volume was re-measured and compared to compressed volume.

Mercury Intrusion Porosimetry

Mercury intrusion porosimetry measurements were conducted to evaluate the porosity and pore size distribution of modified silk sponges after hydration and subsequent lyophilization to dry the material while preserving the hydrated shape. Cylindrical sponge samples (variable size based on degree of swelling) were analyzed via a Quantachrome PoreMaster mercury intrusion porosimeter (Quantachrome Instruments, Boynton Beach, Fla.). For each formulation, five samples were massed and pooled into glass sample cells with a 0.5 cc stem volume. A low pressure cycle (max pressure: 50 psi, or 344 kPa) was performed to evaluate pore sizes within the micrometer range. Results are reported as a histogram of pore size (in µm) vs. a pore size distribution function, FV, where FV=−[dV/d log(D)], V is the cumulative pore volume, and D is the pore diameter.

Fourier Transform-Infrared (FT-IR)

FT-IR and Fourier self-deconvolution (FSD) were used to analyze and quantify the protein secondary structural elements of the silk sponges. Sponges were measured using a JASCO FTIR 6200 spectrometer (JASCO, Tokyo, Japan) combined with a MIRacle™ attenuated total reflection (ATR) germanium crystal. Background and spectral scans were measured from 4000-600 $cm^{-1}$ at a resolution of 2 $cm^{-1}$ for 32 scans per sample. Sponge samples were measured either as processed (immediately after the lyophilization cycle) or after hydration. If hydrated, sponges were dried in an air flow hood for 12 hours and kept under desiccant until analysis to reduce interference from water adsorption. Secondary structure was quantified within the amide I region (1590-1710 $cm^{-1}$) by FSD and peak fitting using Opus 5.0 software (Bruker, Billerica, Mass.). Each raw IR spectra underwent baselining, 9-point smoothing (Savitzky-Golay method) and deconvolution using a Lorentzian line shape with half-bandwidth of 25-26 $cm^{-1}$ and noise reduction factor of 0.3. Apodization was performed via a Blackman Harris function. The deconvoluted amide I region was curve fit with 11 Gaussian line shape profiles as previously described. See for example Hu, X., Kaplan, D., & Cebe, P., Determining beta-sheet crystallinity in fibrous proteins by thermal analysis and infrared spectroscopy, 39 Macromolecules 18, 6161-6170 (2006). Peaks were assigned to specific secondary structural elements based off previous work, see for example Lawrence, B. D., Omenetto, F., Chui, K., & Kaplan, D. L., Processing methods to control silk fibroin film biomaterial features, 43 J. Materials Science 21, 6967-6985 (2008) and relative contributions of each structure were calculated from ratio of the area under the peak relative to the area sum of all fitted peaks.

Differential Scanning Calorimetry

Silk solutions containing varying concentrations of glycerol (0-10% w/w) were diluted to 4% w/v silk protein and analyzed on a TA Instruments G100 differential scanning calorimeter (New Castle, Del.). 10 µL of sample was added to aluminum hermetic pans with lids and sealed using a sample press to reduce evaporation during heating. Temperature-modulated measurements were performed on samples cooled to −45° C. and heated at a rate of 2.0° C./min to 20° C., with a modulation period of 60 s and temperature modulation amplitude of 1±0.318° C. The solution glass transition temperature was determined as the inflection point at sub thermal step changes.

Scanning Electron Microscopy (SEM)

SEM was used to evaluate the pore morphology of modified silk sponges. Silk protein sponges were imaged using a Zeiss EVO MA10 electron microscope (Carl Zeiss AG, Germany). Cylindrical samples were analyzed after hydration and subsequent re-lyophilization. Samples were cut along the horizontal axis, mounted onto copper tape, and sputtered with gold before imaging.

In Vivo Subcutaneous Implantation

All animal studies were conducted under protocols approved by and in compliance to the regulations specified by Tufts University Institutional Animal Care and Use Committee (IACUC) and the National Institute for Health's Office of Laboratory Animal Welfare (OLAW). Balb-C female mice at 6-8 weeks of age were purchased from Charles River Labs (Wilmington, Mass.) and allowed to acclimate for 1 week prior to implantation studies. Animals were anesthetized via inhalation of isoflurane at 3% for induction and maintained at 2% during surgical procedures. All animals were kept on heating pads throughout anesthesia. Silk sponges were sterilized in a wet autoclave cycle for 25 minutes and equilibrated in sterile 1×PBS for 24 hours prior to surgery. Mice were randomly assigned four time points (2, 4, 8 and 12 weeks) with two animals per time point. Each mouse had two types of silk sponge samples (5 mm 0; 3 mm height): 3% w/v silk only and 3% w/v silk containing 30% w/w glycerol (N=4 per group per time point). Sponges were implanted subcutaneously in the scapular and dorsal inguinal regions. At each time point, animals were euthanized and silk sponges were excised along with surrounding tissue for histological examination. The sponge diameter for each sample was measured using calipers, after which the samples were fixed and stored in formalin.

Histochemistry

Excised tissues were fixed in 10% neutral buffered formalin and embedded in paraffin wax following dehydration by xylene and graded ethanol bath. Samples were sectioned, mounted onto glass slides and stained with hematoxylin and eosin (H&E; Sigma-Aldrich, St. Louis, Mo.) to visualize cell infiltration. Samples were imaged using a Zeiss Axiovert 40 CFL light microscope and a 10× objective lens (Carl Zeiss, Germany).

Statistics

Data is expressed as the average±standard deviation. For mechanical data (N=3 per group) and secondary structure analysis (N=3 per group), 1-way ANOVA and Tukey post-hoc analysis for $p<0.05$ were used to determine significance of experimental groups compared to the silk only controls. Significance between the mechanical properties of "pre" and "post" compressed sponges (N=3 per group, dependent sampling) was determined by paired t-test with statistical significance accepted at $p<0.05$. The significance of in vivo degradation was measured via unpaired t-test between silk only controls and silk-glycerol samples (N=4 per group per time point) at each time point for $p<0.05$.

Results

Diazonium Modified Silk Sponges

Figure 14:
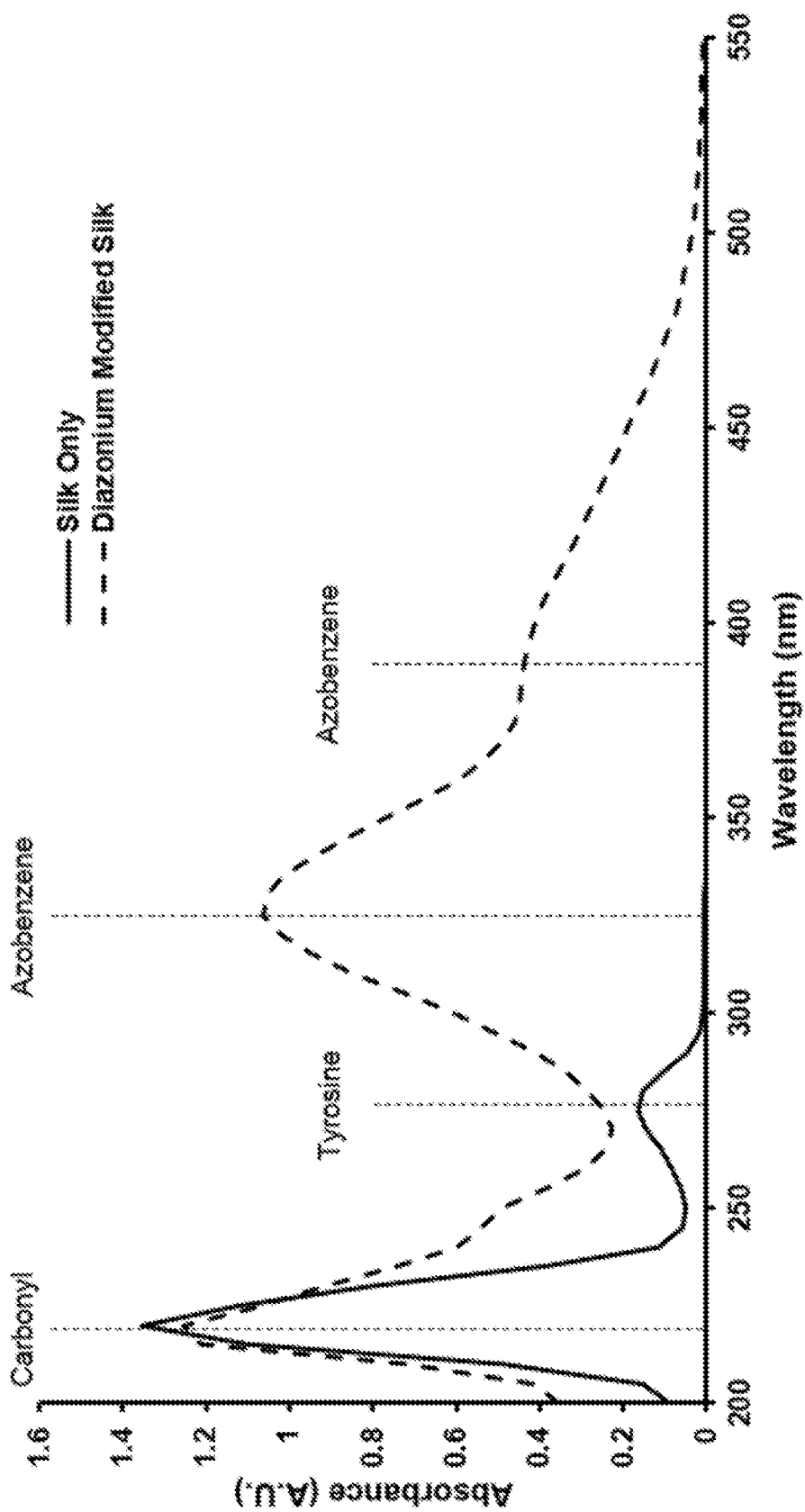
FIG. 14 shows spectrophotometric analysis of silk only and diazonium modified silk (normalized to the carbonyl peak) in water at pH 7. Molar equivalents of diazonium modified tyrosine residues were calculated based on azobenzene absorbance at 325 nm.

Modification by diazonium coupling was confirmed by spectrophotometric analysis (FIG. 14). See for example Murphy, A. R., St John, P., & Kaplan, D. L., Modification of silk fibroin using diazonium coupling chemistry and the effects on hMSC proliferation and differentiation, 29 Biomaterials 19, 2829-38 (2008). Modification was detected by observing a decrease in the tyrosine absorption peak at 280 nm compared to the silk only control, as well as an increase in the azobenzene absorption with peaks at 325 and 390 nm in the modified silk. The theoretical yield of modified tyrosine residues was calculated as 58.6% based on the available tyrosine residues per silk protein and the added diazonium salt concentration. Actual tyrosine modification per molecule of silk protein was estimated using Beer's Law. See for example Murphy, A. R., St John, P., & Kaplan, D. L., Modification of silk fibroin using diazonium coupling chemistry and the effects on hMSC proliferation and differentiation, 29 Biomaterials 19, 2829-38 (2008); see also Pielak, G. J., Urdea, M. S., Igi, K., & Legg, J. I., Azo protein analogues: synthesis and characterization of arsanilazo and sulfanilazo derivatives of tyrosine and histidine, 23 Biochemistry, 589-596 (1984). Modified tyrosine concentration was calculated from the absorbance at 325 nm using an extinction coefficient of 22,000 $M^{-1}$ $cm^{-1}$. The percentage was estimated by comparing this value to the molarity of silk protein. The estimated yield of azo-modified tyrosine was 57%. For simplicity, the nomenclature for these sponges rounded up to 60%. The modified diazonium-silk stock was diluted with native silk solution to achieve solutions with lower ratios of modified tyrosine.

Compressive Mechanics and Recovery of Modified Silk Sponges

Glycerol Only Modified Sponges

Figure 15:
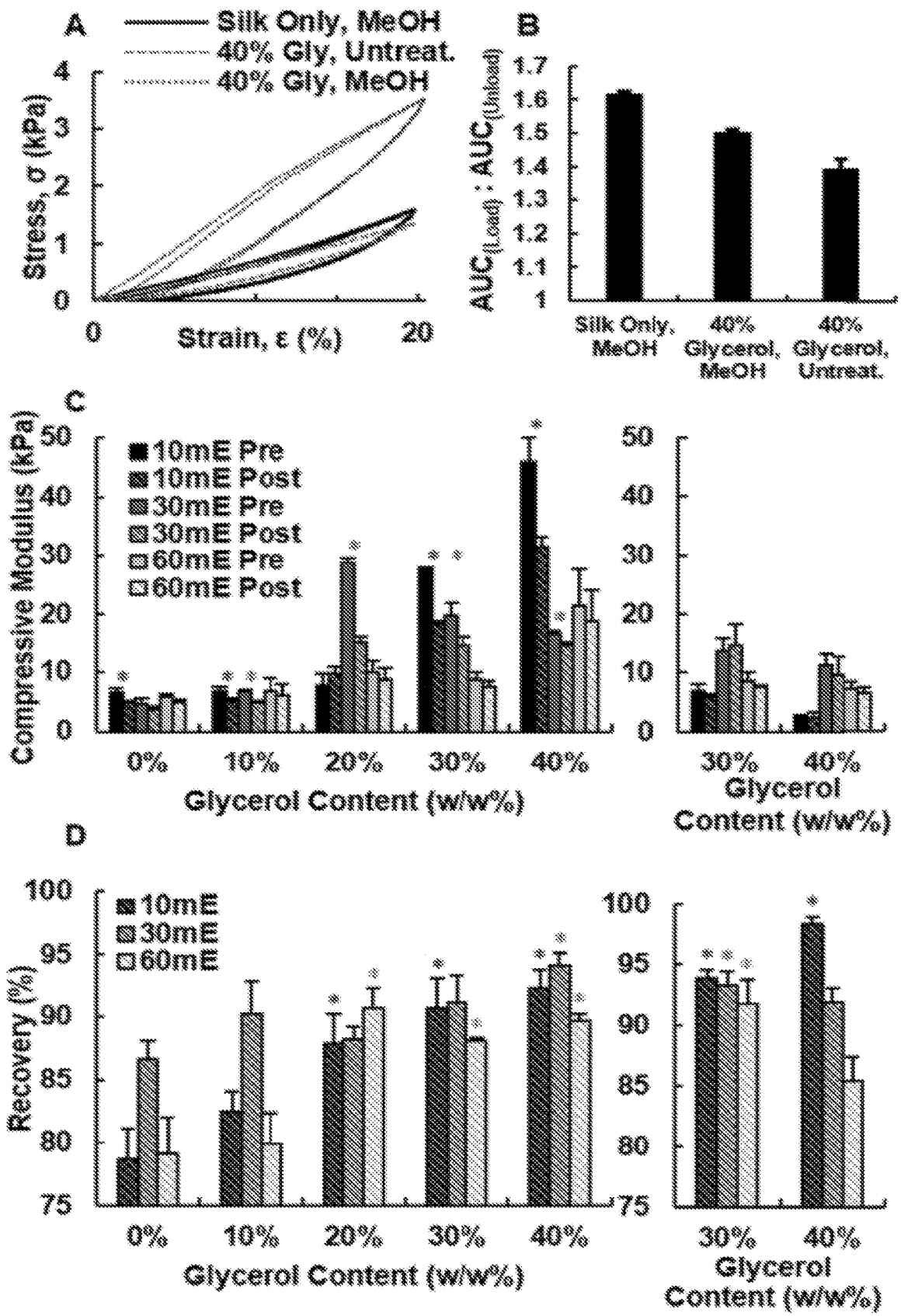
FIG. 15 shows mechanical compression analysis for silk-glycerol sponges.

Representative stress-strain profiles of 10 minute extracted silk sponges modified with either glycerol (40% by mass), methanol post-treatment or both are shown in FIG. 15. In general, the combination of high glycerol content (20% w/w or greater) and methanol post-treatment increased the stiffness of the silk sponges compared to silk alone (methanol treated) or untreated silk-glycerol (no methanol treatment). Similarly, changes in hysteresis (reported as a ratio of the areas under the curve for the load vs. unload cycles) were observed, with methanol treated silk only sponges exhibiting greater hysteresis during compression compared to both untreated and methanol treated silk-glycerol sponges (FIG. 15B).

The compressive modulus of the sponges ranged from approximately 7.5 kPa to 45.9 kPa after hydration in PBS (FIG. 15C), a range which is suitable for reconstruction of a variety of soft tissues. See for example Discher, D. E., Mooney, D. J., & Zandstra, P. W., Growth factors, matrices, and forces combine and control stem cells, 324 Science 5935, 1673-1677 (2010). In sponges post-treated with methanol, increasing the glycerol content correlates to an increased compressive modulus. Without a methanol wash, only the silk sponges containing high glycerol content (30% w/w or greater) were considered for testing since low glycerol content was not sufficient to cause crosslinking and insolubility in the material. Silk-glycerol sponges without methanol post-treatment were significantly softer than their methanol treated counterparts.

Silk extraction time alone did not have an impact on sponge stiffness. At low glycerol content (0 and 10% w/w) there was no significant difference in sponge compressive modulus. In general, changes in glycerol content had the greatest impact on 10 and 30 minute extracted silk sponges. 10 mE silk sponges increased in modulus as glycerol content increased, with significant changes at 30 and 40% w/w compared to control sponges. 30 mE sponges had a biphasic response, with a peak compressive modulus at 20% w/w glycerol content. There was no significant difference in the modulus of 60 mE sponges compared to silk only controls below 30% w/w glycerol. Without methanol treatment, 10 mE and 60 mE sponges were not significantly stiffer than their silk only controls.

Figure 16:
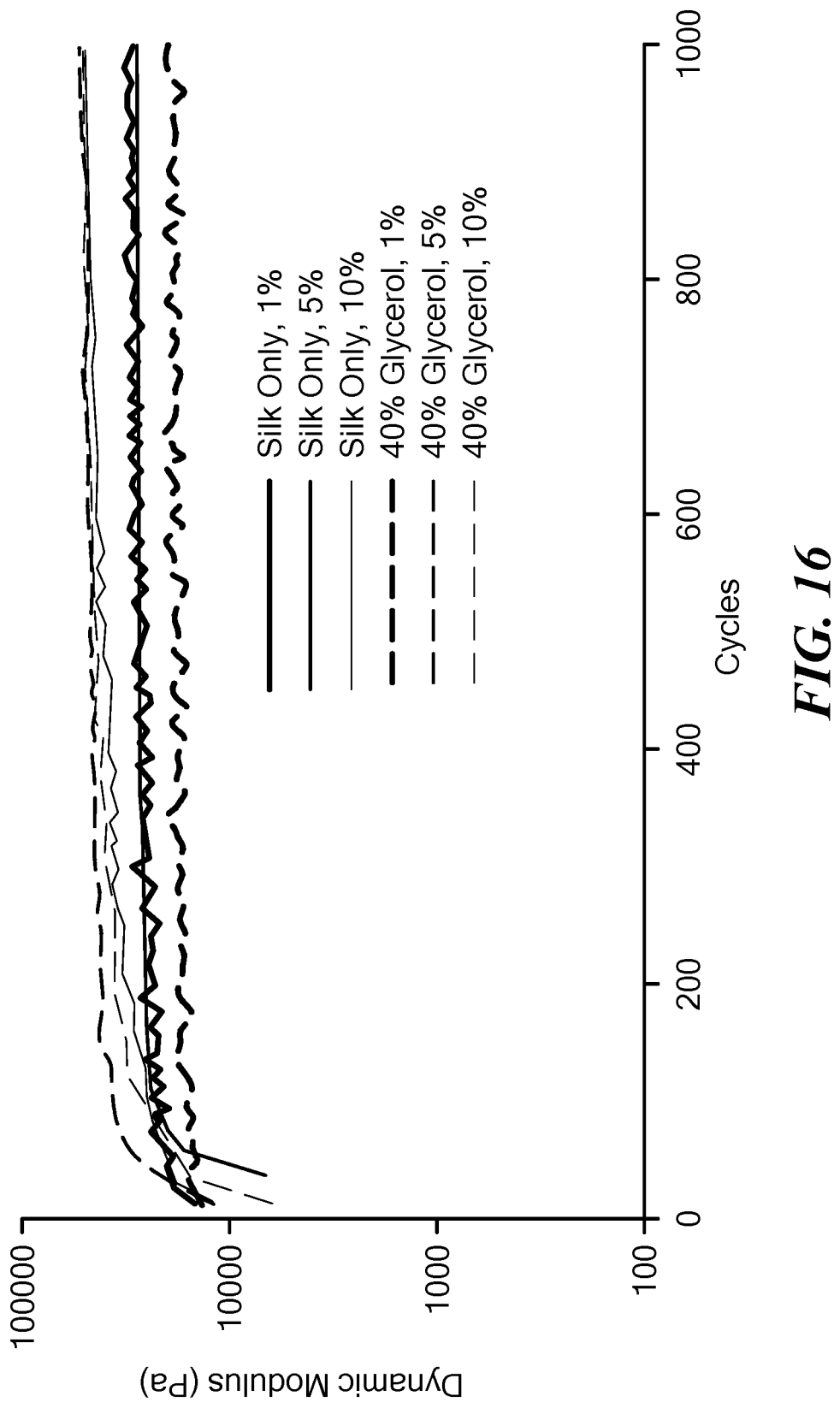
FIG. 16 shows fatigue testing of silk only and silk-40% w/w glycerol sponges over 1000 cycles. Frequency was kept constant at 0.5 Hz, while amplitude was varied from 1-10% strain. All sponges exhibited low fatigue and minimal change in dynamic modulus over 1000 cycles.

Shape fidelity, observed by comparing the compressive modulus before ("pre") and after ("post") high compression, as well as measuring the change in height after 80% strain, was impacted by both protein molecular weight and glycerol content (FIGS. 15C and 15D). In methanol post-treated samples, 10 minute extracted silk showed the largest difference in modulus after high compression, while there was no significant difference in the modulus of 60 mE sponges (Table 4). Silk-glycerol sponges (30% and 40% w/w) without methanol post-treatment had no significant difference in modulus pre- and post-80% axial strain regardless of extraction time. Shape recovery generally improved with an increase in glycerol concentration. 10 mE sponges with 40% w/w glycerol and no methanol treatment exhibited the greatest recovery (98.3% of initial height, vs. 78.6% recovery in 10 mE control sponges). In 10 mE sponges, both control sponges and sponges containing 40% w/w glycerol showed similar fatigue resistance, with minimal increase in compressive moduli over 1000 cycles (FIG. 16).

TABLE 4

Compressive moduli for silk sponge formula

| | Pre (in kPa) | | | Post (in kPa) | | |
|---|---|---|---|---|---|---|
| | Average | STD | | Average | STD | |
| 10mE 0% Glycerol | 6.7 | 0.6 | | 5.0 | 0.2 | |
| 10mE 10% Glycerol | 7.1 | 0.6 | | 5.4 | 0.4 | |
| 10mE 20% Glycerol | 8.0 | 1.9 | | 9.9 | 1.2 | ** |
| 10mE 30% Glycerol | 27.6 | 0.2 | *** | 18.3 | 0.4 | *** |
| 10mE 40% Glycerol | 46.0 | 4.1 | *** | 31.4 | 1.6 | *** |
| 10mE 30% Glycerol, No MeOH | 6.9 | 1.4 | | 5.9 | 0.6 | |
| 10mE 40% Glycerol, No MeOH | 3.0 | 0.0 | | 2.5 | 0.9 | |
| 30mE 0% Glycerol | 4.9 | 0.8 | | 3.9 | 0.4 | |
| 30mE 10% Glycerol | 7.0 | 0.3 | | 4.9 | 0.2 | |
| 30mE 20% Glycerol | 28.7 | 0.9 | *** | 15.0 | 1.0 | *** |
| 30mE 30% Glycerol | 19.8 | 2.1 | *** | 14.5 | 1.6 | *** |
| 30mE 40% Glycerol | 16.6 | 0.4 | *** | 14.5 | 0.5 | *** |
| 30mE 30% Glycerol, No MeOH | 13.7 | 2.1 | ** | 14.7 | 3.7 | *** |
| 30mE 40% Glycerol, No MeOH | 11.3 | 2.0 | * | 9.7 | 3.1 | |
| 60mE 0% Glycerol | 5.9 | 0.5 | | 5.1 | 0.5 | |
| 60mE 10% Glycerol | 7.0 | 2.1 | | 6.1 | 1.9 | |
| 60mE 20% Glycerol | 9.9 | 1.9 | | 8.8 | 2.0 | |
| 60mE 30% Glycerol | 8.8 | 1.4 | | 7.6 | 0.9 | |
| 60mE 40% Glycerol | 21.4 | 6.3 | ** | 18.7 | 5.3 | ** |
| 60mE 30% Glycerol, No MeOH | 8.5 | 1.4 | | 7.6 | 0.2 | |
| 60mE 40% Glycerol, No MeOH | 7.2 | 1.3 | | 6.5 | 0.9 | |
| 10mE, 10% SAA | 12.9 | 0.7 | *** | 8.9 | 0.4 | *** |
| 10mE, 30% SAA | 11.0 | 0.8 | ** | 8.4 | 0.3 | ** |
| 10mE, 60% SAA | 5.8 | 0.1 | | 5.2 | 0.3 | |
| 10mE, 10% SAA 30% Glycerol | 9.0 | 1.7 | | 2.7 | 1.1 | * |
| 10mE, 30% SAA 30% Glycerol | 9.2 | 0.0 | | 2.9 | 0.5 | |

Figure 17:
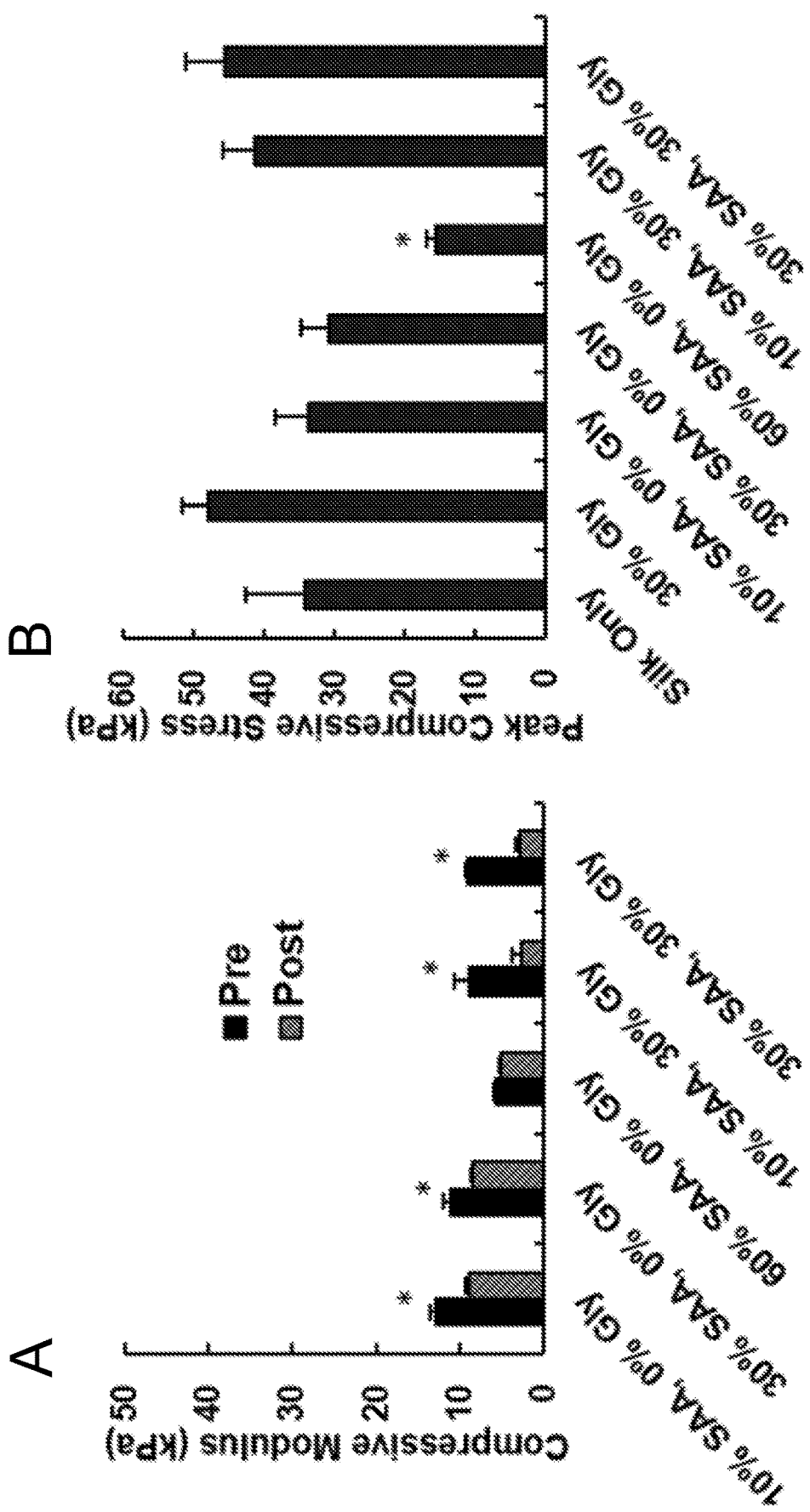
FIG. 17 shows mechanical compression analysis for diazonium modified silk sponges.

\* = p < 0.05;
\*\* = p < 0.01;
\*\*\* = p < 0.001, compared to the 0% glycerol sponges within each group Diazonium Modified Sponges 10% diazonium modified silk sponges (10 minute extraction) with methanol post-treatment were stiffer compared to unmodified silk only sponges (12.9±0.7 kPa vs. 6.7±0.6 kPa; FIG. 17). As the calculated content of diazonium modified tyrosine residues increased to 30% and 60%, compressive modulus was reduced to 11.0±0.8 and 5.8±0.1 kPa, respectively. Addition of 30% w/w glycerol to 10% and 30% diazonium modified sponges (without methanol post-treatment) reduced the compressive modulus to 9.0±1.7 and 9.2±0.02 kPa, respectively. Glycerol sponges with 60% diazonium modification were not able to maintain their shape, resulting in a gel-like consistency. The compressive modulus was unable to be measured.

High axial strain (80% max height) significantly reduced the compressive modulus of post-compressed material for all diazonium modified sponges, with and without glycerol, except for the 60% SAA modified sponges without glycerol. 10% and 30% diazonium modified sponges with glycerol experienced the largest change in compressive modulus before and after high compression, indicating low resistance to plastic deformation. The peak compressive stress at 80% axial strain was also recorded. This value was used as a predictor for injection forces. Greater peak stresses at 80% compression would likely result in higher injection forces. In general, the addition of 30% w/w glycerol increases the average compressive stress of all sponges compared to their 0% glycerol counterparts. As diazonium modification content increases, the peak stress decreases, following the trends observed in compressive modulus.

Swelling Ratios

Figure 18:
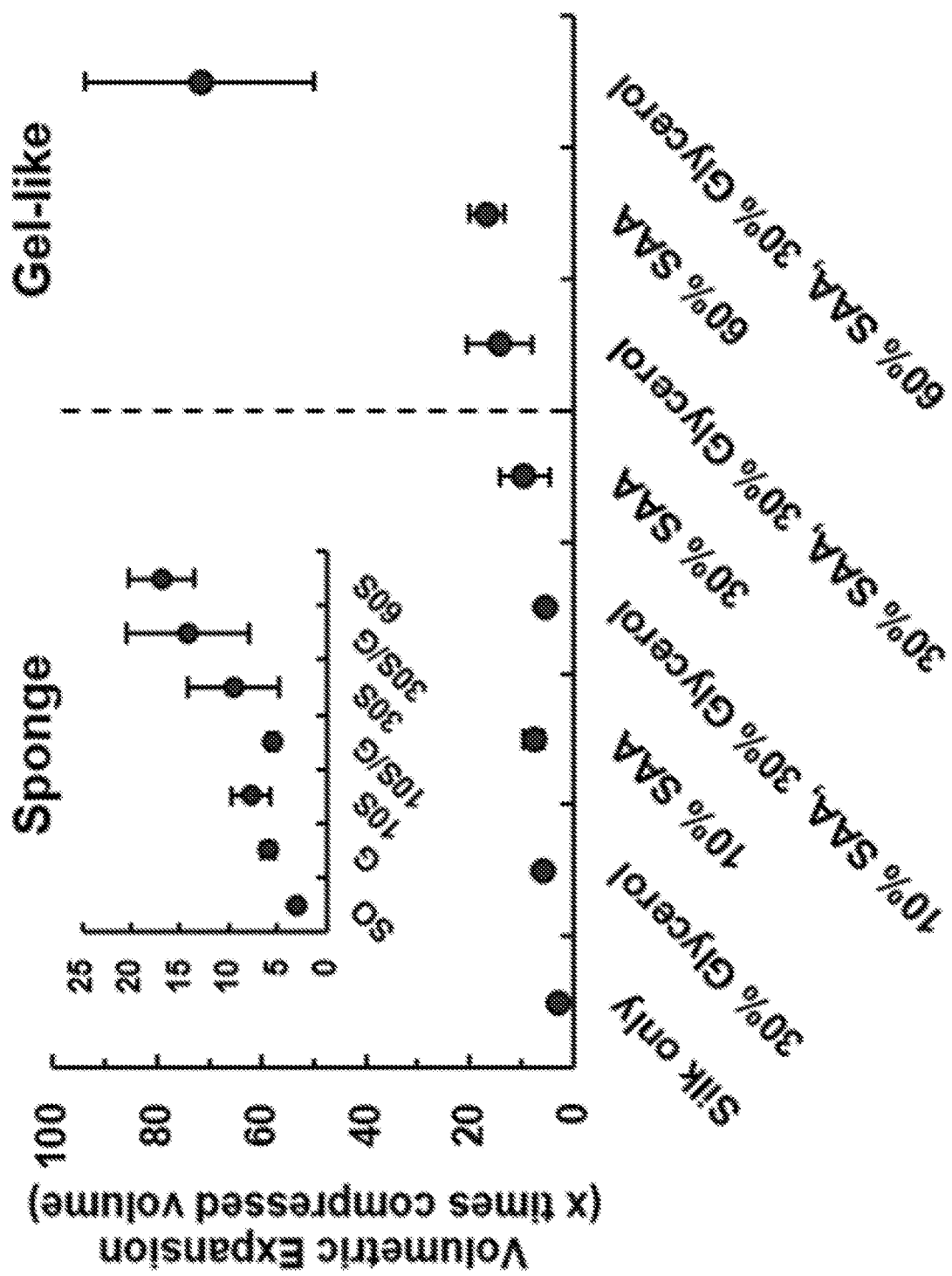
FIG. 18 shows volumetric expansion of silk sponges in 1×PBS after 90% axial compression. The combination of tyrosine modification with sulfanilic acid (% SAA) with glycerol additives improves volumetric swelling of compressed materials compared to silk only controls. At high diazonium modification, the swollen sponges lost their rigidity, assuming an amorphous shape and gel-like consistency.
Figure 19:
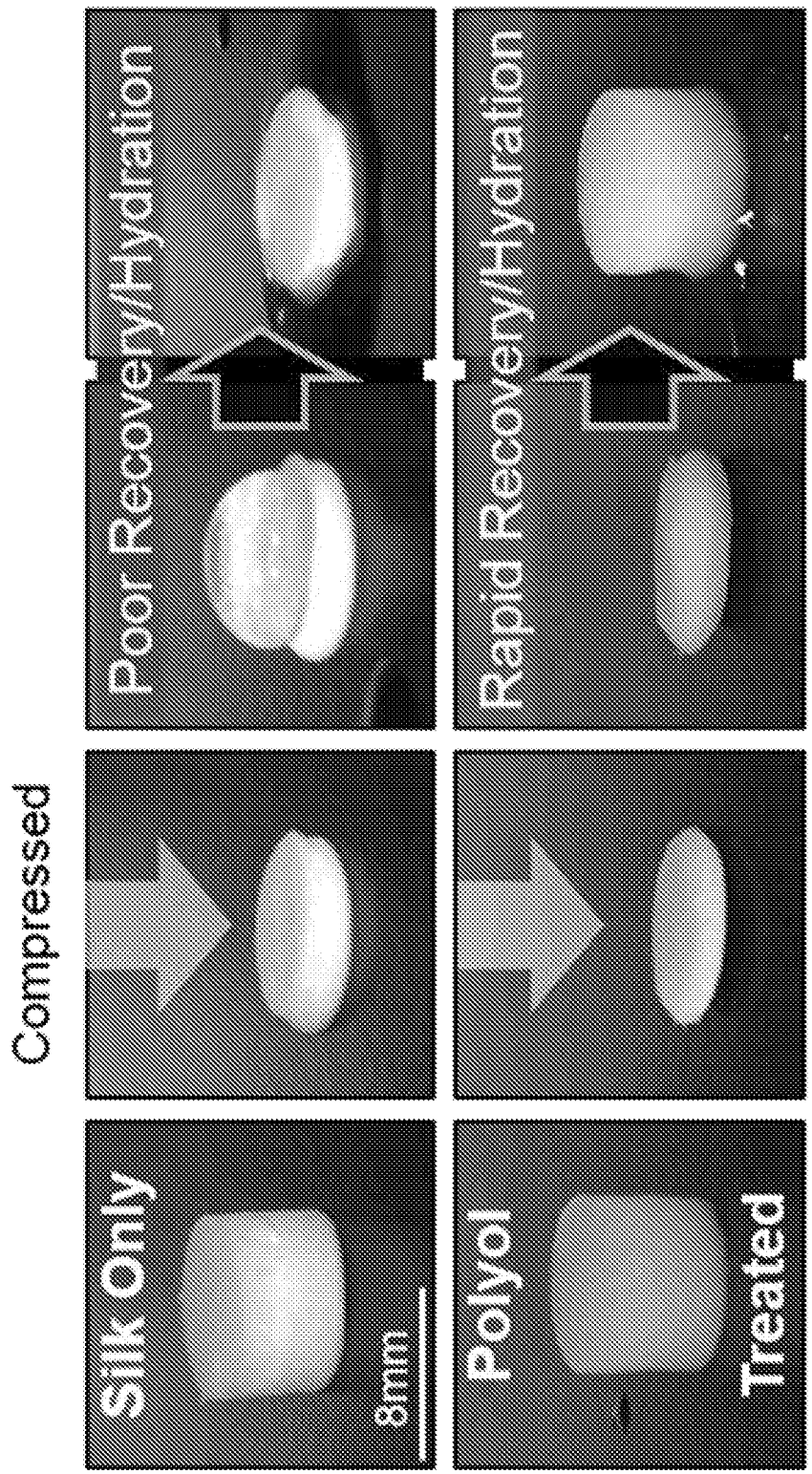
FIG. 19 shows hydration and recovery of compressed silk sponges. Unmodified silk sponges generally exhibit plastic deformation from mechanical compression. Furthermore, hydration is slow in unmodified sponges and does not yield rapid volumetric recovery. Alternatively, glycerol modified sponges exhibit rapid uptake of aqueous media and volume expansion, as well as near complete recovery of the original geometry.

Swelling was quantified by measuring the volume of sponges before and after high axial compression. Sponges derived from 10 mE silk fibroin were subjected to very high compression (95% axial strain, or 5% of their original height) and dried by wicking away residual and unbound water. Swelling was calculated by measuring the axial and radial dimensions of samples before and after submersion in 1×PBS, thereby measuring media absorption (FIGS. 18, 19). This test complements the recovery tests (which focused solely on sample height) because it takes into account the total volume, an important parameter for injectability. After compression, the silk only (control) sponges swelled to 2.9× their compressed volume, exhibiting high plastic deformation and incomplete recovery to their original volume. Untreated silk sponges with 30% w/w glycerol swelled to 5.9× of their compressed volume. In general, diazonium modification increased the volumetric expansion of silk sponges after compression. Diazonium sponges with 10%, 30% and 60% tyrosine modification showed 7.7×, 9.5×, 16.9× volumetric expansion from a compressed state, respectively. By adding 30% w/w glycerol, the volumetric expansion of these diazonium modified sponges changed to 5.4×, 14.2× and 71.4×, respectively. There was no significant difference in the volumetric expansion of 10% and 30% diazonium modified sponges with vs. without glycerol.

Secondary Structure Analysis
Glycerol Only Modified Sponges

Figure 20:
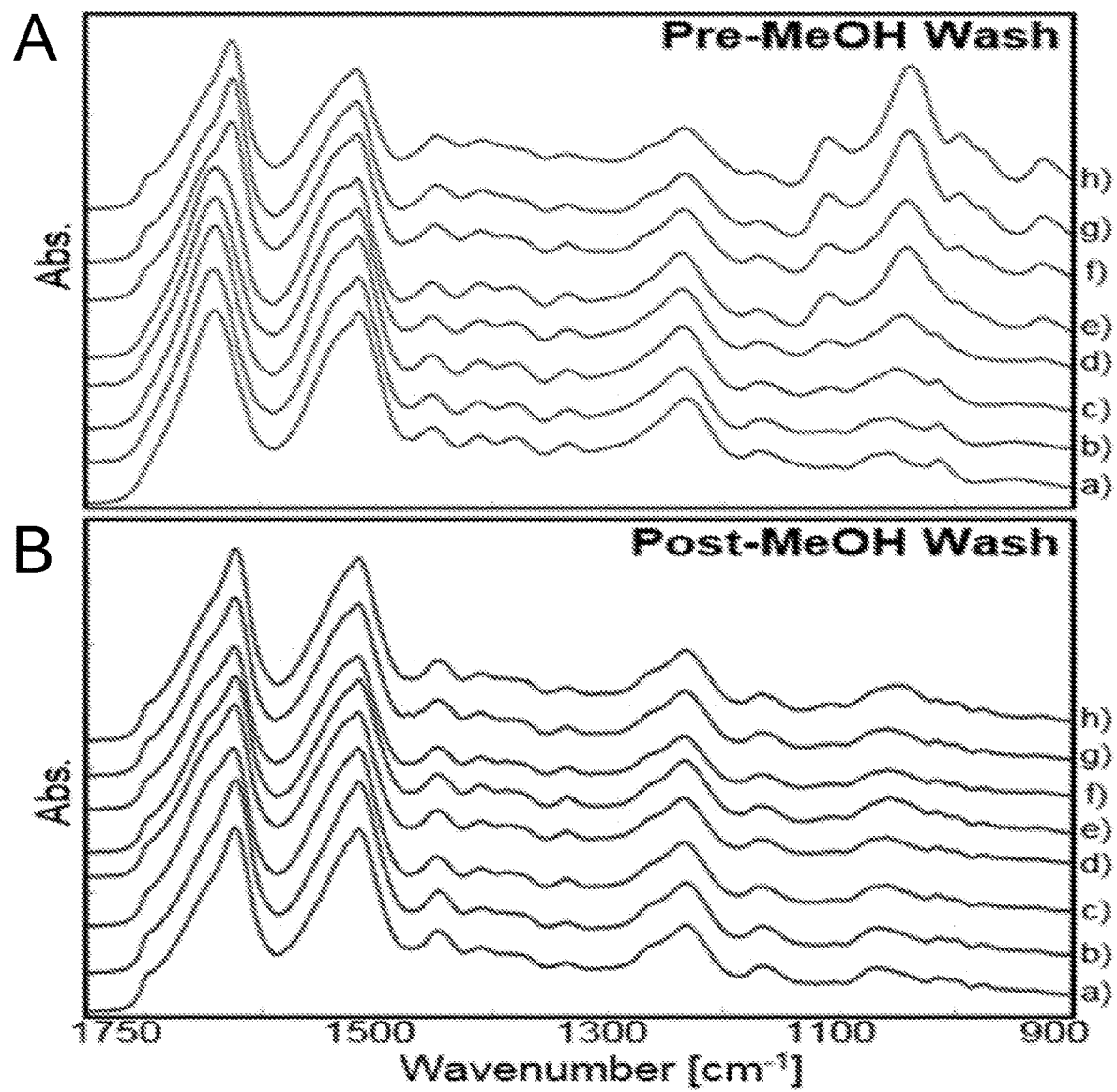
FIG. 20 shows secondary structure of silk-glycerol sponges by FT-IR analysis.
Figure 20:
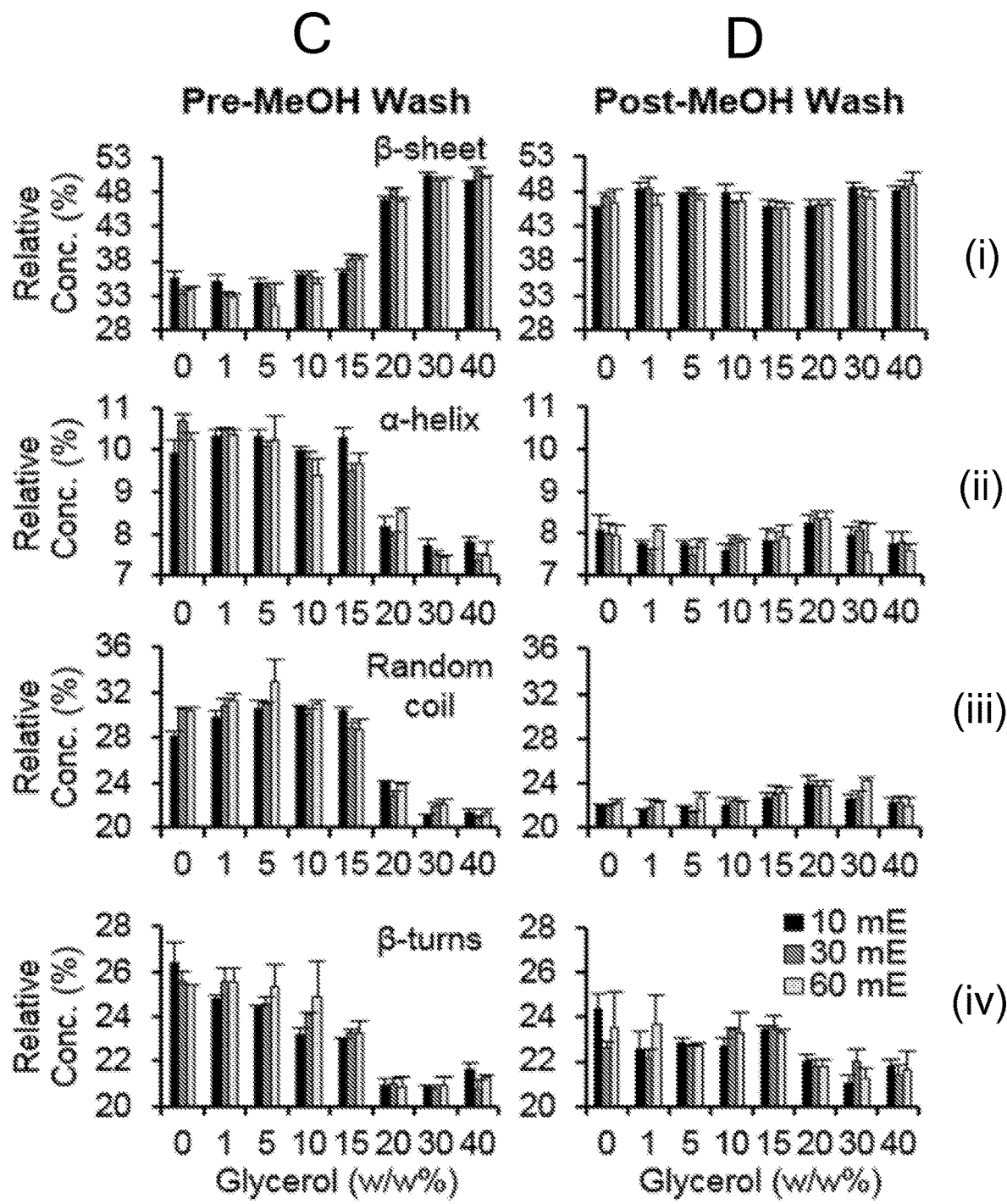

Secondary structure was measured to correlate changes in protein structure with differences in bulk sponge mechanical properties (FIG. 20, Table 5). FT-IR spectra were recorded on materials with and without glycerol, before and after methanol post-treatment to detect differences in crystallinity as a result of each modifier. Extraction time did not play a significant role in protein secondary structure. In silk-glycerol sponges before methanol treatment, an increase in β-sheet structure begins to occur at 15% w/w glycerol and higher. At 20% w/w glycerol and below, it was observed that sponges were either partially or fully soluble in aqueous media, and therefore not used for mechanical analysis without a methanol post-treatment step. The increased β-sheet structure in silk materials with high glycerol concentration has been reported in several other studies. See for example Jose, R. R., Brown, J. E., Polido, K. E., Omenetto, F. G., & Kaplan, D. L., Polyol-Silk Bioink Formulations as Two-Part Room-Temperature Curable Materials for 3D Printing, 1 ACS Biomaterials Science & Engineering 9, 780-788 (2015); see also Lu, Q., Hu, X., Wang, X., Kluge, J., Lu, S., Cebe, P., & Kaplan, D. L., Water-insoluble silk films with silk I structure, 6 Acta Biomaterialia 4, 1380-7 (2010); Pei, Y., Liu, X., Liu, S., Lu, Q., Liu, J., Kaplan, D. L., & Zhu, H., Mild process to design silk scaffolds with reduced β-sheet structure and various topographies at nanometer scale, 13 Acta Biomaterialia, 168-176 (2015). Alternatively, increasing glycerol concentration to 20% w/w and higher in pre-methanol treated sponges triggered a decrease in the β-turn, random coil and α-helix structures. After methanol treatment, all sponges containing 15% w/w glycerol or less exhibited a significant increase in β-sheet structure and significant decreases in random coil and α-helical structures. Sponges containing 20% w/w glycerol trended towards a slight decrease in β-sheet structure after methanol treatment and slight increases in the other three structural elements. Additionally, the peaks from 800-1150 cm$^{-1}$ have previously been associated with absorption bands from glycerol. See for example Ramos, O. L., Reinas, I., Silva, S. I., Fernandes, J. C., Cerqueira, M. a., Pereira, R. N., Malcata, F. X., Effect of whey protein purity and glycerol content upon physical properties of edible films manufactured therefrom, 30 Food Hydrocolloids 1, 110-122 (2013). Reduced peak intensity in this region suggests that glycerol has been removed from the material after methanol washing.

TABLE 5

Quantification of secondary structure in silk sponges.

| | | β-Sheet | | | | | α-Helix | | | | |
|---|---|---|---|---|---|---|---|---|---|---|---|
| | Glycerol | Pre | | Post | | | Pre | | Post | | |
| | (% w/w) | Ave. | STD | Ave. | STD | Sig. | Ave. | STD | Ave. | STD | Sig. |
| 10mE | 0% | 35.6 | 1.0 | 45.6 | 0.2 | *** | 9.9 | 0.3 | 8.1 | 0.4 | ** |
| | 1% | 35.1 | 0.9 | 48.2 | 1.1 | ** | 10.3 | 0.2 | 7.8 | 0.1 | *** |
| | 5% | 34.8 | 0.7 | 47.8 | 0.2 | *** | 10.3 | 0.1 | 7.8 | 0.1 | *** |
| | 10% | 36.1 | 0.4 | 47.8 | 1.2 | *** | 10.0 | 0.1 | 7.6 | 0.1 | *** |
| | 15% | 36.3 | 0.5 | 45.9 | 0.8 | *** | 10.3 | 0.3 | 7.8 | 0.3 | *** |
| | 20% | 46.9 | 0.5 | 45.8 | 1.0 | | 8.2 | 0.2 | 8.2 | 0.2 | |
| | 30% | 50.5 | 0.3 | 48.4 | 0.9 | * | 7.7 | 0.2 | 7.9 | 0.2 | |
| | 40% | 48.3 | 0.4 | 48.1 | 0.6 | | 7.8 | 0.1 | 7.7 | 0.3 | |
| 30mE | 0% | 33.3 | 0.6 | 47.4 | 0.5 | *** | 10.7 | 0.1 | 8.0 | 0.2 | *** |
| | 1% | 33.1 | 0.5 | 48.6 | 1.3 | *** | 10.5 | 0.1 | 7.5 | 0.1 | *** |
| | 5% | 34.4 | 0.4 | 48.5 | 0.1 | *** | 10.1 | 0.1 | 7.5 | 0.2 | *** |
| | 10% | 36.0 | 0.5 | 46.2 | 0.3 | *** | 9.8 | 0.1 | 7.9 | 0.1 | *** |
| | 15% | 38.3 | 0.6 | 45.6 | 1.1 | ** | 9.5 | 0.2 | 7.8 | 0.3 | ** |
| | 20% | 48.3 | 0.2 | 46.0 | 0.8 | * | 8.0 | 0.1 | 8.4 | 0.2 | * |
| | 30% | 49.7 | 0.3 | 47.2 | 1.3 | * | 7.5 | 0.1 | 8.1 | 0.2 | * |
| | 40% | 51.0 | 0.5 | 48.5 | 0.9 | * | 7.4 | 0.2 | 7.8 | 0.2 | |
| 60mE | 0% | 34.0 | 0.4 | 46.2 | 2.1 | ** | 10.2 | 0.2 | 7.9 | 0.3 | *** |
| | 1% | 32.8 | 0.5 | 46.0 | 1.6 | *** | 10.4 | 0.1 | 8.1 | 0.1 | *** |
| | 5% | 31.5 | 3.4 | 46.8 | 0.7 | ** | 10.2 | 0.6 | 7.8 | 0.1 | ** |
| | 10% | 34.8 | 0.9 | 46.7 | 1.1 | *** | 9.4 | 0.4 | 7.8 | 0.1 | ** |
| | 15% | 38.2 | 0.6 | 45.6 | 0.8 | *** | 9.7 | 0.2 | 7.9 | 0.3 | ** |
| | 20% | 46.6 | 0.6 | 46.0 | 0.8 | | 8.5 | 0.1 | 8.4 | 0.2 | |
| | 30% | 49.6 | 0.6 | 47.0 | 1.0 | * | 7.4 | 0.0 | 7.6 | 0.7 | |
| | 40% | 50.0 | 0.3 | 48.9 | 1.7 | | 7.5 | 0.3 | 7.6 | 0.2 | |

| | | Random Coil | | | | | β-Turn | | | | |
|---|---|---|---|---|---|---|---|---|---|---|---|
| | Glycerol | Pre | | Post | | | Pre | | Post | | |
| | (% w/w) | Ave. | STD | Ave. | STD | Sig. | Ave. | STD | Ave. | STD | Sig. |
| 10mE | 0% | 28.1 | 0.5 | 21.9 | 0.2 | *** | 26.4 | 0.9 | 24.4 | 0.7 | |
| | 1% | 29.8 | 0.6 | 21.5 | 0.2 | *** | 24.8 | 0.1 | 22.5 | 0.8 | |
| | 5% | 30.5 | 0.9 | 21.8 | 0.2 | *** | 24.4 | 0.0 | 22.9 | 0.2 | *** |
| | 10% | 30.7 | 0.1 | 22.0 | 0.8 | *** | 23.2 | 0.3 | 22.7 | 0.4 | |
| | 15% | 30.4 | 0.3 | 22.8 | 0.5 | *** | 23.0 | 0.0 | 23.5 | 0.1 | ** |
| | 20% | 24.0 | 0.2 | 24.0 | 0.7 | | 20.9 | 0.3 | 22.0 | 0.2 | * |
| | 30% | 21.0 | 0.1 | 22.6 | 0.5 | ** | 20.8 | 0.1 | 21.0 | 0.3 | |
| | 40% | 21.3 | 0.2 | 22.3 | 0.3 | * | 21.6 | 0.3 | 21.8 | 0.3 | |
| 30mE | 0% | 30.5 | 0.2 | 22.0 | 0.1 | *** | 25.5 | 0.4 | 22.6 | 0.3 | ** |
| | 1% | 30.9 | 0.8 | 21.7 | 0.9 | *** | 25.5 | 0.8 | 22.2 | 0.4 | ** |
| | 5% | 31.0 | 0.2 | 21.4 | 0.2 | *** | 24.6 | 0.3 | 22.7 | 0.1 | *** |
| | 10% | 30.1 | 0.4 | 22.5 | 0.2 | *** | 24.1 | 0.1 | 23.5 | 0.1 | ** |
| | 15% | 28.9 | 0.5 | 23.0 | 0.8 | *** | 23.3 | 0.2 | 23.6 | 0.4 | |
| | 20% | 22.7 | 0.5 | 23.9 | 0.4 | | 21.0 | 0.2 | 21.8 | 0.3 | * |
| | 30% | 21.9 | 0.2 | 22.8 | 0.6 | | 20.8 | 0.1 | 22.0 | 0.5 | * |
| | 40% | 20.9 | 0.2 | 22.3 | 0.6 | * | 20.7 | 0.5 | 21.4 | 0.5 | |
| 60mE | 0% | 30.5 | 0.2 | 22.3 | 0.3 | *** | 25.4 | 0.0 | 23.5 | 1.6 | |
| | 1% | 31.3 | 0.5 | 22.2 | 0.2 | *** | 25.6 | 0.5 | 23.7 | 1.3 | |
| | 5% | 32.9 | 2.0 | 22.7 | 0.4 | ** | 25.3 | 1.0 | 22.7 | 0.2 | * |
| | 10% | 31.0 | 0.3 | 22.3 | 0.1 | *** | 24.9 | 1.8 | 23.3 | 1.0 | |
| | 15% | 28.8 | 0.6 | 23.2 | 0.5 | ** | 23.3 | 0.5 | 23.3 | 0.2 | |
| | 20% | 23.9 | 0.1 | 23.9 | 0.4 | | 20.9 | 0.4 | 21.8 | 0.3 | * |
| | 30% | 22.1 | 0.5 | 24.2 | 0.3 | ** | 20.9 | 0.4 | 21.2 | 0.5 | |
| | 40% | 21.2 | 0.4 | 21.9 | 0.8 | | 21.3 | 0.1 | 21.6 | 0.9 | |

Figure 21:
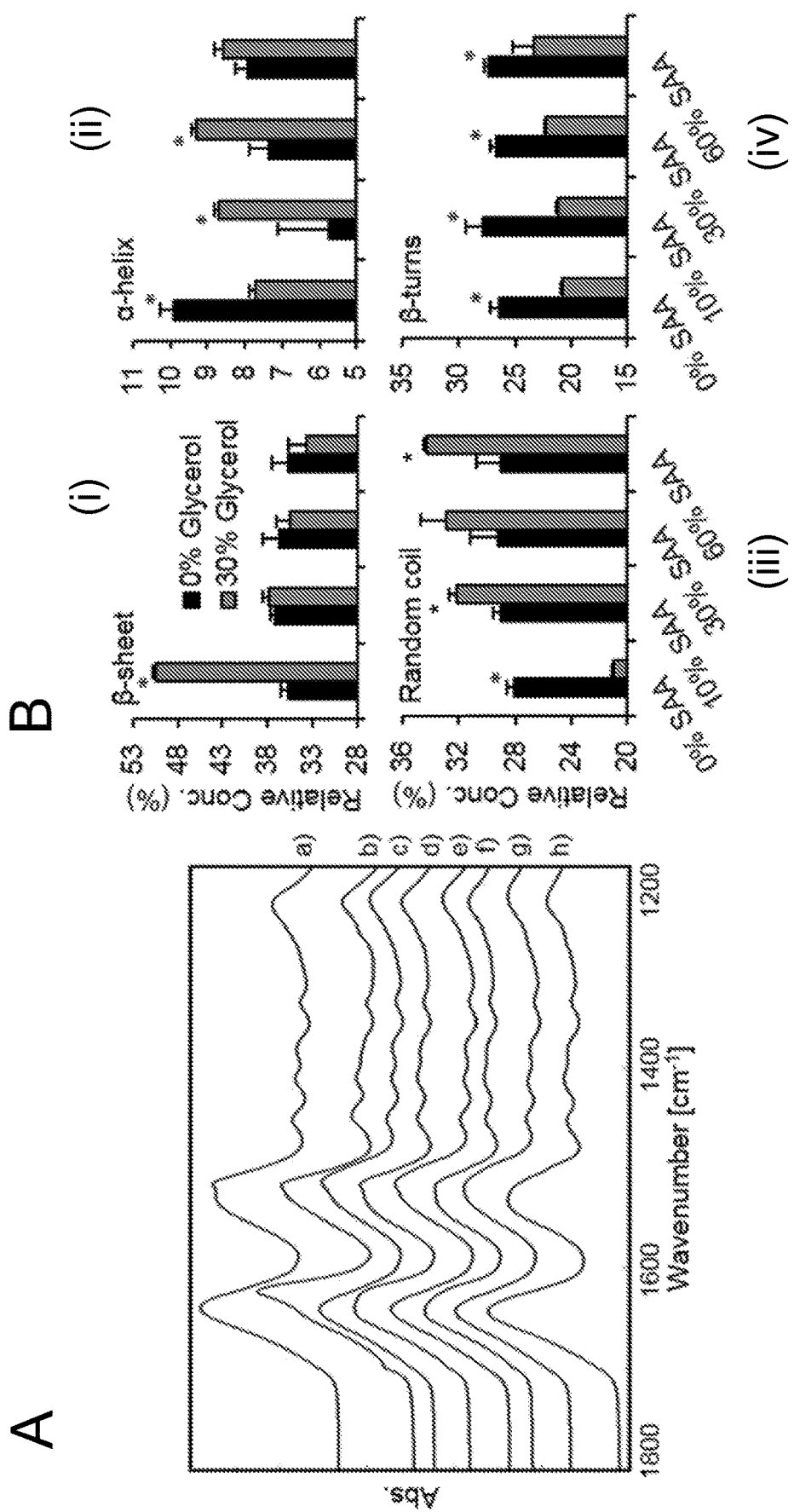
FIG. 21 shows secondary structure of diazonium modified silk sponges by FT-IR analysis. Modification of tyrosine residues with hydrophilic chemistries resulted in a significant reduction of β-sheet structure.

Results reported as the relative percentage (%) of each secondary structure vs. all the amide I (C═O vibrations from protein hydrogen bonding). Measurements are reported for before ("pre") and after ("post") methanol treatment.
* = $p < 0.05$;
** = $p < 0.01$;
*** = $p < 0.001$, comparing "pre" and "post" for each formulation Diazonium Modified Sponges The secondary structural elements of diazonium modified silk sponges were compared between 10 mE 30% w/w glycerol sponge and 10 mE untreated 0% w/w glycerol sponge groups (FIG. 21). As seen previously, the addition of 30% w/w glycerol to an unmodified silk sponge results in a significant increase in β-sheet content in comparison to control silk only sponges (50.5%±0.3% vs. 35.6±1.0%). However, with the addition of diazonium modification on the tyrosine residues, we observed a large decrease in β-sheet structure within the range of modified tyrosine concentration tested. In general, β-sheet content decreased in silk-glycerol sponges as diazonium content increased. Additionally, there were significant increases in α-helical and random coil structures and significant decreases in β-turn structure in diazonium modified silk-glycerol sponges vs. silk only sponges.

Pore Morphology and Porosity

To facilitate proper tissue integration, porous materials must contain interconnected, open cell structures large enough to accommodate cellular infiltration. To capture the pore morphology in a hydrated state, sponges were swollen in deionized water and freeze-dried again before SEM analysis. FIG. 22A shows the macroscopic appearance of unmodified vs. diazonium modified silk sponges, while FIG. 22B shows the microscopic pore morphology of cross-sectioned sponges (10 mE silk, with and without glycerol) with different concentrations of diazonium modification. Regardless of the presence of glycerol, we observed that increasing the concentration of tyrosine modification produced pores with enlarged diameters. Furthermore, the addition of glycerol yielded pores with a more rounded morphology, while silk sponges without glycerol typically exhibited jagged or lamellar pores.

Mercury intrusion porosimetry was also used to characterize the pore volume and size distribution of modified silk sponges (Table 6). Extraction time impacted pore size distribution and morphology, with longer extraction times incurring greater polydispersity (FIG. 22C). The mean pore diameters were 11.3 μm, 13.1 μm, and 14.2 μm, with peak maxima located at 11.6 μm, 29.2 μm, and 34.5 μm for 10 mE, 30 mE and 60 mE, respectively. With the addition of 30% w/w glycerol, the pore size distribution functions narrowed for all extraction times, with pore diameters predominantly between 5-50 μm (FIG. 22D). The mean pore diameters were 13.5 μm, 15.5 μm, 20.8 μm, with peak maxima located at 33.2 & 11.0 μm (2 peaks), 16.7 μm, and 19.3 μm for 10 mE, 30 mE and 60 mE, respectively. By modifying silk with hydrophilic sulfanilic acid groups, we observed a large increase in the pore diameters (FIG. 22E). For 10%, 30% and 60% diazonium modification, the mean pore diameters were 51.9 μm, 55.3 μm, and 76.8 μm, respectively, while the addition of 30% w/w glycerol changed the mean diameters to 64.1 μm, 54.1 μm, and 91.2 μm, respectively. All samples were highly porous, with 30 mE, 30% w/w glycerol samples having the lowest porosity at 88.5% void space (volume of void space out of total material volume).

TABLE 6

Porosity characteristics of modified silk sponges

| Treatment | Porosity (%) | Mean Pore Dia. (μm) | Max Pore Dia. (μm) |
|---|---|---|---|
| 10mE, Unmod. | 95.5 | 11.3 | 295.5 |
| 30mE, Unmod. | 95.2 | 13.1 | 292.5 |
| 60mE, Unmod. | 94.5 | 14.2 | 291.8 |
| 10mE, 30% w/w Glycerol | 89.9 | 13.5 | 295.5 |
| 30mE, 30% w/w Glycerol | 88.5 | 15.5 | 292.5 |

TABLE 6-continued

Porosity characteristics of modified silk sponges

| Treatment | Porosity (%) | Mean Pore Dia. (μm) | Max Pore Dia. (μm) |
|---|---|---|---|
| 60mE, 30% w/w Glycerol | 91.1 | 20.8 | 291.8 |
| 10mE, 10% SAA | 97.2 | 51.9 | 334 |
| 10mE, 30% SAA | 96.8 | 55.3 | 289.9 |
| 10mE, 60% SAA | 97.1 | 76.8 | 289.9 |
| 10mE, 10% SAA, 30% w/w Glycerol | 96.5 | 64.1 | 305 |
| 10mE, 30% SAA, 30% w/w Glycerol | 96.8 | 54.1 | 272.3 |
| 10mE, 60% SAA, 30% w/w Glycerol | 96.5 | 91.2 | 289.5 |

In Vivo Degradation

Figure 23:
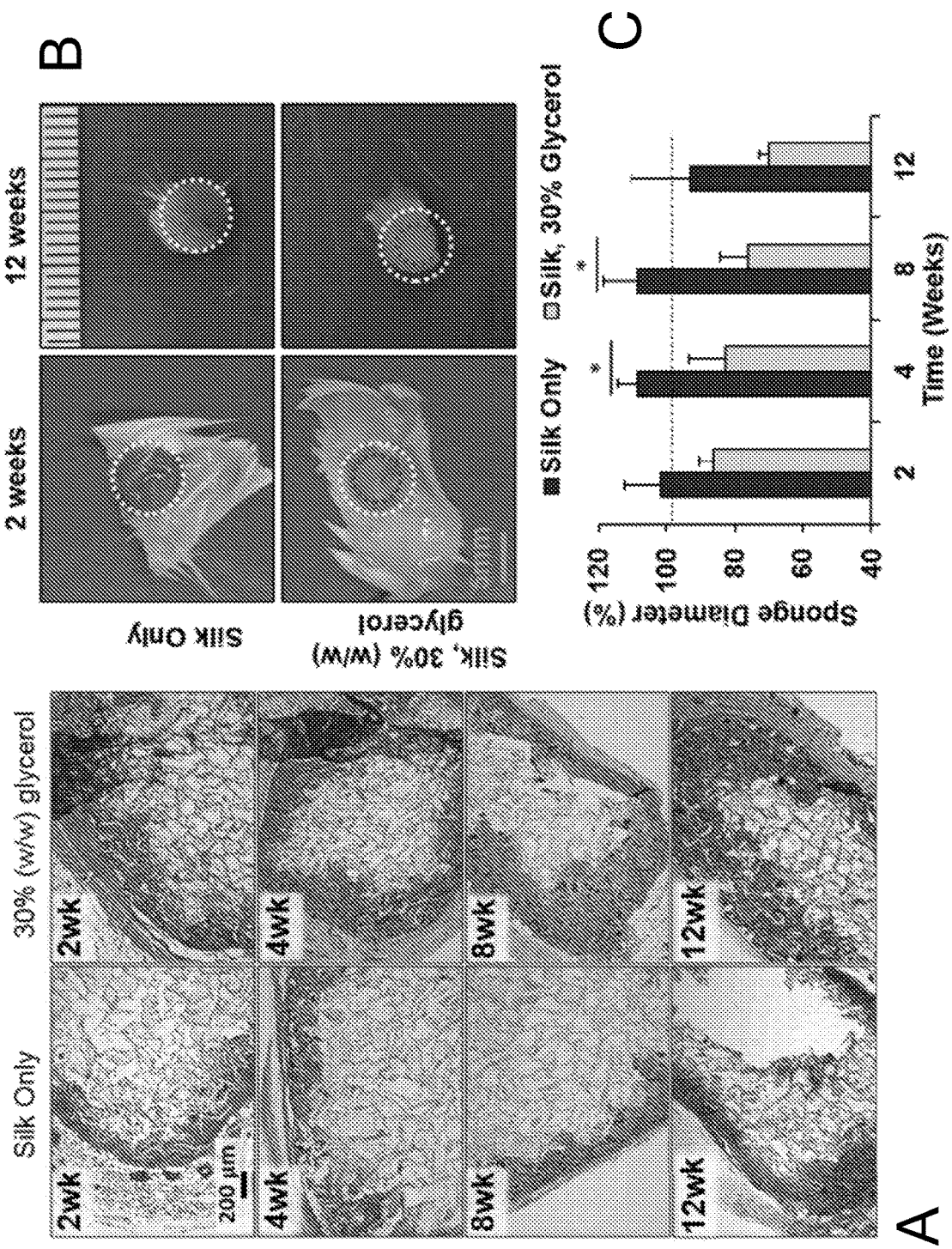
FIG. 23 shows in vivo subcutaneous implantation of silk-glycerol sponges in mouse models.

Silk only (control) and silk-glycerol sponges were subcutaneously implanted into mice to monitor inflammatory response and cellular infiltration into the bulk sponge structure. Sponges were sterilized via wet autoclave cycle and implanted after being fully-hydrated in 1×PBS. Histological analysis of recovered materials after 2, 4, 8 and 12 weeks shows that there is minimal immune response in both groups, but extensive cell infiltration and material degradation in silk-glycerol sponges compared to control groups (FIG. 23). By 12 weeks, H&E staining showed that cells were mostly relegated to the perimeter of the silk only control sponges. In contrast, cells were able to infiltrate deeper into the core of the silk-glycerol sponges. By measuring the diameter of the excised sponges, we observed initial swelling of the silk only control over 8 weeks, while silk-glycerol sponges had already begun to degrade by 2 weeks. By the end of the study only 69.9% of the initial silk-glycerol sponge volume remained, compared to 93.1% initial volume of the silk only controls.

Discussion

The goal of this study was to develop biodegradable sponges that exhibit high swelling and shape recovery after compression for use with injectable devices and soft tissue filler applications. As shown in previous work, see for example Bellas, E., Lo, T. J., Fournier, E. P., Brown, J. E., Abbott, R. D., Gil, E. S., Kaplan, D. L., Injectable Silk Foams for Soft Tissue Regeneration, 4 Advanced Healthcare Materials 3, 452-459 (2015); see also Bellas, E., Panilaitis, B. J. B., Glettig, D. L., Kirker-Head, C. A, Yoo, J. J., Marra, K. G., Kaplan, D. L., Sustained volume retention in vivo with adipocyte and lipoaspirate seeded silk scaffolds, 34 Biomaterials 12, 2960-8 (2013); Wang, Y., Rudym, D. D., Walsh, A., Abrahamsen, L., Kim, H. J., Kim, H. S., Kaplan, D. L., In vivo degradation of three-dimensional silk fibroin scaffolds, 29 Biomaterials, 3415-3428 (2008) porous silk scaffolds are mechanically robust, tunable and capable of long-term in vivo volume retention. Unfortunately, these silk scaffolds are also relatively brittle and tend to plastically deform under high stress. While ideal for large scale defects and soft tissue reconstruction requiring invasive surgical techniques, these 3-dimensional silk scaffolds would require substantial reformulation to achieve the mechanical elasticity required for minimally invasive deployment strategies and small volume defect remediation. Previous approaches to design porous silk materials with shape memory characteristics have focused on chemical modification with poly (N-isopropylacrylamide) (PNIPAAm). See for example Gil, E. S., & Hudson, S. M., Effect of Silk Fibroin Interpenetrating Networks on Swelling/Deswelling Kinetics and Rheological Properties of Poly(N-isopropylacrylamide) Hydrogels, 8 Biomacromolecules, 258-264 (2007); see also Gil, E. S., Park, S.-H., Tien, L. W., Trimmer, B., Hudson, S. M., & Kaplan, D. L., Mechanically robust, rapidly actuating, and biologically functionalized macroporous poly(N-isopropylacrylamide)/silk hybrid hydrogels, 26 Langmuir 19, 15614-24 (2010). These materials can swell and compress in response to changes in temperature. This is ideal for injectable applications where triggerable material compression is desired during injection and expansion after implantation; however, there are concerns regarding the safety of synthetic and potentially toxic additives such as PNIPAAm in biological systems, as well as the lack of biodegradability. In the present study, we sought to use non-toxic, biologically safe additives and chemical modifications to design materials that exhibited triggered expansion in response to hydration while also retaining full degradablity over time. These materials could theoretically be compressed and injected in an unsaturated state, then expand in hydrated media to their original volume and open-cell structure to accommodate tissue bulking, cell infiltration and remodeling of the surrounding extracellular matrix.

These new sponge designs predominantly focus on merging two separate strategies: blending of silk protein with hygroscopic polyol additives (such as glycerol), and chemical modification of silk with hydrophilic chemistries (such a 4-sulfanilic acid, or poly-lysine). Several polyol plasticizers have been reported in recent studies as additives to make silk materials with elastic properties. See for example Jose, R. R., Brown, J. E., Polido, K. E., Omenetto, F. G., & Kaplan, D. L., Polyol-Silk Bioink Formulations as Two-Part Room-Temperature Curable Materials for 3D Printing, 1 ACS Biomaterials Science & Engineering 9, 780-788 (2015); see also Lu, Q., Hu, X., Wang, X., Kluge, J., Lu, S., Cebe, P., & Kaplan, D. L., Water-insoluble silk films with silk I structure, 6 Acta Biomaterialia 4, 1380-7 (2010); Pei, Y., Liu, X., Liu, S., Lu, Q., Liu, J., Kaplan, D. L., & Zhu, H., Mild process to design silk scaffolds with reduced β-sheet structure and various topographies at nanometer scale, 13 Acta Biomaterialia, 168-176 (2015). Preliminary studies have shown that certain polyols, specifically glycerol, have the intrinsic ability to induce physical crosslinking in silk, thus producing blended silk materials with high crystallinity and insolubility. While the current work has focused primarily on glycerol, little is understood regarding the silk-glycerol interactions that result in materials with high flexibility and shape memory properties. In silk-glycerol sponges, two main trends are observed: an increase in post-compression recovery and an increase in the compressive modulus of all sponges correlating to increases in glycerol concentration. In FIG. 15, compressive recovery, especially for sponges derived from low extraction times, steadily increases with glycerol content in methanol post-treated sponges. In sponges without methanol post-treatment, high glycerol content (40% w/w) showed reduced recovery for 60 mE sponges, no change in 30 mE sponges, and further improvement in 10 mE sponges. It is clear that extraction time plays a role in recovery of untreated silk-glycerol sponges. Secondary structure by FTIR shows an increase in crystallinity (β-sheet content) in high glycerol containing sponges, which likely contributes to mechanical robustness and shape recovery. However, the differences in secondary structure across extraction times are minimal within each group. Previous reports also describe silk sponges derived from low molecular weight silks are prone to collapse under physical loads, a phenomenon attributed to insufficient molecular entanglement. See for example Rnjak-Kovacina, J., Wray, L. S., Burke, K. A, Torregrosa, T., Golinski, J. M., Huang, W., & Kaplan, D. L., Lyophilized silk sponges: a versatile biomaterial platform for soft tissue engineering, 1 ACS Biomaterials Science & Engineering 4, 260-270 (2015). Low chain entanglement may be the reason silk sponges from longer extraction times show reduced recovery after compression.

Figure 24:
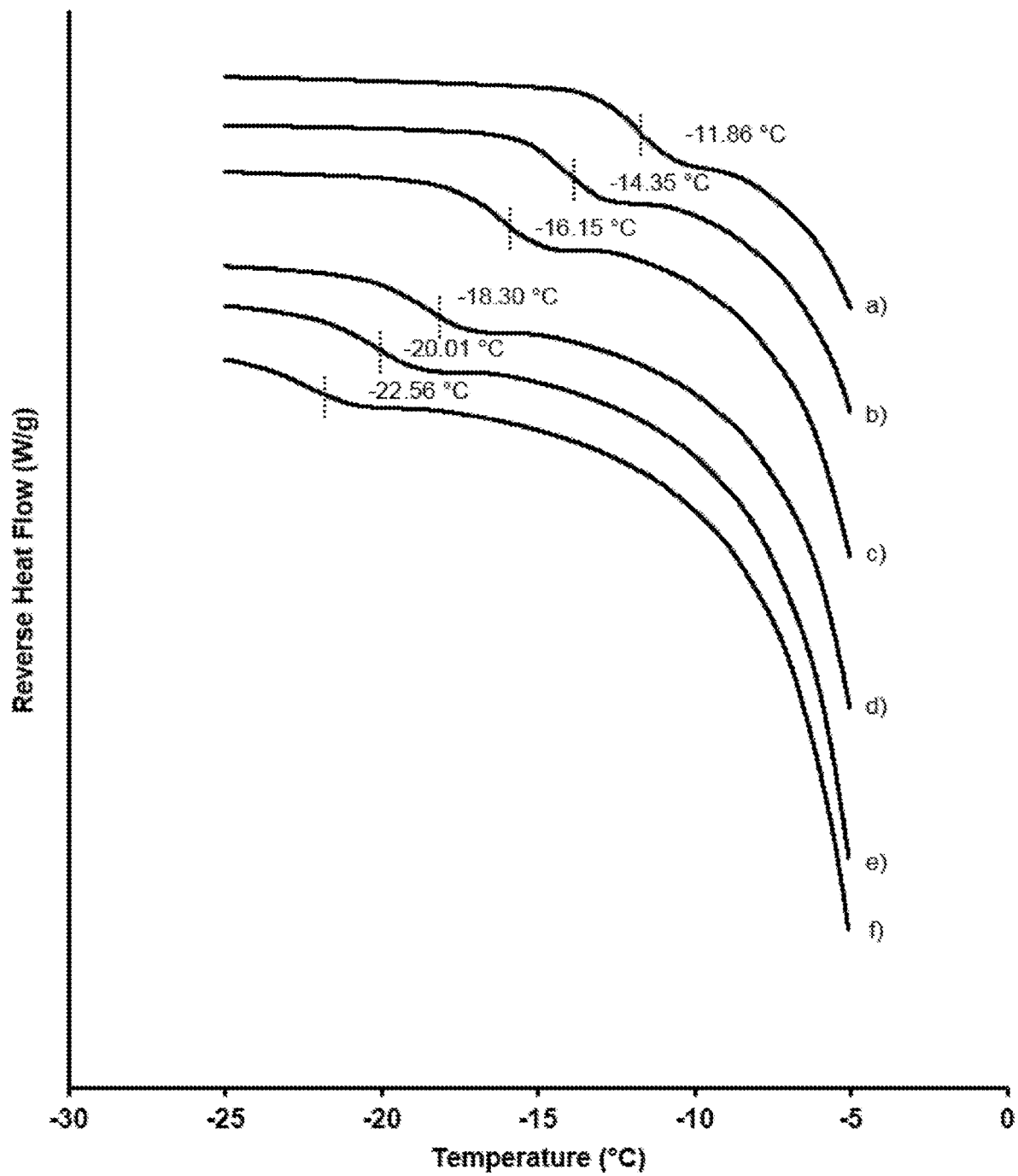
FIG. 24 shows differential scanning calorimetry of silk solutions containing varying amounts of glycerol from 0-10% w/w. The solution glass transition temperature (indicated with vertical hash marks) decreased with an increase in glycerol concentration in silk blends. This may have impacted the stability of the sponge during lyophilization, enabling structure collapse and densification during drying. Blend ratios as follows: a) Silk only; b) 2% w/w glycerol; c) 4% w/w glycerol; d) 6% w/w glycerol; e) 8% w/w glycerol; f) 10% w/w glycerol.

The increased compressive modulus of silk-glycerol sponges may be explained by the solution glass transition temperatures (solution Tgs) observed with differential scanning calorimetry (FIG. 24). Glycerol acts as an anti-freezing agent, lowering the Tg of silk-glycerol solutions. Our freeze-drying protocol primarily dries at −20° C., which is warmer than the glass transition temperature of a silk-glycerol (10% w/w) solution. This may result in collapse of the protein cake, potentially causing densification. Silk-glycerol sponges that were not methanol post-treated likely swelled in water, and the structural collapse was irrelevant. However, methanol treated sponges may have further crosslinked in this densified state, thus locking in a structure that was more dense than the silk only control sponges. It was expected that silk-glycerol materials would have lower elastic moduli compared to silk only controls; see for example Lu, Q., Hu, X., Wang, X., Kluge, J., Lu, S., Cebe, P., & Kaplan, D. L., Water-insoluble silk films with silk I structure, 6 Acta Biomaterialia 4, 1380-7 (2010); see also Pei, Y., Liu, X., Liu, S., Lu, Q., Liu, J., Kaplan, D. L., & Zhu, H., Mild process to design silk scaffolds with reduced β-sheet structure and various topographies at nanometer scale, 13 Acta Biomaterialia, 168-176 (2015) however, the densification in methanol treated sponges may explain the increased stiffness. Future work should study the mechanics of sponges formed at temperatures below the solution Tg, which may recapitulate the trends observed in other work.

Chemical modification of silk protein with hydrophilic groups has been previously reported. See for example Murphy, A. R., St John, P., & Kaplan, D. L., Modification of silk fibroin using diazonium coupling chemistry and the effects on hMSC proliferation and differentiation, 29 Biomaterials 19, 2829-38 (2008). These studies have assessed diazonium modification of silk materials for biocompatibility, drug delivery and protein structure. The work presented here focuses on the yet unexplored material properties of diazonium modified silk protein formats. As predicted, the addition of hydrophilic chemistries improved the uptake of aqueous media into the silk scaffold, and the inhibition of β-sheet crystal formation allowed for improved relaxation of the inner matrix, allowing volumetric swelling up to 80× its compressed state in certain formulations. Surprisingly, despite the significant reduction in β-sheet content, all diazonium sponges (both methanol and glycerol treated) were mostly insoluble. A more rigorous characterization of the materials is required to determine if sponges are partially soluble and where physical crosslinking is still occurring. Furthermore, all recovery/expansion tests in the current work were done in unconfined conditions. Future analysis should test sponge recovery in a confined state, mimicking implantation. It is unlikely that a 60% SAA/30% w/w glycerol silk sponges would possess the mechanical robustness to expand under confined conditions; however, sponges with lower modification may retain enough structure to exert an expansion force.

Figure 22:
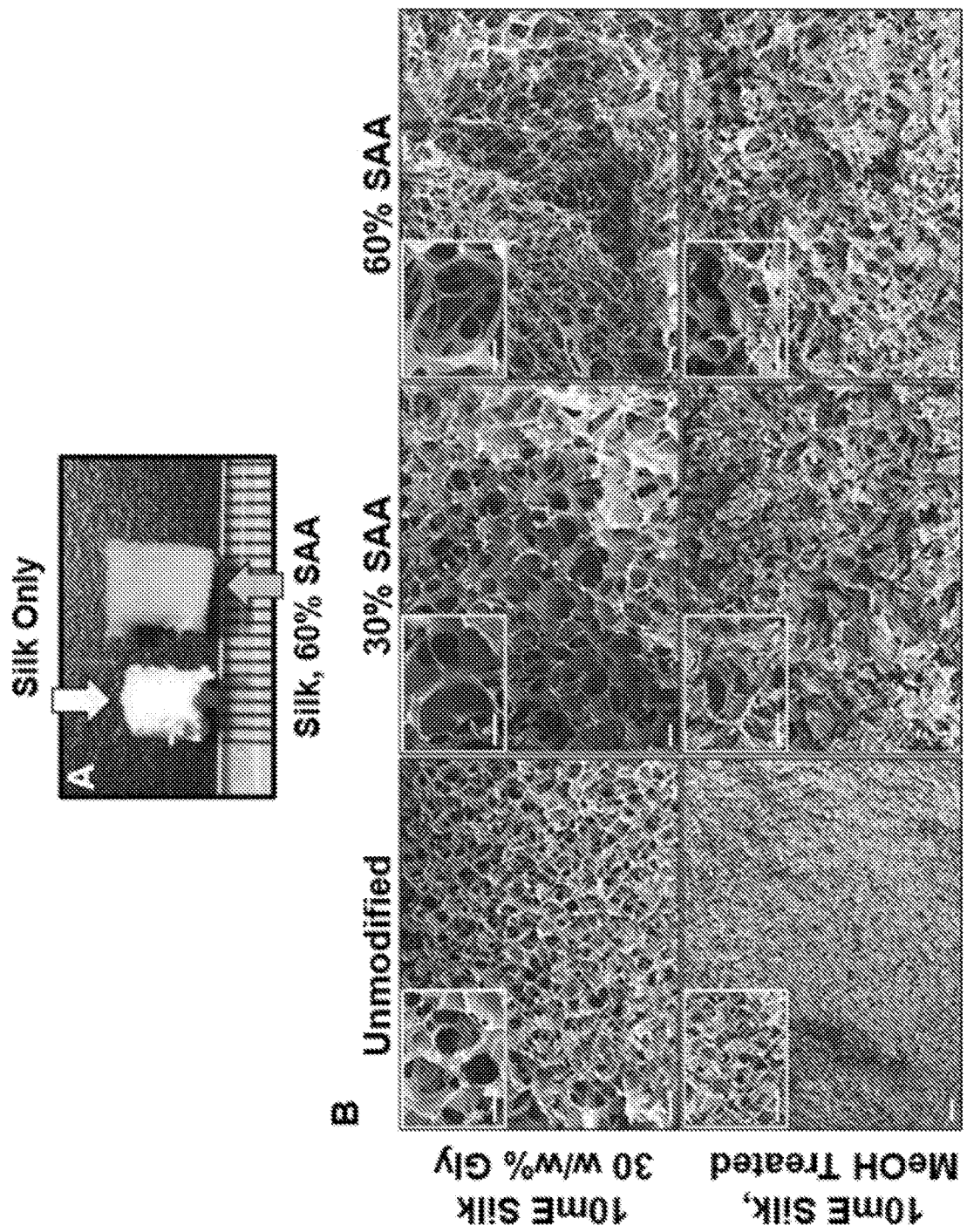
FIG. 22 shows pore morphology of modified silk sponges.
Figure 22:
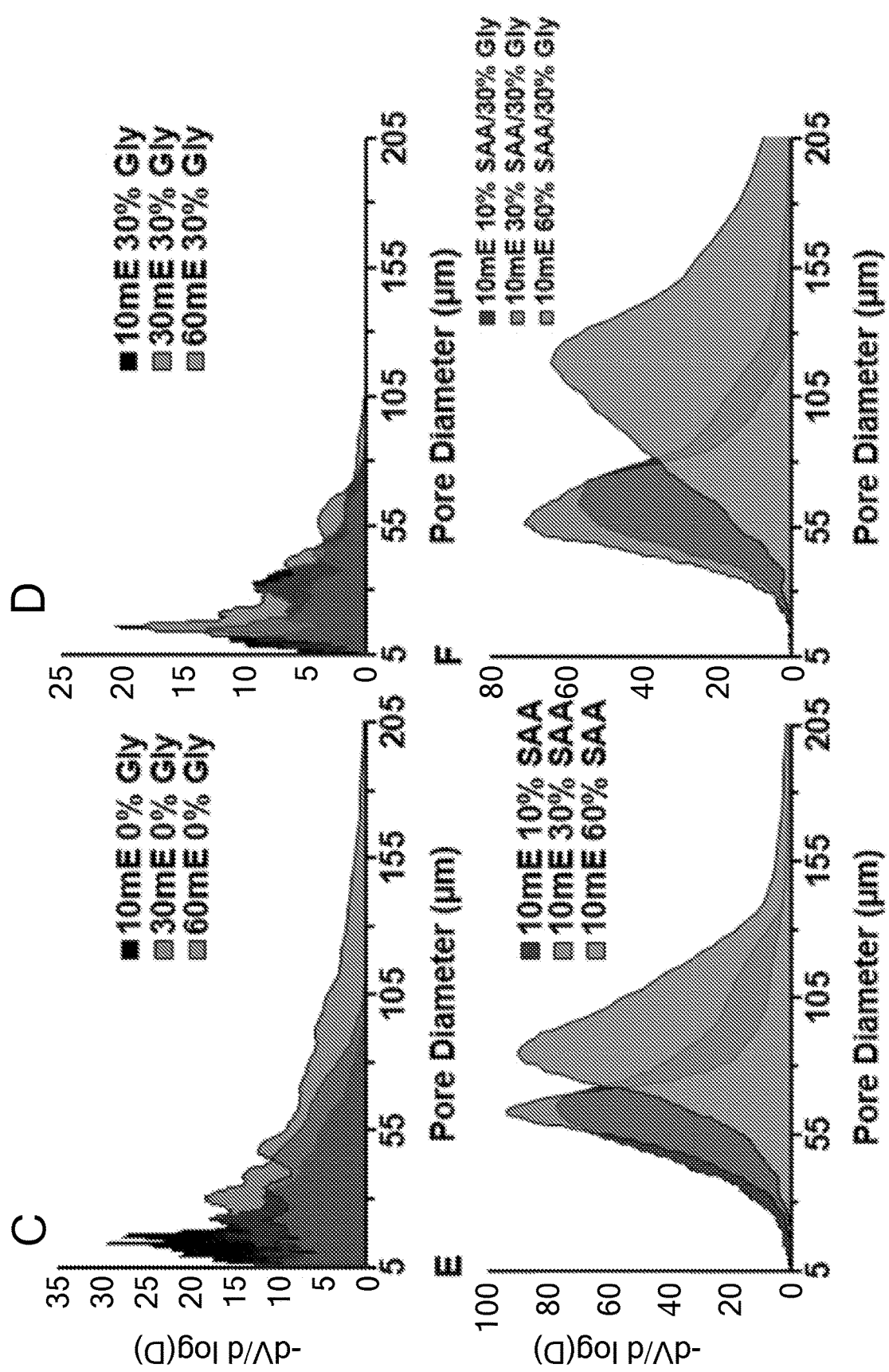

Pore morphology, interconnectivity and total volume were important characteristics in the development of our sponges. In general, matrices with small pores (<100 μm diameter) may not accommodate cellular infiltration as pores are too constrained, while large diameter pores may prevent adequate cell attachment. See for example Lutolf, M. P., & Hubbell, J. A. Synthetic biomaterials as instructive extracellular microenvironments for morphogenesis in tissue engineering, 2 3 Nature Biotechnology 1, 47-55 (2005); see also Rnjak-Kovacina, J., Wray, L. S., Burke, K. a, Torregrosa, T., Golinski, J. M., Huang, W., & Kaplan, D. L., Lyophilized silk sponges: a versatile biomaterial platform for soft tissue engineering, 1 ACS Biomaterials Science & Engineering 4, 260-270 (2015). In addition, total porosity and pore interconnectivity both play important roles in uptake of media and cell infiltration, which could impact volumetric swelling, material degradation and cell-mediated remodeling rate. Therefore, we elected to use a controlled freeze-drying process which is known to produce scaffolds with high porosity and interconnectivity. Pore shape can be altered during lyophilization by controlling the freezing temperature and ramp rate during cooling. See for example O'Brien, F. J., Harley, B. A., Yannas, I. V., & Gibson, L., Influence of freezing rate on pore structure in freeze-dried collagen-GAG scaffolds, 25 Biomaterials 6, 1077-1086 (2004). Since the goal was to create mechanically isotropic materials, we chose to use a slow freezing rate in a thermally conductive molding material to improve heat transfer and limit uni-directional ice crystal formation and elongated pores as seen in other studies. See for example Mandal, B. B., Gil, E. S., Panilaitis, B., & Kaplan, D. L., Laminar Silk Scaffolds for Aligned Tissue Fabrication, 13 Macromolecular Bioscience 1, 48-58 (2013). This method produced pores with a highly rounded morphology, as shown in FIG. 22.

Pore characteristics were measured by mercury intrusion porosimetry (MIP). While many previous studies have relied on scanning electron microscopy or histochemical staining to analyze pore geometry of polymer sponges, these methods can be subjective as material cross-sectioning can cause damage to the microstructure and may not result in pores with well-defined boundaries. MIP alternatively measures the porosity of an intact material throughout its entire volume. Unfortunately, the main limitation with several of these techniques is that the materials must be measured dry, while implanted materials would normally be fully hydrated. Dried sponges would predictably have smaller pore diameters compared to their hydrated state. Future studies analyzing porous scaffold morphology should include an analytical technical that can measure hydrated scaffolds with high resolution, such as micro-computed tomography or environmental SEM.

Nevertheless, we observed that the protein extraction time impacted the pore size heterogeneity, with longer extraction time resulting in greater polydispersity of pore shapes. This outcome may have to do with the viscosity of the solution, since shorter extraction times produces more viscous silk solutions, and high viscosity limits ice crystal formation and spreading. The addition of 30% w/w glycerol changes the material pore distribution by narrowing it between 5-55 μm diameters. The addition of glycerol has been shown to increase silk solution viscosity which may limit ice crystal growth in high extraction silk solutions; see for example Jose, R. R., Brown, J. E., Polido, K. E., Omenetto, F. G., & Kaplan, D. L., Polyol-Silk Bioink Formulations as Two-Part Room-Temperature Curable Materials for 3D Printing, 1 ACS Biomaterials Science & Engineering 9, 780-788 (2015) however, another explanation may be that glycerol can sequester water, enhancing protein-water separation and causing high density and low density protein regions during freeze-drying. Finally, the addition of tyrosine modified silk greatly increased the pore size in silk scaffolds. As expected, the hydrophilic chemistry and reduced β-sheet content allowed enhanced uptake of media and relaxation of the protein matrix to accommodate high swelling. As shown in FIG. 22, scanning electron microscopy reveals that the inner morphology of tyrosine modified silk sponges becomes more fibrillar with the addition of glycerol. The increased surface area likely contributes to the 60% SAA/30% w/w glycerol sponge's ability to uptake fluid. However, the material completely lacks rigidity and would be unsuitable as a bulking agent or tissue filler.

In all cases, pore morphology was measured in materials that had not previously undergone mechanical compression. Future studies should investigate the impact of high compression on the inner structure of porous materials. In this work, we assumed that volume recovery implied preservation of the initial matrix geometry, however, this may not be the case. High compression can cause cell walls to collapse, crack or irreversibly deform. Shape fidelity, as assessed by comparing mechanical compression before and after 80% strain, is a useful metric in estimating pore damage, since the mechanical properties of a sponge are in large part related to cell wall integrity. Glycerol containing sponges without methanol post-treatment presented no significant difference between pre- and post-compressive modulus independent of extraction time, indicating that glycerol may improve wall flexibility, preserve mechanical integrity and prevent permanent deformation or fracture. However, closer examination of the pore wall surface, perhaps at the nanoscale, will be assessed in future work to determine true resistance to fatigue.

In vivo evaluation revealed that silk-glycerol sponges experience a significant increase in degradation rate compared to silk only controls when implanted subcutaneously (FIG. 23). This is consistent with a recently published in vitro degradation study showing increased degradation rate of silk-glycerol sponges in protease solution compared to silk only controls. See for example Pei, Y., Liu, X., Liu, S., Lu, Q., Liu, J., Kaplan, D. L., & Zhu, H., Mild process to design silk scaffolds with reduced β-sheet structure and various topographies at nanometer scale, 13 Acta Biomaterialia, 168-176 (2015). To be clear, sponge degradation was quantified by measuring sample diameter using calipers, not by measuring the area of un-infiltrated space. Sponge diameter and cell infiltration depth were two separate attributes, as we often observed residual silk among the fibrous tissue infiltrate. The increased cellular infiltration into silk-glycerol sponges, however, likely explains the rapid degradation, as silk material breakdown was largely cell mediated. In addition, sponge diameter did not appear to decrease as a result of physical compression. By histological examination, pore volume appears to be roughly comparable at all time points. If sponges were being compressed in vivo, we would likely observe densification of the bulk material. Additionally, we noted the absence of multinucleated giant cells at all time points indicating minimal tissue inflammation. See for example Meinel, L., Hofmann, S., Karageorgiou, V., Kirker-Head, C., McCool, J., Gronowicz, G., Kaplan, D. L., The inflammatory responses to silk films in vitro and in vivo, 26 Biomaterials 2, 147-155 (2005); see also Thurber, A. E., Omenetto, F. G., & Kaplan, D. L., In vivo bioresponses to silk proteins, 71 Biomaterials, 145-157 (2015).

It is unclear why cells are able to better infiltrate into silk-glycerol sponges. One explanation may be that silk-glycerol sponges have enhanced swelling capacity in aqueous media, causing pore diameters to increase and therefore allow better access to the surrounding cells. Alternatively, glycerol is a derivative of fat and oils intrinsic to the body. Residual glycerol present within the silk sponges may be recognized by cells, prompting migration into what is otherwise a foreign material. Future in vivo trials must examine how degradation rate and cellular infiltration is affected by glycerol content, as only 30% w/w glycerol ratios were observed in this study.

Lastly, the material mechanics, pore morphology and in vivo degradation rate were all examined at a single concentration of silk protein (3% w/v). Higher protein concentrations would likely increase elastic modulus for all sponges, making the materials suitable for repairing a wider range of soft tissues, as well as extend volume retention in vivo, however, it is unclear how the recovery and shape memory characteristics would compare to the current sponges. 3% w/v protein concentration was originally chosen to mimic the modulus of adipose tissue, though many tissue bulking procedures may require longer volume retention than the current silk-glycerol sponges are capable of in order to support adequate tissue regeneration. For applications requiring short term bulking (3-6 months), 3% w/v silk sponges with 30% w/w glycerol are ideal candidates for rapid tissue integration and recapitulation of native soft tissue mechanics.

Conclusions

The approach discussed here improves upon the current silk sponge technology by providing a material which can undergo rapid compressive recovery triggered by the presence of aqueous media like water or PBS. The use of diazonium chemical modifications and glycerol additives give silk protein sponges the ability to swell, making the materials useful in filling void space or wounds in the body and enhancing cellular infiltration for tissue remodeling. These modified silk sponges could be used as soft tissue fillers for skin defects, aesthetic enhancements (breast, thigh, butt, etc.) or as resorbable grafts for facial disfigurement. Additionally, the elastomeric properties of these silk sponges would make them viable candidates for minimally invasive implantation strategies in drug delivery, tissue regeneration or wound clotting. Future work will determine how to further tune mechanics and degradation by altering glycerol concentration, hydrophilicity, silk molecule cross-link density and protein concentration.

OTHER EMBODIMENTS AND EQUIVALENTS

While the present disclosure has explicitly discussed certain particular embodiments and examples of the present disclosure, those skilled in the art will appreciate that the invention is not intended to be limited to such embodiments or examples. On the contrary, the present disclosure encompasses various alternatives, modifications, and equivalents of such particular embodiments and/or example, as will be appreciated by those of skill in the art.

Accordingly, for example, methods and diagrams of should not be read as limited to a particular described order or arrangement of steps or elements unless explicitly stated or clearly required from context (e.g., otherwise inoperable). Furthermore, different features of particular elements that may be exemplified in different embodiments may be combined with one another in some embodiments.

What is claimed:

1. A method comprising steps of:
   cooling a silk fibroin solution to a freezing temperature of less than, or equal to, −20° C., which cooling is performed at a cooling rate from −10° C./min to −0.001° C./min;
   lyophilizing the silk fibroin solution at the freezing temperature to form a silk material characterized by two or more of the following:
   interconnected, evenly spaced pores having rounded morphology;
   substantial absence of ice crystals; and
   substantial uniformity of pore shape.

2. The method of claim 1, wherein the silk material comprises silk fibroin having an average molecular weight in a range between about 500 Da and about 3000 kDa.

3. The method of claim 1, wherein the silk fibroin solution contains about 0.1% (w/v) to about 50% (w/v) silk fibroin.

4. The method of claim 1, wherein the silk fibroin solution contains a plasticizer.

5. The method of claim 4, wherein a weight ratio of plasticizer: silk is between about 0.05 and about 0.8.

6. The method of claim 4, wherein the silk fibroin is a modified silk fibroin in that between about 5% and about 75% of its tyrosine residues are covalently modified.

7. The method of claim 6, wherein the step of modifying tyrosine residues in the silk fibroin is with sulfonic acid.

8. The method of claim 6, wherein the modifying step comprises reacting via a diazonium coupling reaction to form sulfonic acid-modified tyrosine residues.

9. The method of claim 1, comprising treating the silk material to render it insoluble.

10. The method of claim 9, wherein the step of treating comprises exposing the silk material to methanol.

11. The method of claim 1, wherein when the silk material has greater than 20% (w/w) plasticizer, the material is insoluble.

12. The method of claim 1, wherein the freezing temperature is within a range of about −20° C. to about −50° C.

13. The method of claim 1, wherein the cooling rate is within the range of about −10° C./min to −0.005° C./min.

14. The method of claim 1, wherein the step of cooling comprises maintaining the silk fibroin solution in a container.

15. The method of claim 14, wherein the thermal conductivity and geometry of the container is such to uniformly freeze the silk material.

16. The method of claim 1, wherein a storage modulus value of the silk material is in a range between about 5 kPa and about 2000 kPa.

17. The method of claim 16, wherein an average molecular weight of the silk fibroin in the silk fibroin solution is in a range between about 10 kDa and about 400 kDa.

18. The method of claim 16, wherein the concentration of silk fibroin in the silk fibroin solution is in a range of about 0.1 wt % to about 50 wt %.

19. The method of claim 4, wherein the plasticizer content of the silk fibroin solution is up to about 40% (w/w).

20. The method of claim 8, wherein the concentration of the sulfonic acid modified tyrosine residues within the modified silk fibroin is between about 5% and about 75%.

* * * * *